United States Patent [19]

Manaka et al.

[11] Patent Number: 5,551,283
[45] Date of Patent: Sep. 3, 1996

[54] ATMOSPHERE MEASURING DEVICE AND FLOW SENSOR

[75] Inventors: Junji Manaka; Tetsuo Ishibashi, both of Tokyo, Japan

[73] Assignee: Ricoh Seiki Company, Ltd., Tokyo, Japan

[21] Appl. No.: 285,666

[22] Filed: Aug. 3, 1994

[30] Foreign Application Priority Data

Aug. 10, 1993 [JP] Japan .................................. 5-198148
Aug. 20, 1993 [JP] Japan .................................. 5-206388

[51] Int. Cl.$^6$ .......................... G08B 17/10; G01F 1/68; G01N 25/18
[52] U.S. Cl. .......................... 73/31.01; 73/29.01; 73/75; 73/204.11; 73/25.04; 340/634
[58] Field of Search ................. 73/31.01, 29.01, 73/75, 204.11, 204.14, 29.02, 24.04, 25.04; 340/634

[56] References Cited

U.S. PATENT DOCUMENTS

| | | | |
|---|---|---|---|
| 2,949,765 | 8/1960 | Thayer et al. | 73/27 |
| 3,549,327 | 12/1970 | Fergusson | 23/232 |
| 3,864,959 | 2/1975 | MacDonald | 73/27 R |
| 3,886,797 | 6/1975 | Bauer | 73/335 |
| 3,905,230 | 9/1975 | Calvet et al. | 73/204 |
| 3,913,379 | 10/1975 | Rusz et al. | 73/27 R |
| 4,043,196 | 8/1977 | Trageser | 73/204 |
| 4,123,934 | 11/1978 | Höht | 73/27 R |
| 4,164,862 | 8/1979 | Jackson | 73/27 R |
| 4,532,797 | 8/1985 | Yang | 73/75 |
| 4,594,879 | 6/1986 | Maeda et al. | 73/27 R |
| 4,682,503 | 7/1987 | Higashi et al. | 73/755 |
| 4,896,143 | 1/1990 | Dolnick et al. | 340/634 |
| 4,902,138 | 2/1990 | Goeldner et al. | 374/44 |
| 5,117,691 | 6/1992 | Fraser | 73/204.15 |
| 5,379,630 | 1/1995 | Lacey | 73/25.03 |

OTHER PUBLICATIONS

Patent Abstracts of Japan, vol. 17, No. 553 (P–1625) 5 Oct. 1993 & JP–A–05 157 759 (Zexel).
Patent Abstracts of Japan, vol. 12, No. 331 (P–755) 7 Sep. 1988 & JP–A–63 094 144 (Yokogawa Hewlett Packard).
Database WPI, Week 8135, Derwent Publications Ltd., London, GB; AN 81–J1003D 35 & SU–A–777 585 (UFA Aviation) 8 Nov. 1980.

*Primary Examiner*—Hezron E. Williams
*Assistant Examiner*—J. David Wiggins
*Attorney, Agent, or Firm*—Jordan and Hamburg

[57] ABSTRACT

A low-cost and quick-response type gas-density sensing element is free from positioning error of sensing ambient temperature and gas density and can accurately sense the gas flow even if the environmental conditions sharply change. An output voltage $V_1$ proportional to an ambient temperature is obtained by heating a sensing element at low temperature and an output voltage $V_2$ proportional to the ambient temperature and humidity is obtained by heating the sensing element at a high temperature. An output voltage which is proportional to the humidity is obtained by subtracting the voltage value $V_1$ from the voltage value $V_2$.

20 Claims, 41 Drawing Sheets

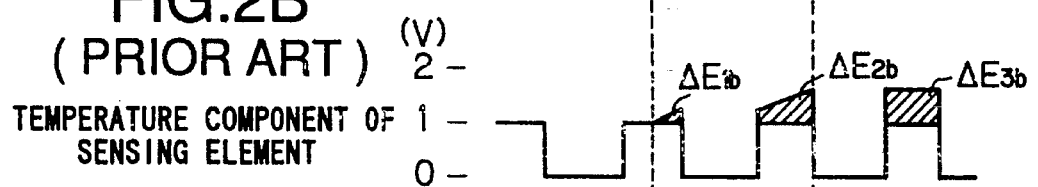
FIG. 2A (PRIOR ART) AMBIENT TEMPERATURE
FIG. 2B (PRIOR ART) TEMPERATURE COMPONENT OF SENSING ELEMENT
FIG. 2C (PRIOR ART) TEMPERATURE COMPONENT OF COMPENSATING ELEMENT
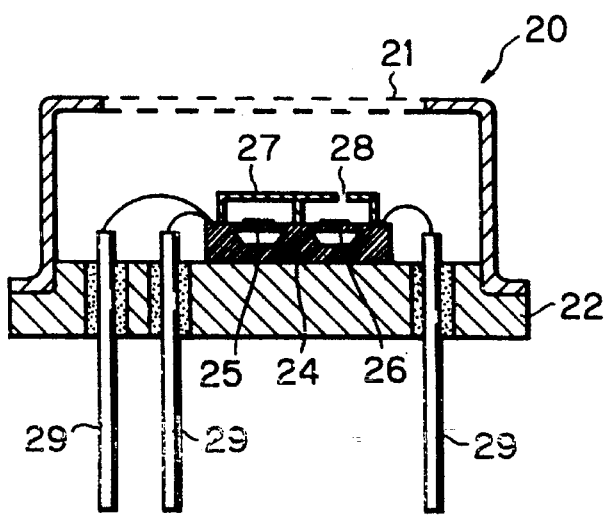
FIG. 3 (PRIOR ART)

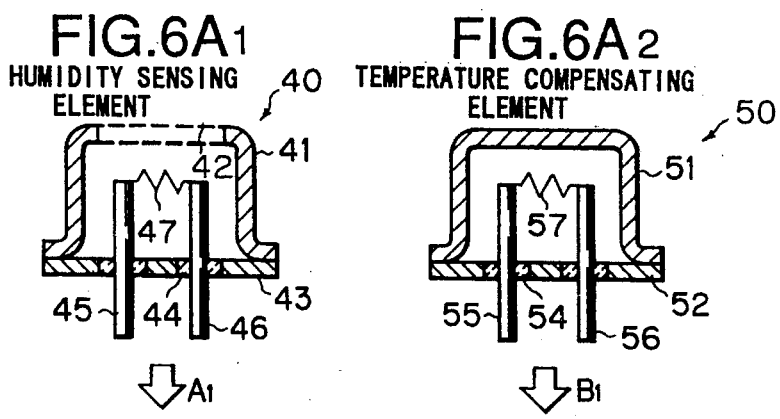
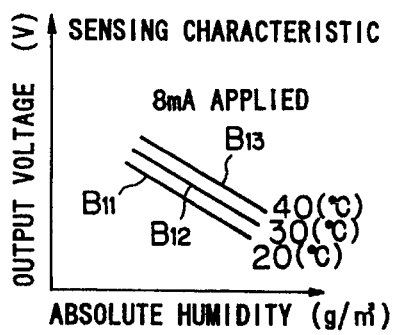 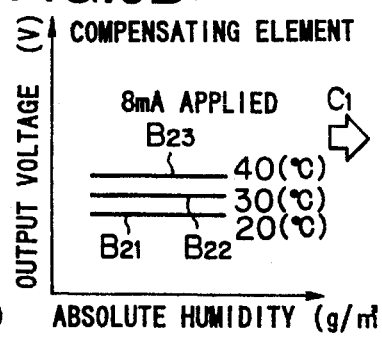 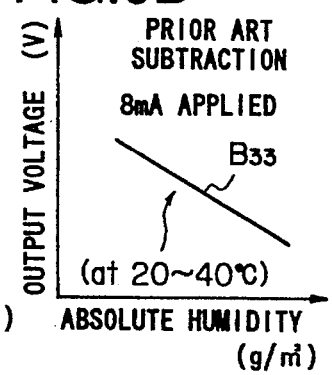
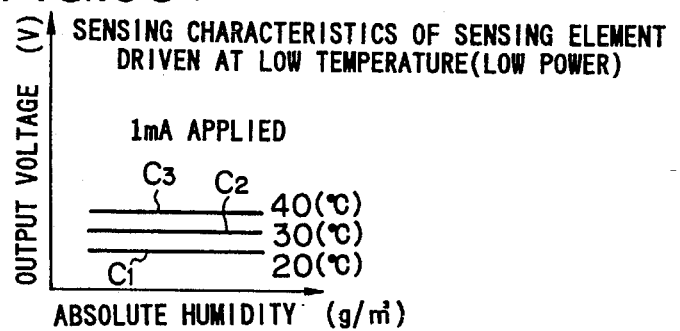
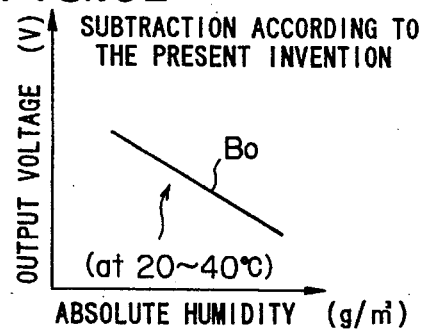

HUMIDITY CHARACTERISTIC CURVES (at 30°C)

TEMPERATURE CHARACTERISTIC CURVES (at 0g/m³)

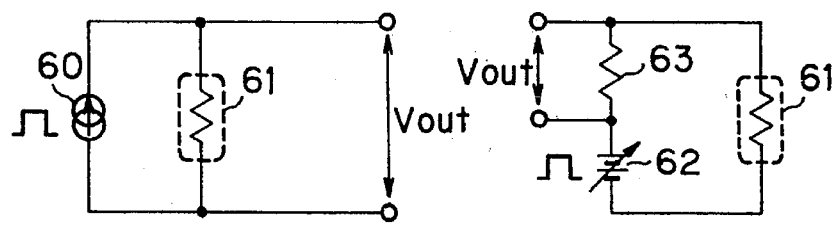
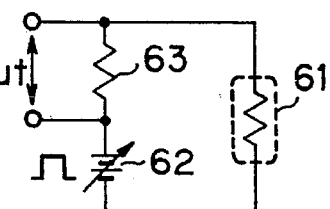
FIG.8A₁  FIG.8A₂
FIG.8B
FIG.8C
FIG.8D

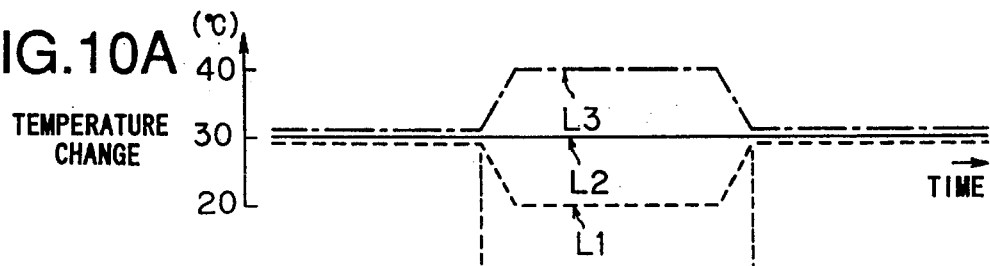
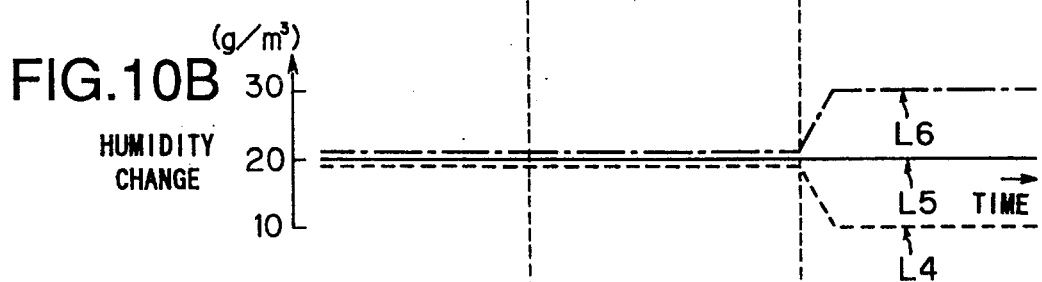
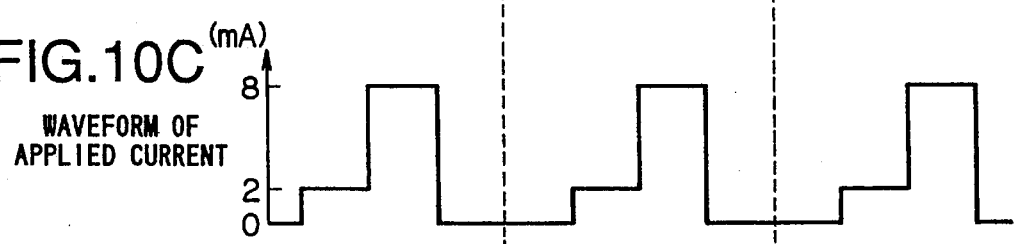
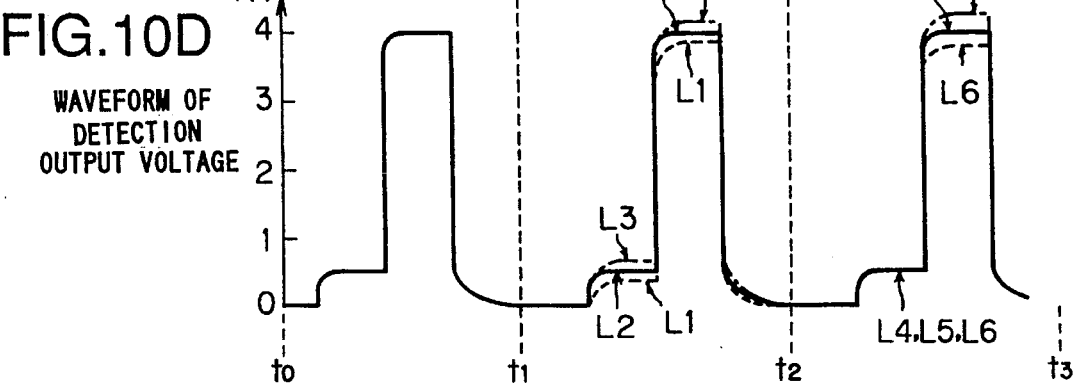

SW1a

SW2b is

Vs

Vs'

Vs"

VD

V t1 t2 t3 t4

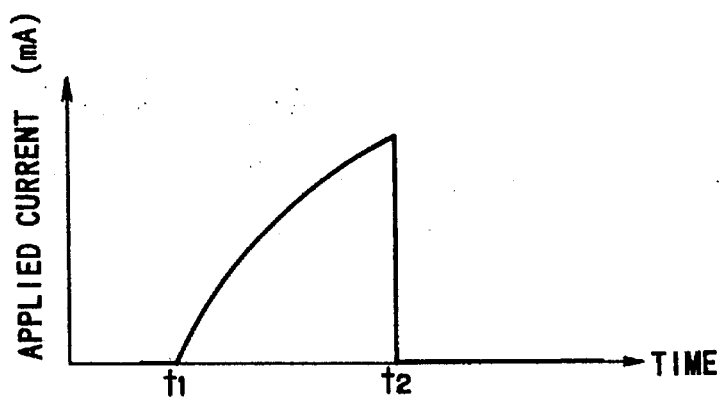
FIG.16A
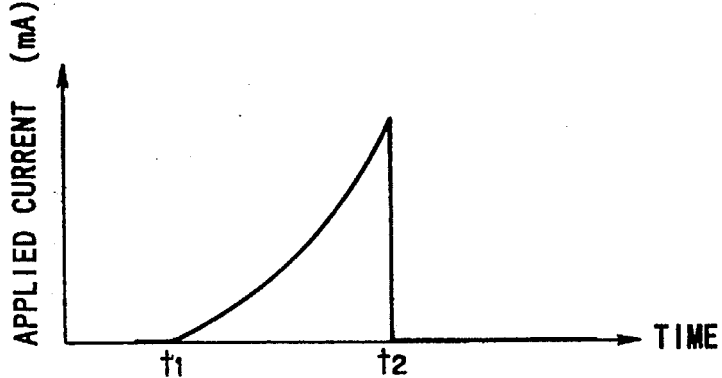
FIG.16B
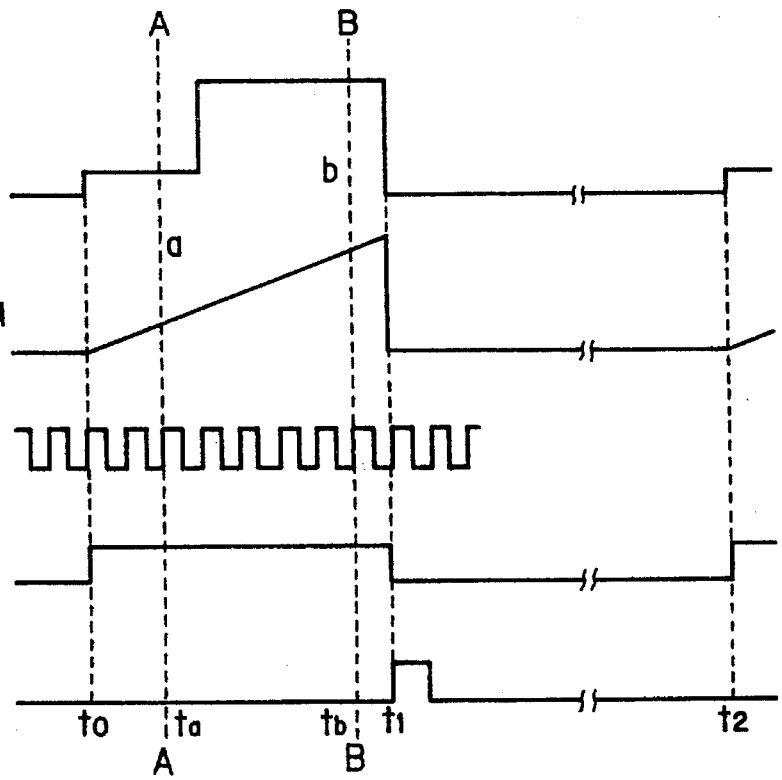
FIG.17A WAVEFORM OF OUTPUT VOLTAGE AT LOW AND HIGH TEMPERATURES
FIG.17B SAW-TOOTH WAVEFORM OF OUTPUT VOLTAGE
FIG.17C CLOCK PULSE
FIG.17D MEASUREMENT ON-OFF SIGNAL
FIG.17E RESET SIGNAL

FIG. 19
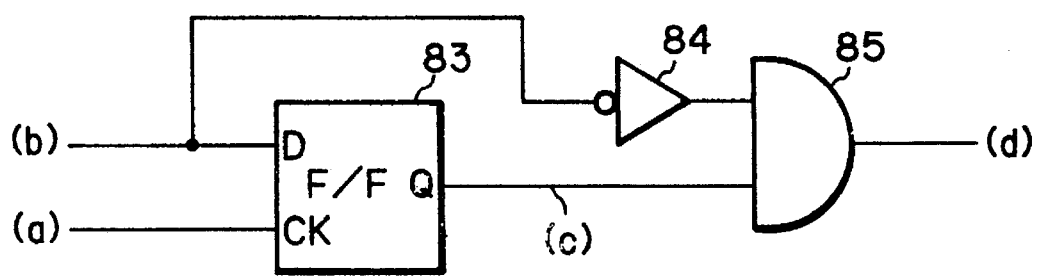
FIG. 20A   CK CLOCK
FIG. 20B   ON-OFF SIGNAL
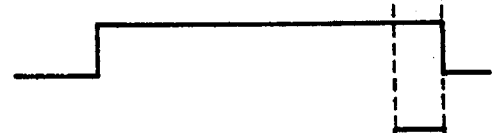
FIG. 20C   Q
FIG. 20D   RESET SIGNAL

FIG.26
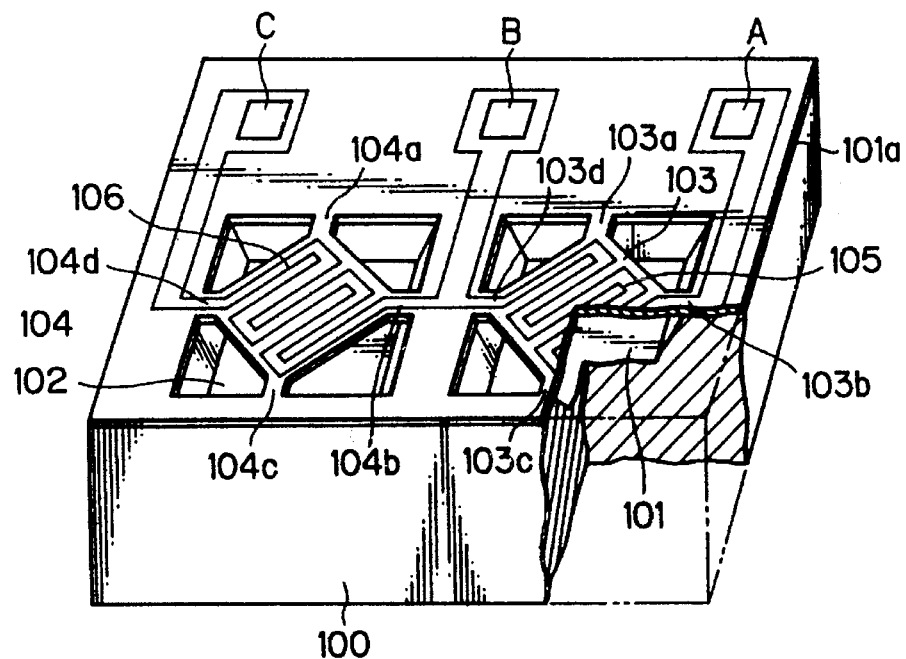
FIG.27A
WAVEFORM OF CLOCK PULSE
FIG.27B
POWER APPLIED BETWEEN C-B
(TEMPERATURE SENSING)
FIG.27C
POWER APPLIED BETWEEN B-A
(TEMPERATURE-HUMIDITY SENSING)
FIG.27D
HUMIDITY SENSING
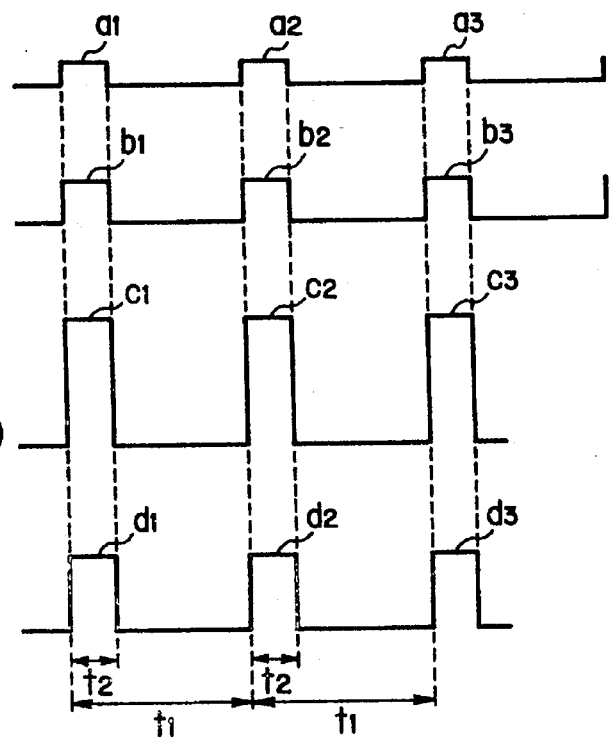

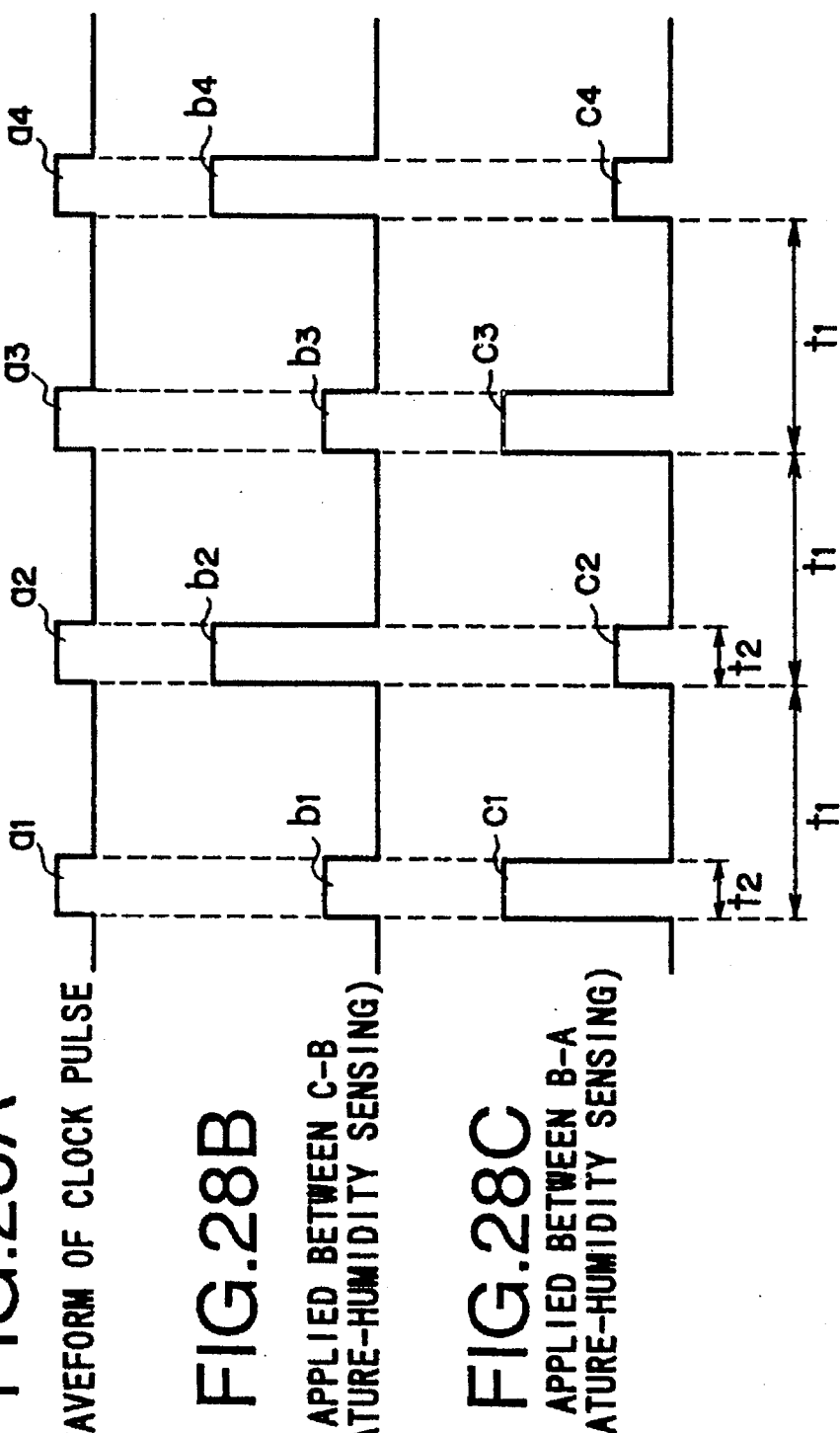

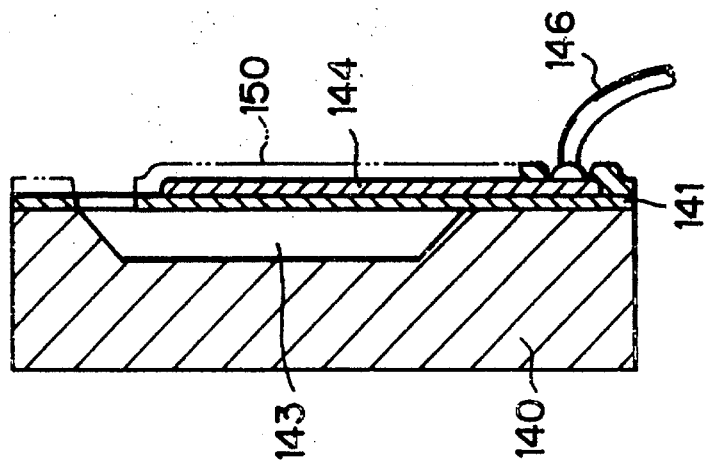
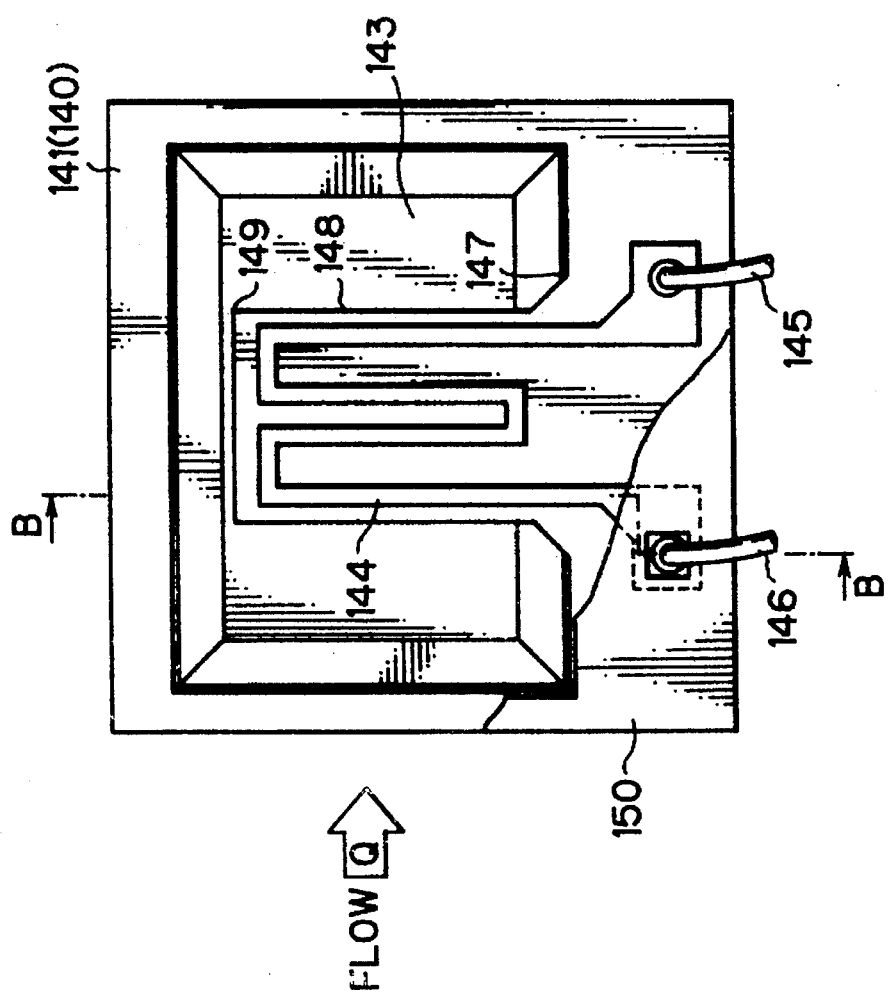

PULSE DRIVING SYSTEM

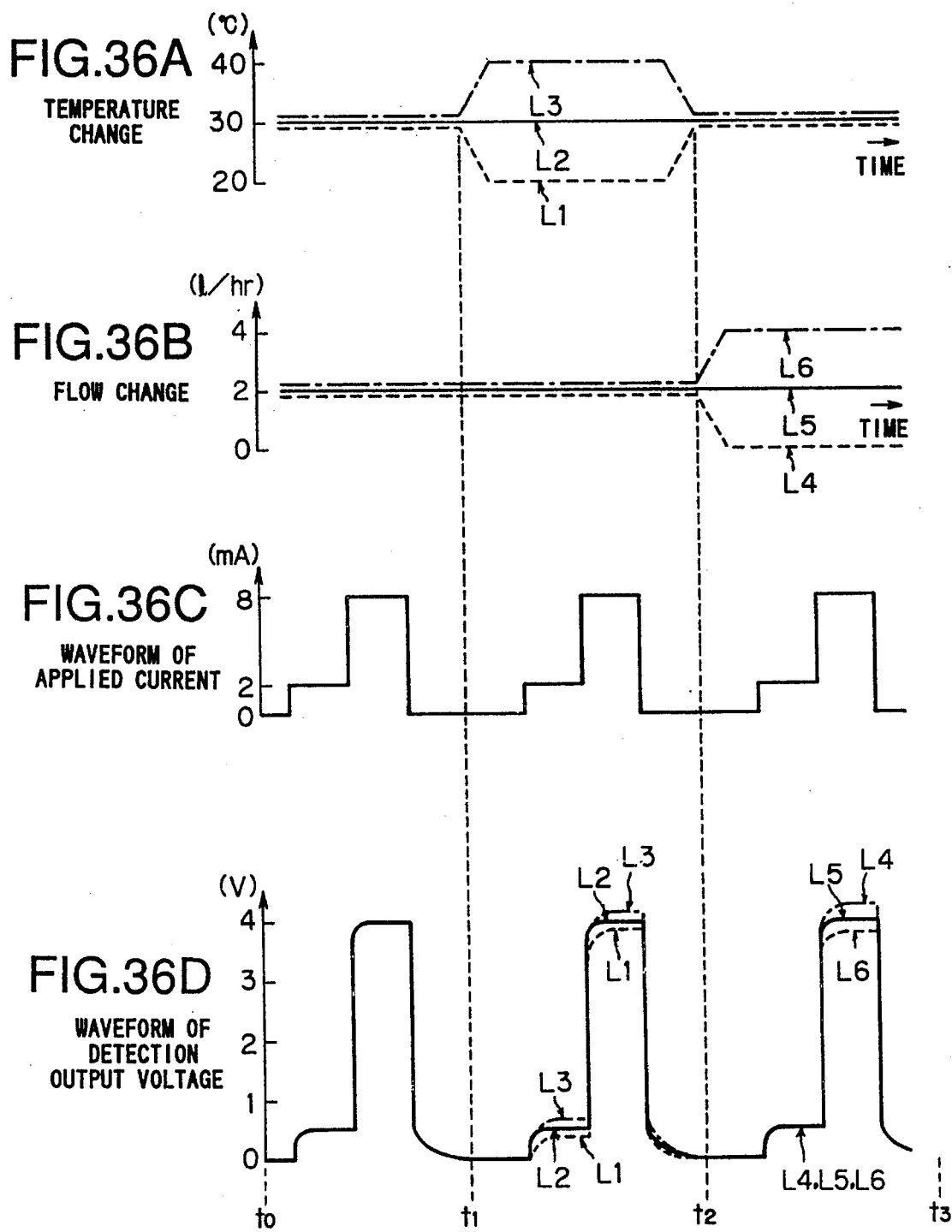

FIG.40A SW1a
FIG.40B SW2b
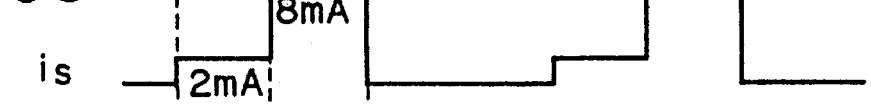
FIG.40C is  2mA  8mA
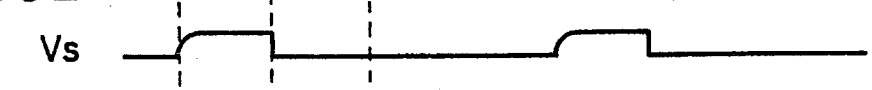
FIG.40D Vs
FIG.40E Vs'
FIG.40F Vs"
FIG.40G VD
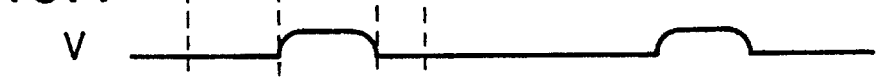
FIG.40H V
t1  t2  t3 t4

FIG.42A WAVEFORM OF OUTPUT VOLTAGE AT LOW AND HIGH TEMPERATURES

FIG.42B SAW-TOOTH WAVEFORM OF OUTPUT VOLTAGE

FIG.42C CLOCK PULSE

FIG.42D MEASUREMENT ON-OFF SIGNAL

FIG.42E RESET SIGNAL

FIG.44
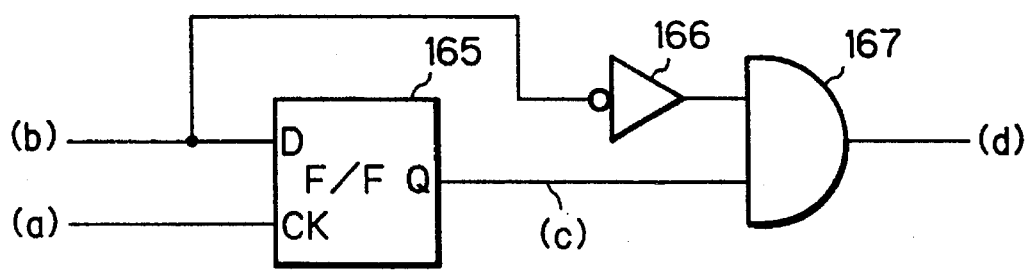
FIG.45A  CK CLOCK 
FIG.45B  ON-OFF SIGNAL 
FIG.45C  Q 
FIG.45D  RESET SIGNAL 

FIG.53
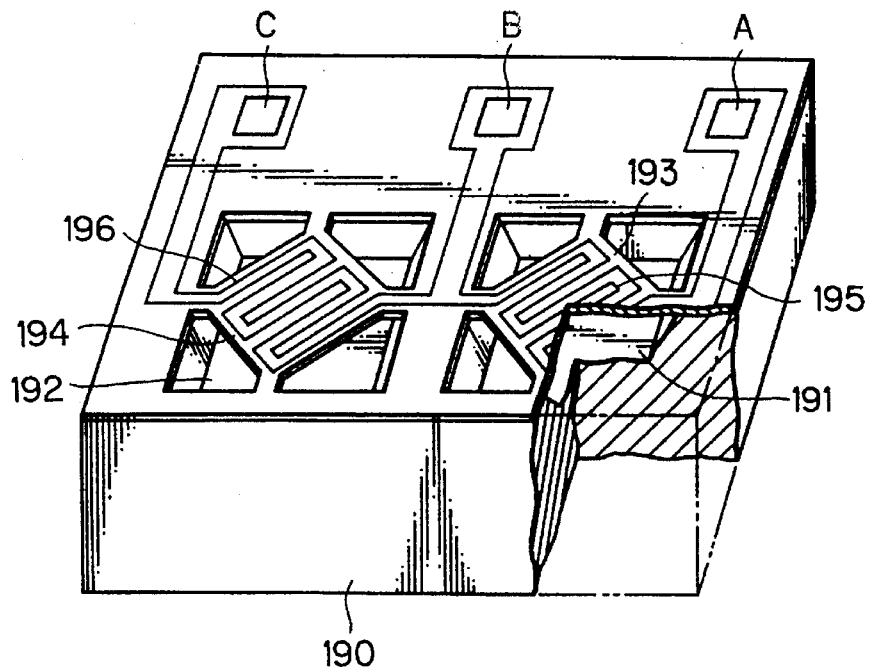
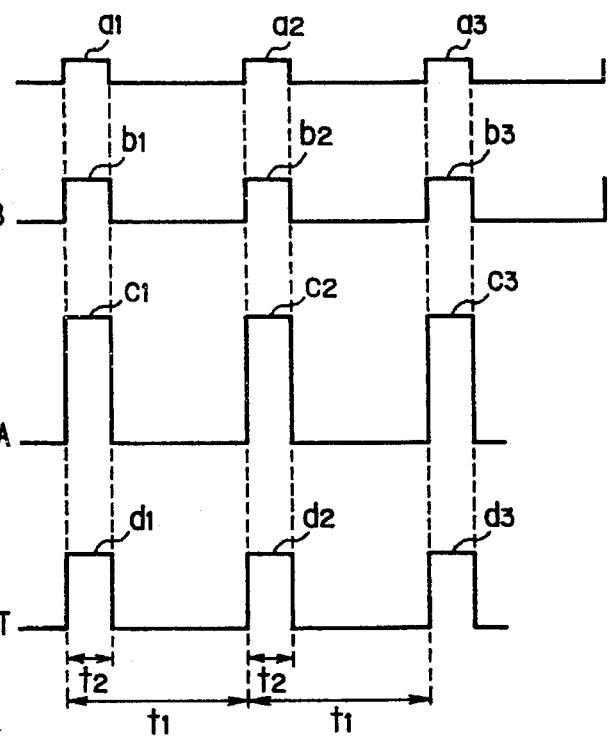
FIG.54A WAVEFORM OF CLOCK PULSE
FIG.54B CURRENT APPLIED BETWEEN C-B
FIG.54C CURRENT APPLIED BETWEEN B-A
FIG.54D FLOW SPEED DETECTION OUTPUT

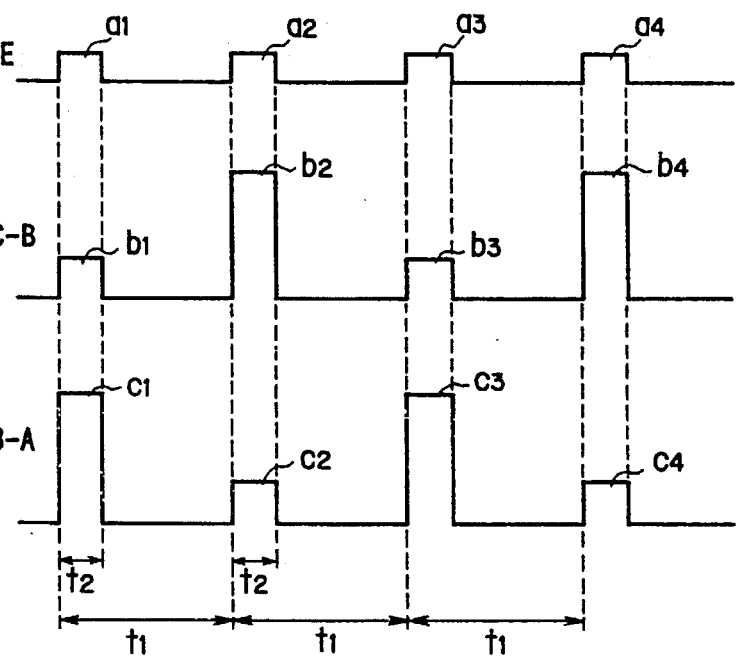
FIG. 55A WAVEFORM OF CLOCK PULSE
FIG. 55B POWER APPLIED BETWEEN C-B
FIG. 55C POWER APPLIED BETWEEN B-A

ATMOSPHERE MEASURING DEVICE AND FLOW SENSOR

BACKGROUND OF THE INVENTION

The present invention relates to a atmosphere measuring device and more particularly to a self-compensating type atmosphere measuring device which is capable of measuring the density of gas according to a differential resistance of a resistor heated with low and high electric powers in an ambient atmosphere to be measured, and which is suited to use in various measuring devices such as for example hygrometers, gas chromatographs, vacuum gauges, dew-point hygrometers, hot-wire anemometers and so on.

It is well known that the density of a specified gas contained in a mixed atmosphere can be thermally detected on the basis of a difference of thermal conductivities of the gas, which varies depending upon its molecular weight. Among atmosphere measuring devices working on this measuring principle, hygrometers find particularly extensive application, for example, as humidity controllers for quality control in the production process of electronic parts (e.g., semiconductors), optical precision devices, fibers, foods and other goods, and as sensing terminals for environmental control in hospitals, buildings and like installations.

In view of these circumferences, a hygrometer will be described below as a preferred embodiment of the present invention, but the present invention is not limited to said application and widely relates to general atmosphere measuring devices for measuring the density of a mixed gas and, more practically, to above-mentioned various measuring devices.

Hygrometers are roughly classified into two groups according to measuring principles—one is electrical variation detecting type and the other is mechanical variation detecting type. Both types pose problems on their reliability and duration of life, and many of them have poor response characteristics.

The electric hygrometers using the thermal conductivity of gas are known to be of high response and high reliability. The heat that flows in unit time in the normal direction passing an upper and a lower planes of a specified cross section of an isotropic body is proportional to the temperature gradient and the cross-sectional area. This proportional constant is thermal conductivity. The thermal conductivity of a gas is a function of isopiestic specific heat that is further a function of the gas molecular weight. Therefore, the thermal conductivity of only air differs from the thermal conductivity of air containing therein moisture and gas components having different molecular weights. There is such a hygrometer which, utilizing a difference of thermal conductivities of gases, determines the humidity of an ambient atmosphere by measuring a change in resistance of a sensing element (resistor), which is caused by a heat radiation from the heated resistor into the atmosphere.

In a practical hygrometer, a temperature-compensating element which has a resistor mounted in a closed compartment filled with dry air at a constant pressure and a sensing element which has a resistor exposed to an atmosphere whose humidity is to be measured are disposed close to each other. Both resistors are heated with a constant electric power and change their resistance values. A change of resistance by the effect of the humidity (moisture content of the atmosphere) is determined by reducing, i.e.—subtracting, the resistance value of the temperature compensating element from the resistance value of the sensing element.

However, the hygrometers which use a combination of a two elements (a temperature-compensating element and a humidity-sensing element) have such a common problem that the temperature-compensating element, if being filled with dry air at a pressure other than the specified constant pressure, can not serve as a reference. If the dry air has a different pressure, its thermal conductivity changes and the temperature sensing element has a different temperature-sensing characteristic.

Furthermore, the specified pressure of the dry air in the temperature compensating element serves as a reference for compensation of measurement when sensing the humidity of an atmosphere, but thermal conductivity of the dry air may vary with a change of the ambient pressure (of an atmosphere containing a moisture), reducing its effectiveness of the reference. Accordingly, the humidity of the dry air and the dry air filling conditions shall be very strictly controlled because any variation of these conditions leads to variations of the characteristics of the products. Furthermore, a combination of a sensing element with a temperature-compensating element requires complicated matching operations. All the above-mentioned facts lead to decreasing of the yield of products.

The pressure of the dry air charged in an enclosure of the temperature-compensating element is constant, but the ambient atmosphere may change its pressure under different meteorological conditions (e.g., at a highland place) and therfore change its thermal conductivity. If the pressure of the dry air in the enclosure of the temperature-compensating element can vary according to the working conditions with change of the outside air pressure, the temperature compensation is possible. But, sealing caps of prior art devices are not so flexible in its material and construction as it may be deformed to change its inner pressure with change of the atmospheric pressure. Consequently, the prior art devices can not get the correct value of the humidity under the above-mentioned conditions. When the atmosphere to be detected is partially dense and the sensing element and temperature-compensating element are widely separated from each other, detection signals represent only comparison values obtained at separate (not the same) positions and they can not be accepted as the data obtained under the same conditions. Therefore, it is desired to dispose the sensing element and the temperature-compensating element at a possibly minimal distance to each other. For instance, it has been proposed to arrange these elements on one substrate, but further close arrangement of the elements has been still required.

The above-mentioned conventional atmosphere measuring devices, each using a combination of a separate sensing element and a separate temperature-sensing element, have such drawbacks that they can not be applicable for wide range of humidity measurement and can not attain a higher sensing performance if elements have not matched characteristics of resistance (volt-ampere characteristic), resistance temperature coefficient, response time (building-up time) and aging. These severe requirements on matched characteristics of paired elements lead to increasing their manufacturing cost because of correspondingly reduced mass productivity and product yield and of increased man-hours. The conventional device consumes a relatively large electric energy since its sensing element and temperature compensating element are powered from respective power sources. The present invention also relates to a flow sensor and, more particularly, to a flow sensor which is suitable for use in a thermal type flowmeter based upon that electrical resistance value of a resistor disposed in a flowing fluid and heated therein varies with change of the fluid temperature and flow rate.

The thermal flowmeters having no moving portion thanks to their compactness and high-speed response have been now used in various fields of application. Recently, the thermal flowmeters have drawn the increasing attention as a device suited for regulating air flow so as to get an optimal air-fuel ratio in internal-combustion engines. A resistor heated at a specified electric power becomes to have a temperature at which the heat generated from the heating electrical energy and the heat radiated by a fluid flow are balanced with each other. Consequently, the heat radiation is a function of the flow rate, isopiestic specific heat and density of a fluid. In any thermal flowmeter based on this principle, a resistor disposed in a gas flow is heated with a constant electric power, a measured resistance value of the resistor is reduced by a resistance value corresponding to a measured temperature of the fluid to eliminate the thermal influence of the fluid, and the mass flow rate of the fluid is determined from the corrected resistance value of the resistor.

Practically, any conventional thermal flowmeter adopts such a system in which a heater-resistor (heat-generating element) generates a heat and a heat-sensing resistor (heat receiving element) disposed at a specified distance therefrom senses the transferred heat. The conventional flowmeter needs to use at least one pair of resistor elements (heat-generating element and heat-receiving element) which must be identical in size, specific heat and heat capacity, thereby it involves the following problems to be decided.

[1] Variations in resistance of a heat-generating element and a heat-receiving element:

(1) It is required to correctly adjust electric circuits to compensate a variation of temperature (i.e., resistance value) of the heat-generating element and the variations of temperature (i.e., resistance value) of the heat receiving element respectively;

(2) Regarding the temperature balance, i.e., resistance balance between the heat-generating element and the heat-receiving element, both elements are formed on a semiconductor substrate by using micro-machining technology of IC production and may be generally said to be combined with relatively high accuracy. However, the elements may be of no use if their resistance values are not sufficiently balanced. The conventional coil type thermal flowmeter may use a combination of a separate heating-generating element and a separate heat-receiving element, which are selected as well balanced in their resistance characteristics, thereby it may be manufactured with higher productivity than the thermal flowmeter having the elements integrally formed on a substrate;

(3) It is difficult to arrange the heat-generating element and the heat-receiving element at the optimal positions and at an optimal distance. The elements are also limited by an attainable accuracy;

(4) Since there is a distance between the heat-generating element and the heat-receiving element, it is impossible to correctly detect a difference of resistance values for a very small flow-rate of fluid;

(5) Both the heat-generating element and the heat-receiving element shall have a high accuracy of temperature distribution. Any dispersion of the temperature distribution may affect a detection output signal and makes it necessary to additionally adjust each respective sensor circuit;

(6) Increasing the number of the heat-generating and heat-receiving elements increases the size of the substrate and the number of its output leads. When the substrate of an increased size is disposed in a stream of fluid to be measured, it may prevent the fluid from freely flowing and can not obtain the correct measurement result. This also leads to increase of the manufacturing cost of the product. The accuracy of sensing a small flow rate is also reduced;

(7) The increased number of heat generating and receiving elements increases the electric power consumption;

(8) The vertical arrangement of the heat-receiving element at the upper position and the heat-generating element at the lower position in a vertically upward stream of gas may be encountered with such a problem that even with no flow of fluid to be sensed, the heat-receiving element generates an output signal, sensing an ascending current of air heated by the heat-generating element. This means that thus constructed flowmeter shall be mounted with special consideration of its mounting conditions and has a limitation of its mounting places.

[2] Regarding compensation for an ambient temperature when detecting a gas flow:

(1) In a flowmeter, wherein a set of three micro-bridge-like elements (resistances) disposed at top, center and last positions from the upstream side in gas passage is used to detect a temperature of the gas flow by the top element and a flow-rate of the gas by the center heat-generating element and the last heat-receiving element and to compensate the measured flow rate for variation of temperature according to the information obtained by the top element, the drawbacks (1) to (8) described above in item [1] regarding the variations of resistance values of the heat-generating element and the heat-receiving elements become more serious;

(2) A flowmeter, wherein a pattern of a resistor for sensing an ambient temperature is formed on a semiconductor substrate, can not serve to correctly detect a flow rate because its resistance value slowly responses and changes with a change of temperature of the semiconductor substrate having a large heat capacity, thereby the correct temperature of the gas at the moment of its flow-rate measurement can not be detected.

SUMMARY OF THE INVENTION

It is therefore a primary object of the present invention to provide a temperature-compensating type atmosphere measuring device which is capable of accurately detecting an ambient atmosphere by detecting the atmosphere and its temperature by the use of a single element, thereby eliminating the variation problem arisen in case of using two separate elements.

Another object of the present invention is to provide an atomosphere measuring method using a single-element sensor which is capable of detecting both ambient atmosphere and atmosphere temperature, thereby eliminating a measurement error problem arising in two-element sensor system and attaining the higher mass productivity of the elements with an increased product yield.

Another object of the present invention is to provide a single-element (resistor) sensor which is capable of measuring a gas flow by heating the single element with a small current and a subsequent large current and which, being free from problems of two-element type sensor in regard with variations of resistance values and temperature rising of two elements, has an increased production yield and an improved mass productivity in comparison with the prior two-element sensor.

Another object of the present invention is to provide a flow measuring method using a single-element sensor which is capable of measuring a gas flow by a single sensing element which is free from affection of an unevenness of ambient temperature distribution and turbulent of gas to be measured to attain high accurate flow measurements.

BRIEF DESCRIPTION OF DRAWINGS

FIGS. 2A to 2C are views for explaining production of a measurement error due to a response delay of a conventional hygrometer.

FIG. 3 is a construction view of another conventional hygrometer.

FIGS. $6A_1$ to $6D_1$ are views for explaining the principle of a hygrometer being as an embodiment of an atmosphere measuring device according to the present invention.

Figure 7A:
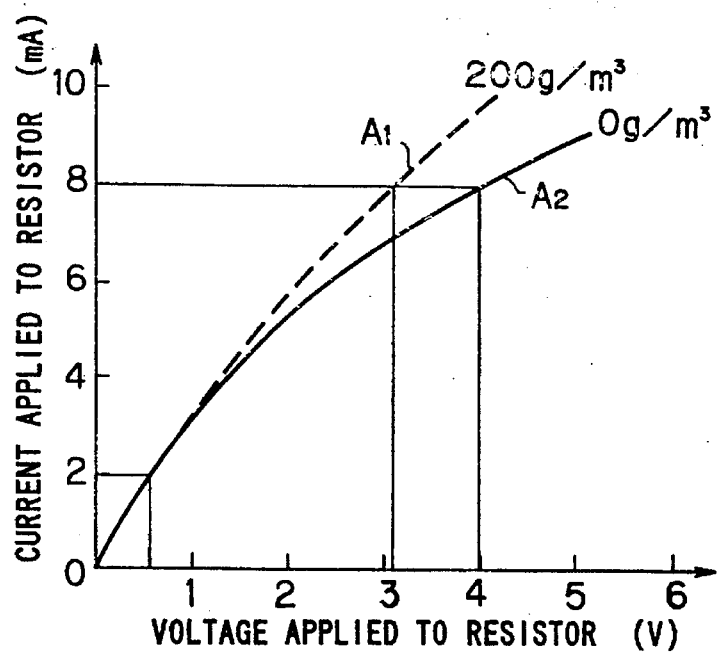
Figure 7B:
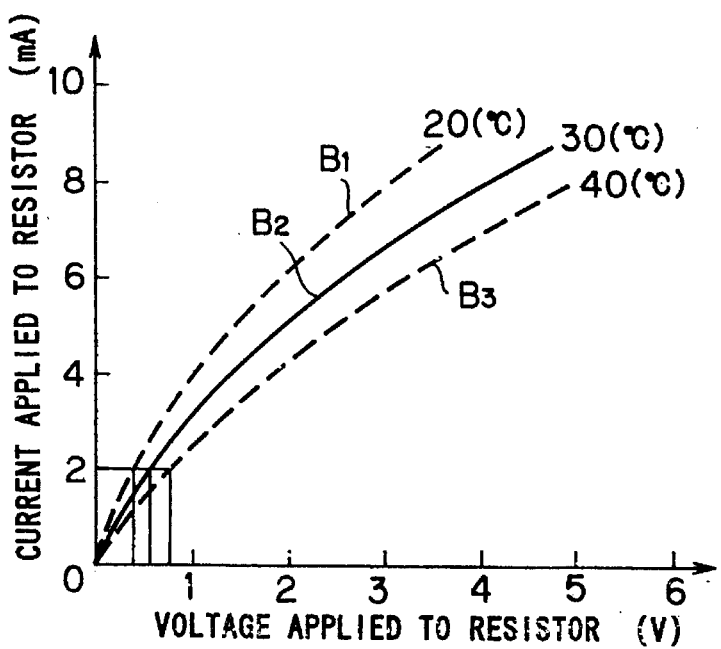

FIGS. 7A and 7B are volt-ampere characteristic curves of a humidity sensing element.

FIGS. $8A_1$ to 8D are views for explaining a method of driving a humidity sensing element of a hygrometer that is an embodiment of an atmosphere measuring device according to the present invention.

Figure 9A:
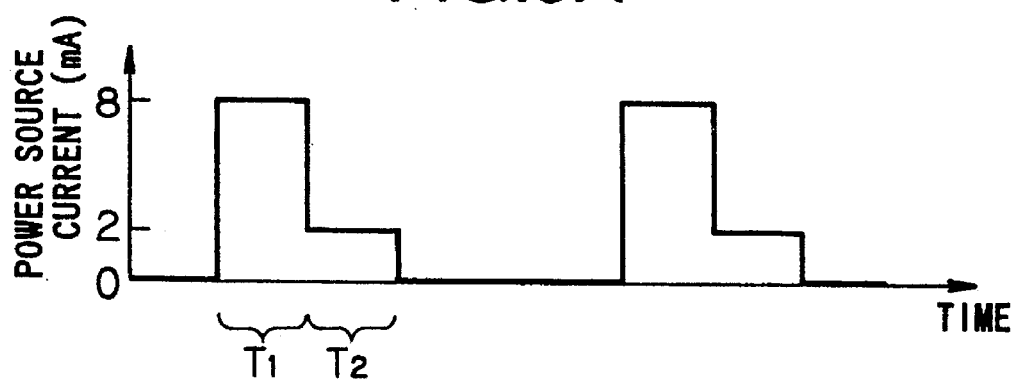
Figure 9B:
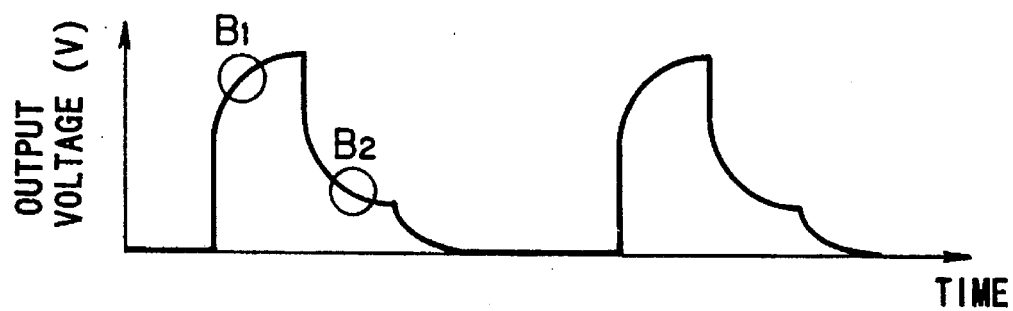

FIGS. 9A and 9B show waveforms of a current pulse and an output voltage pulse when driving a sensor with a large current pulse and a subsequent small current pulse.

FIGS. 10A to 10D are diagrams for explaining a relationship between a change of ambient condition and output characteristic of a hygrometer that is an embodiment of an atmosphere measuring device according to the present invention.

Figure 11:
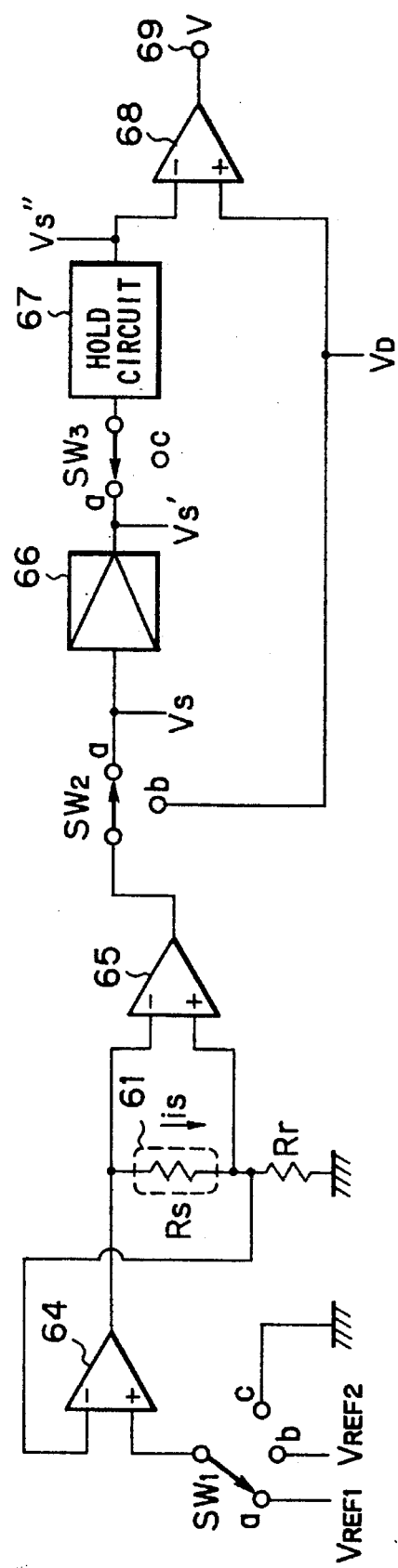

FIG. 11 is an electrical circuit diagram showing an example of a driving circuit of a hygrometer that is an embodiment of an atmosphere measuring device according to the present invention.

FIGS. 12A to 12H show waveforms of signals in components of the driving circuit shown in FIG. 11.

Figure 13:
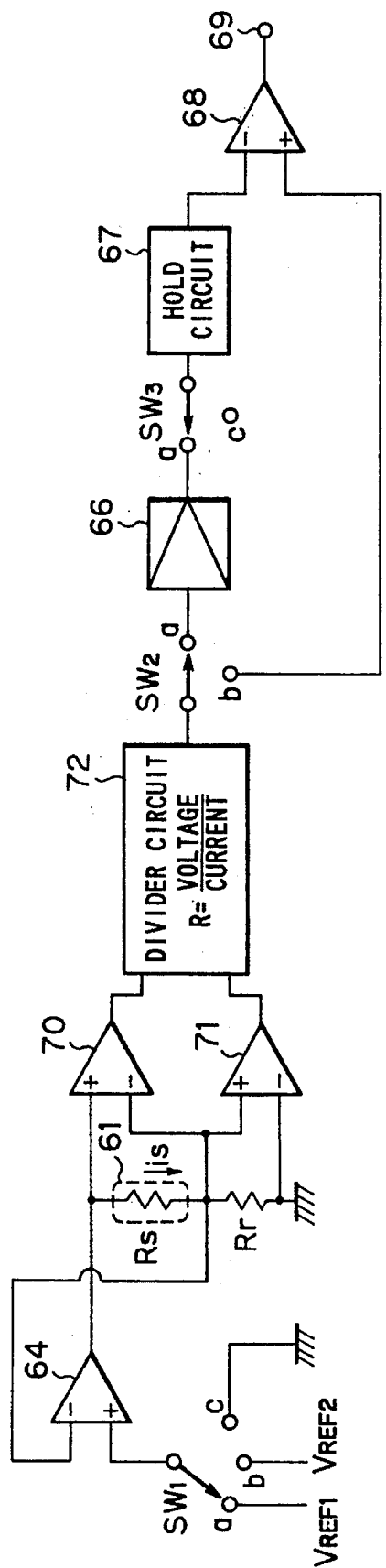

FIG. 13 is an electrical circuit showing another example of a driving circuit of a hygrometer that is an embodiment of an atmosphere measuring device according to the present invention.

Figure 14A:
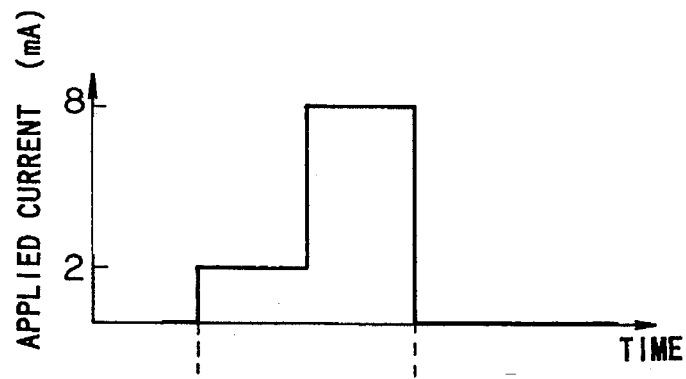
Figure 14B:
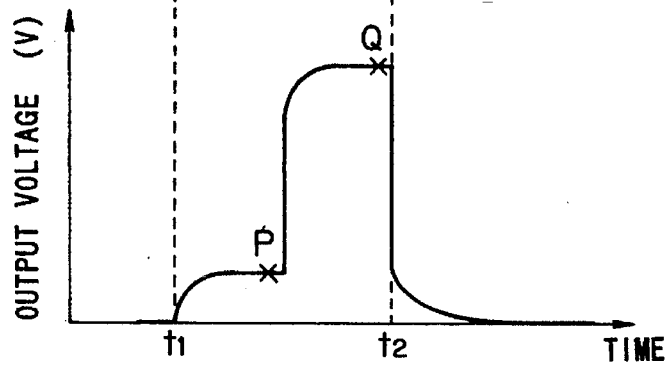

FIGS. 14A and 14B show a two-power-source driving system relating to the present invention.

Figure 15A:
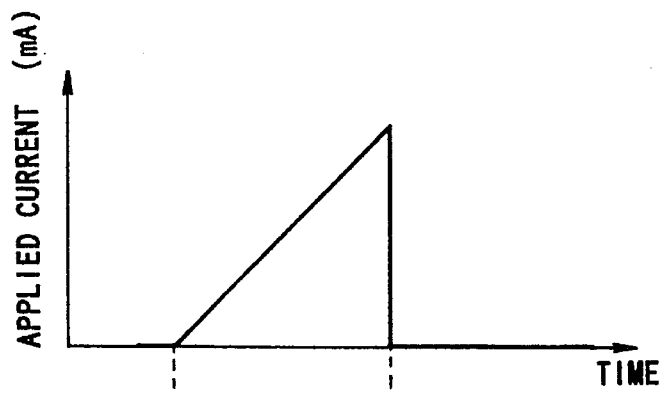
Figure 15B:
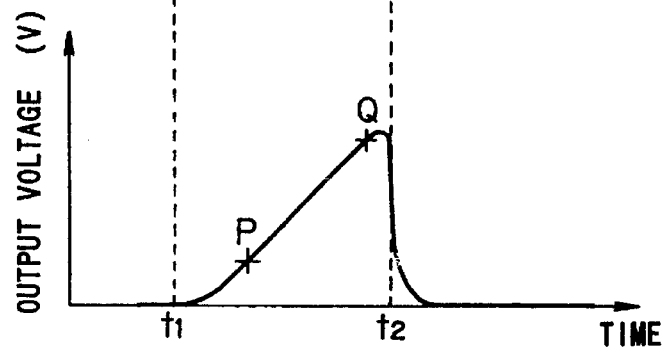

FIGS. 15A and 15B show an example of driving current waveform and output voltage waveform of a hygrometer that is an embodiment of an atmosphere measuring device according to the present invention.

FIGS. 16A and 16B show another driving current waveforms of a hygrometer that is an embodiment of an atmosphere measuring device according to the present invention.

FIGS. 17A to 17E shows a timing chart for explaining the operation of a driving circuit of a hygrometer that is an embodiment of an atmosphere measuring device according to the present invention.

Figure 18:
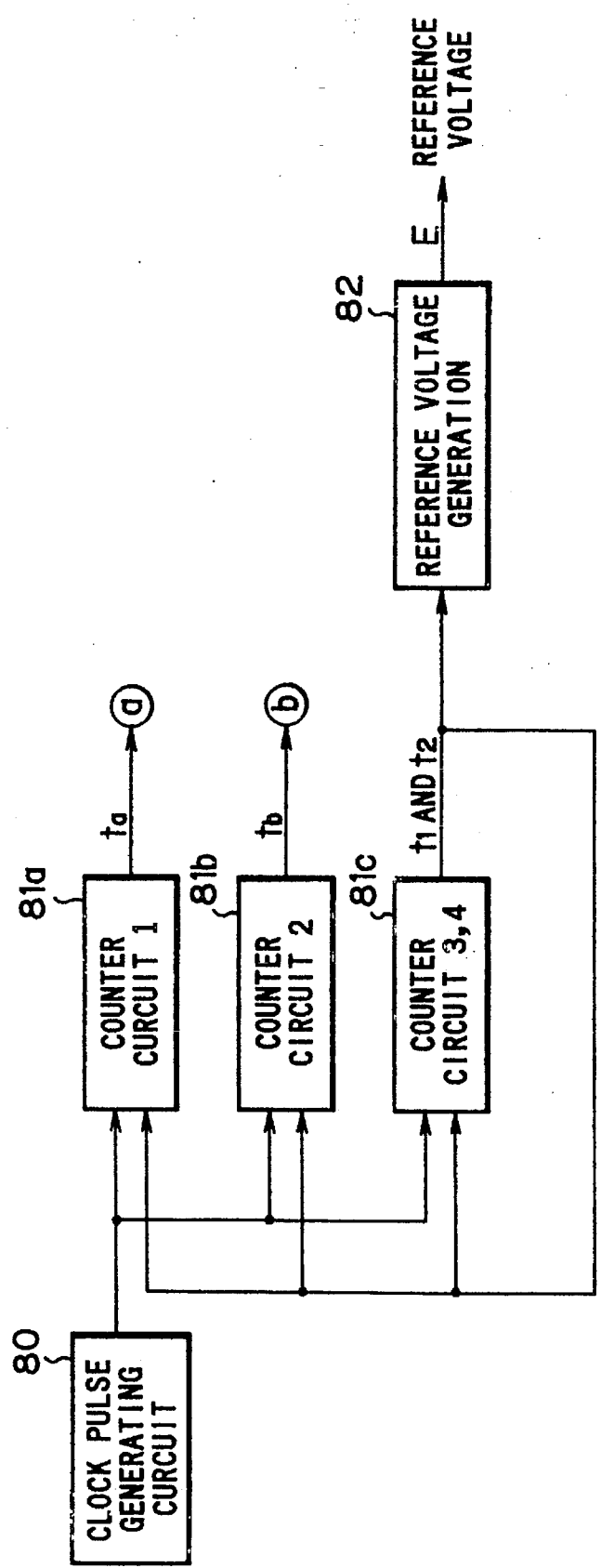

FIG. 18 is an electrical circuit diagram showing an example of timing generation method according to the present invention.

FIG. 19 shows an example of a reset circuit.

FIGS. 20A to 20D show a time chart of the reset circuit shown in FIG. 19.

Figure 21:
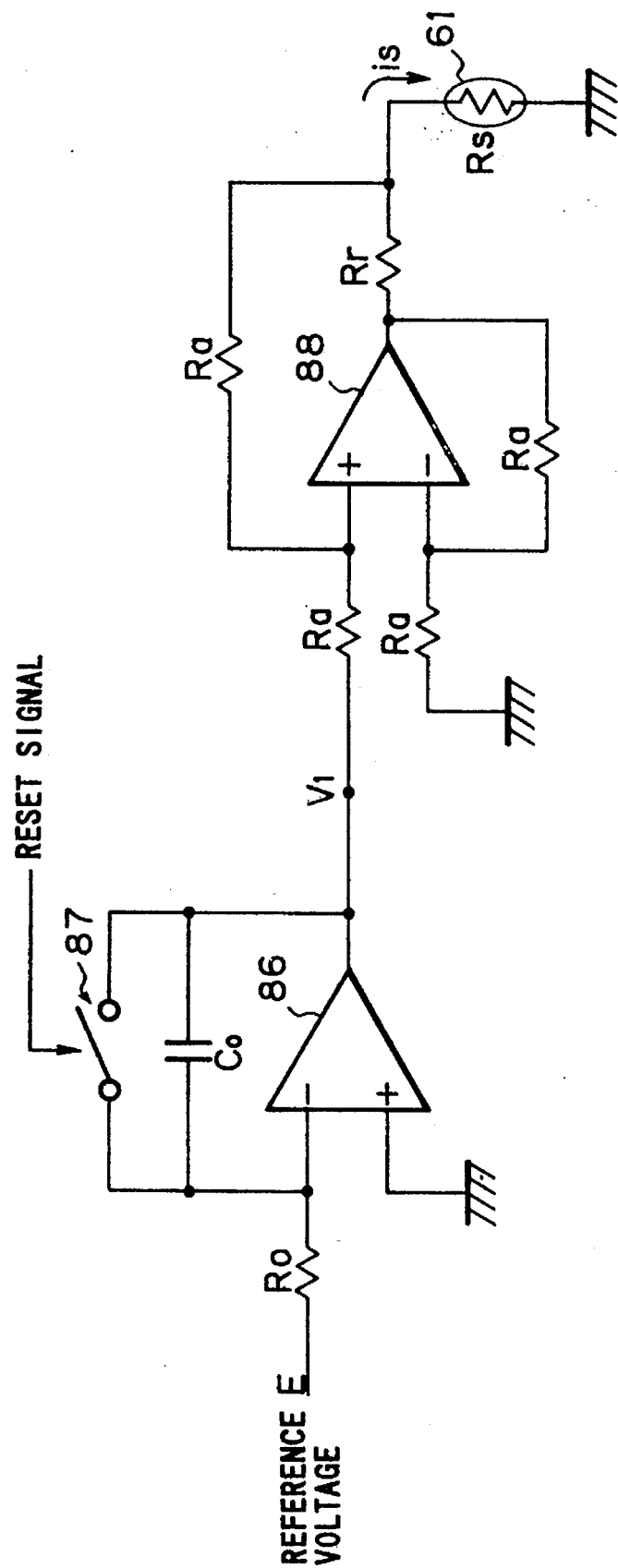

FIG. 21 is an electrical circuit diagram of a saw-tooth current driving circuit of a sensing element according to the present invention.

Figure 22:
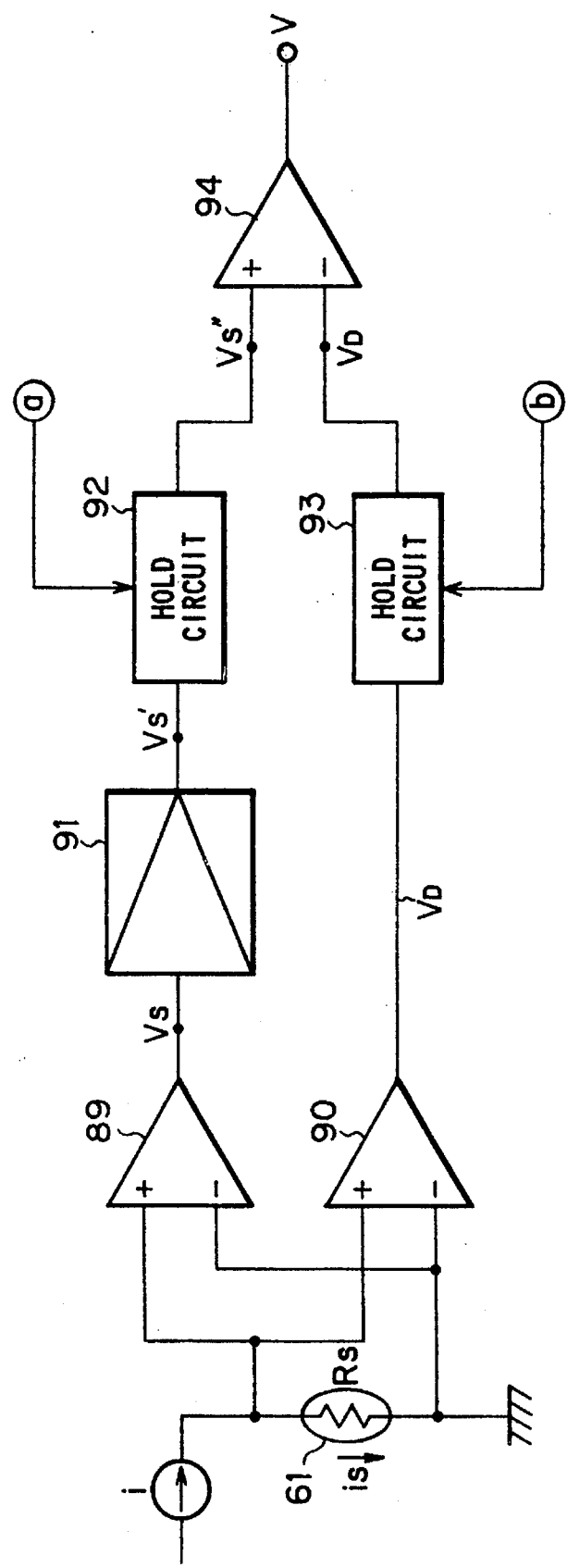

FIG. 22 is an electrical circuit diagram for explaining an example of a humidity measuring circuit driven by a saw-tooth current drive of a sensing element according to the present invention.

Figure 23:
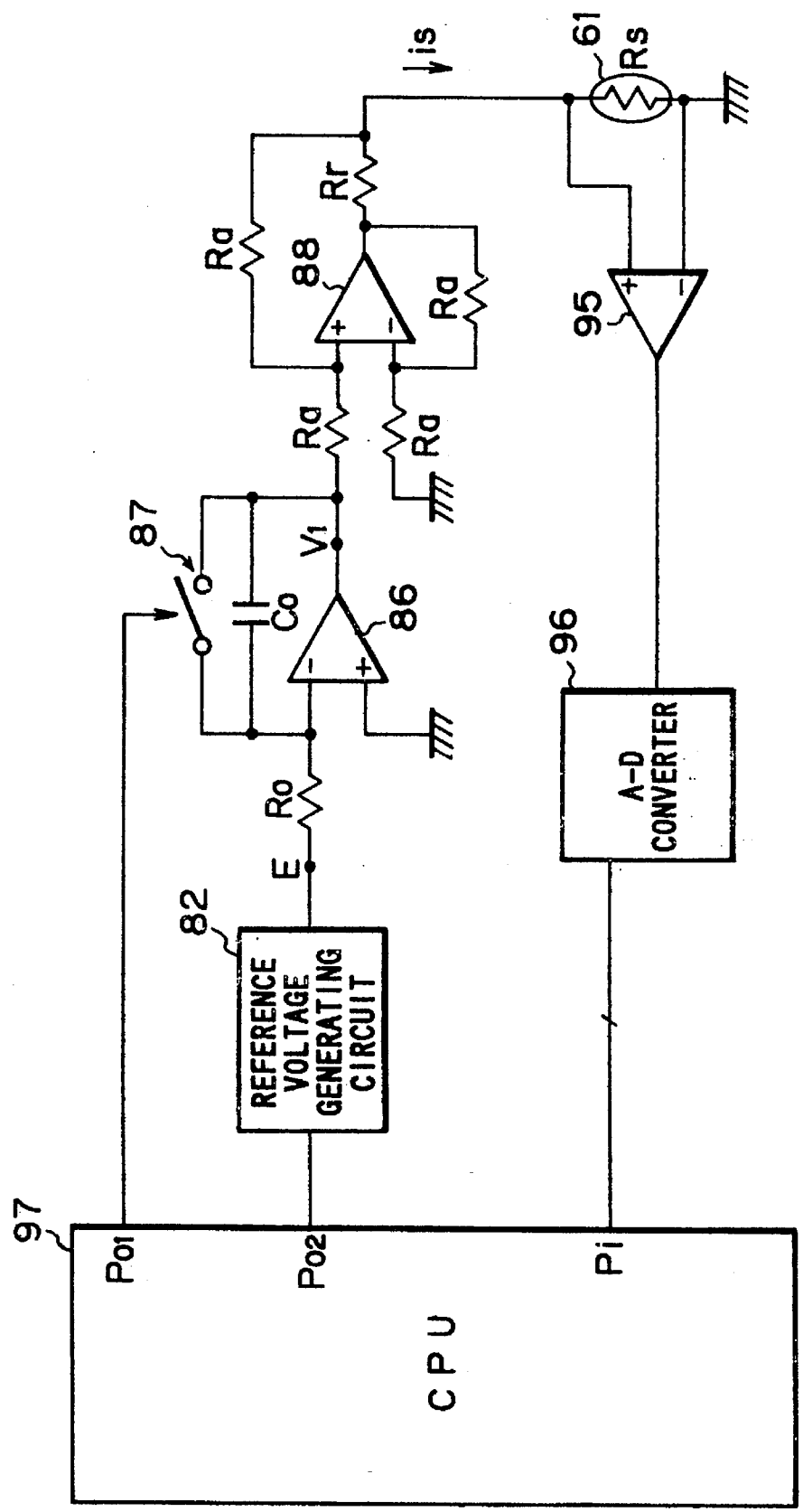

FIG. 23 is an electrical circuit diagram for explaining another example of a humidity output circuit driven by a saw-tooth current drive of a sensing element according to the present invention.

Figure 24:
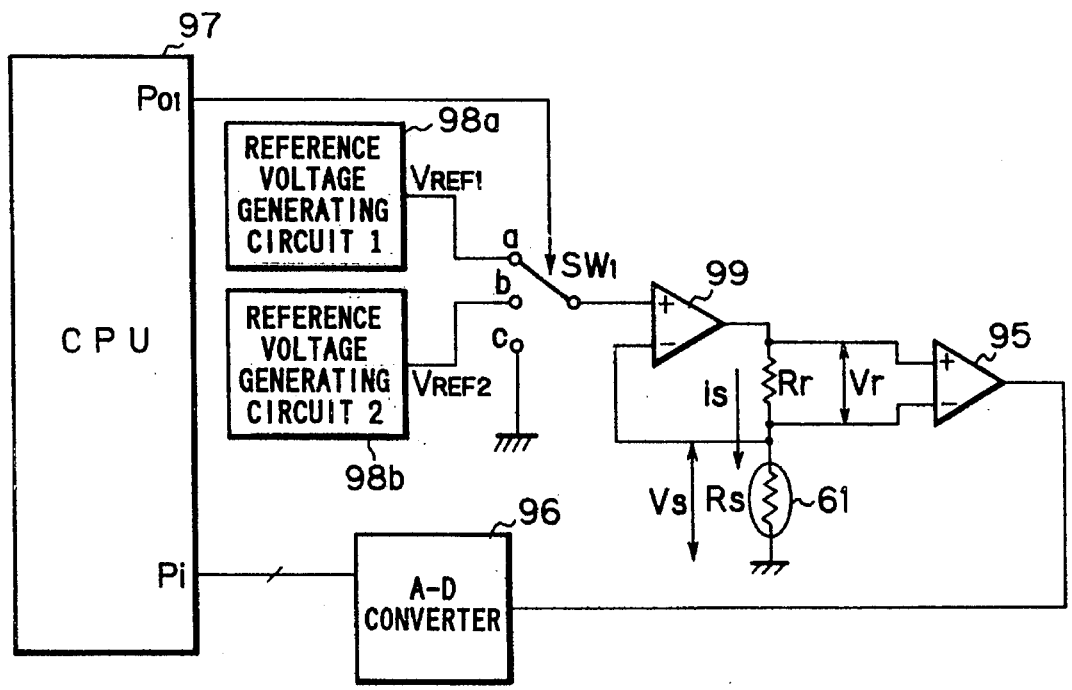

FIG. 24 is an electrical circuit for explaining an example of a humidity measuring circuit using a sensing element according to the present invention.

Figure 25:
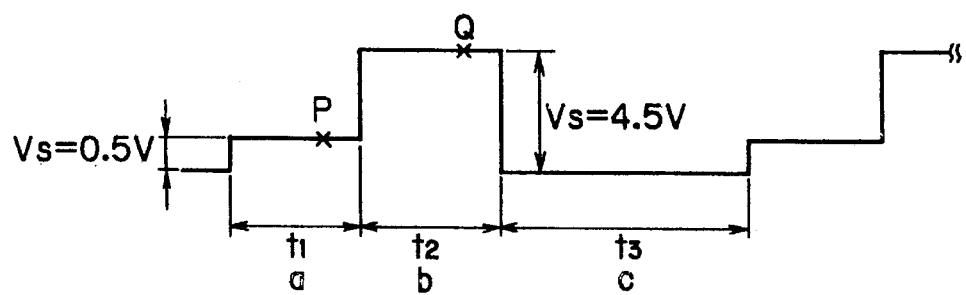

FIG. 25 is a time chart for explaining the operation of the circuit shown in FIG. 24.

FIG. 26 is a perspective view for explaining another example of a humidity (moisture) sensor of a hygrometer that is an embodiment of an atmosphere measuring device according to the present invention.

FIGS. 27A to 27D show a time chart for determining a humidity by the humidity sensor of FIG. 26.

FIGS. 28A to 28C show another time chart for determining a humidity by the humidity sensor of FIG. 26.

Figure 29A:
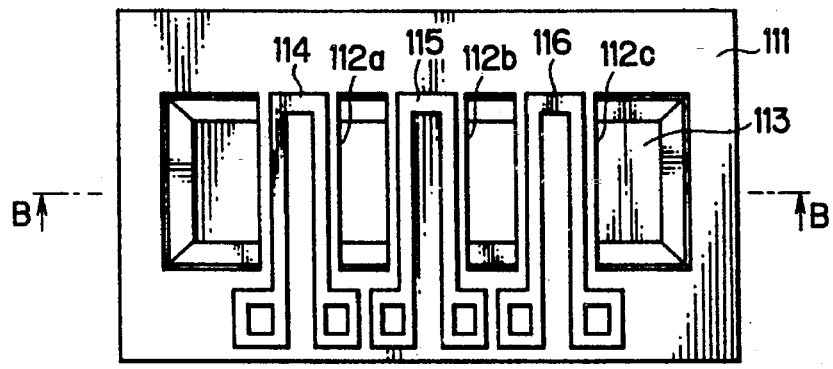
Figure 29B:
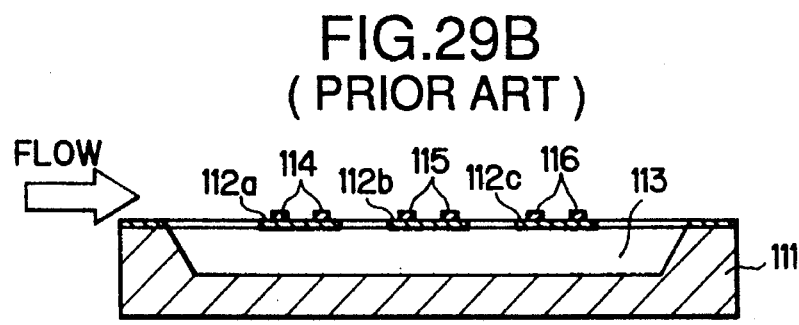

FIGS. 29A and 29B are partially sectional construction views of a conventional flow meter.

Figure 30:
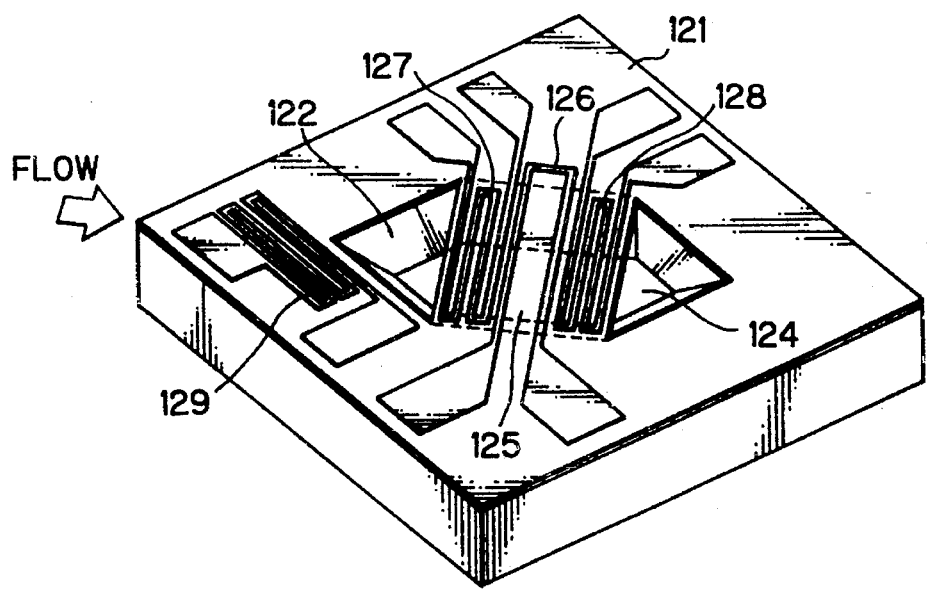

FIG. 30 is a view of another conventional flow meter.

Figure 31A:
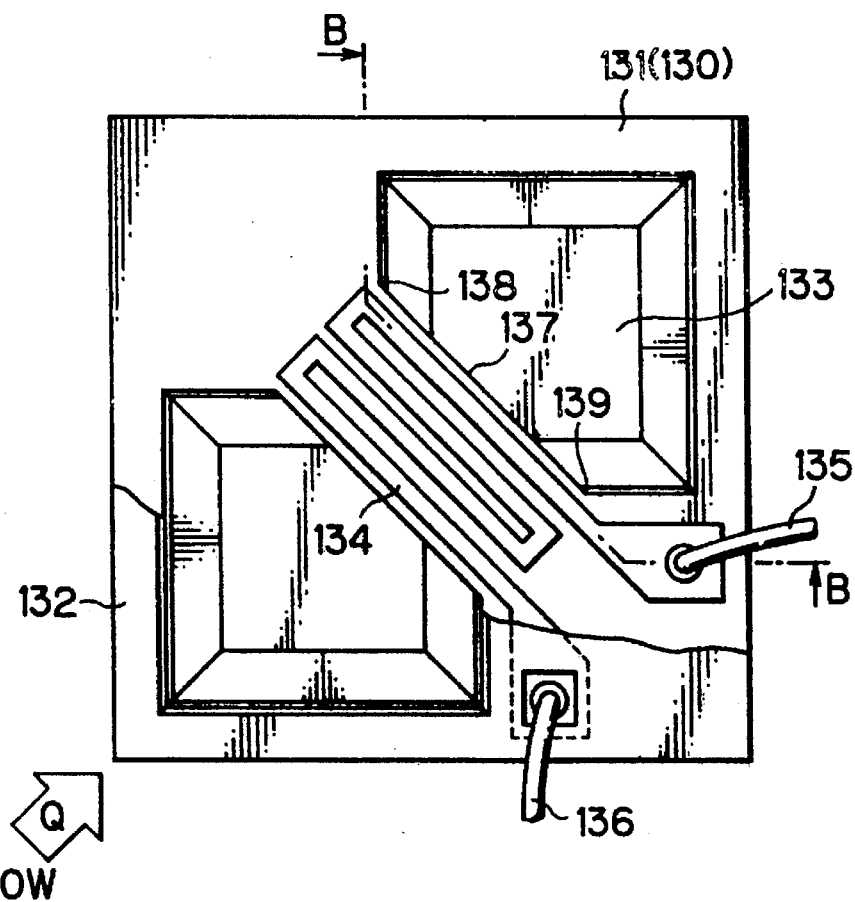
Figure 31B:
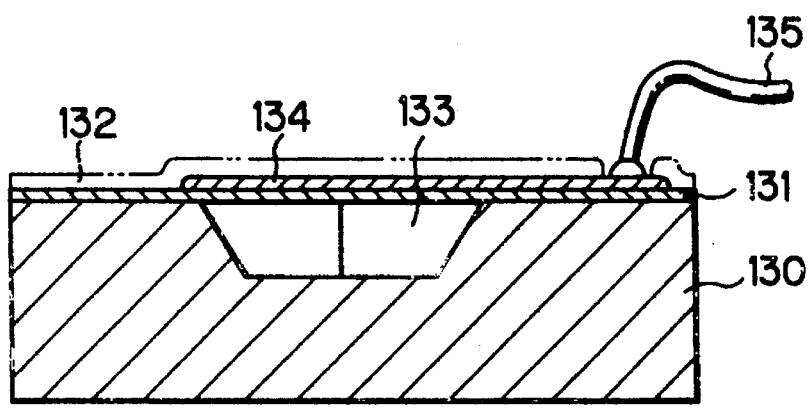

FIGS. 31A and 31B are construction views for explaining an example of a flow sensor according to the present invention.

Figure 32A:
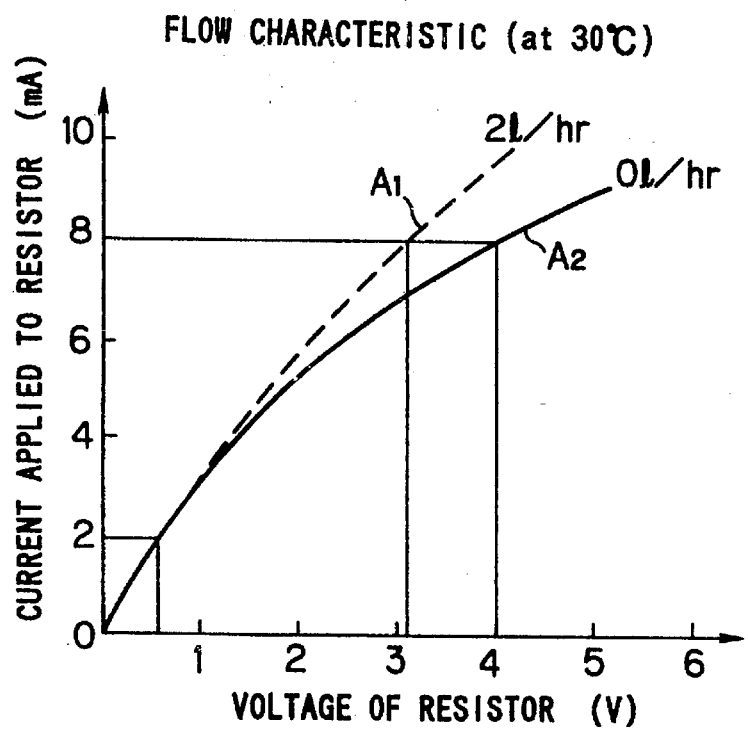
Figure 32B:
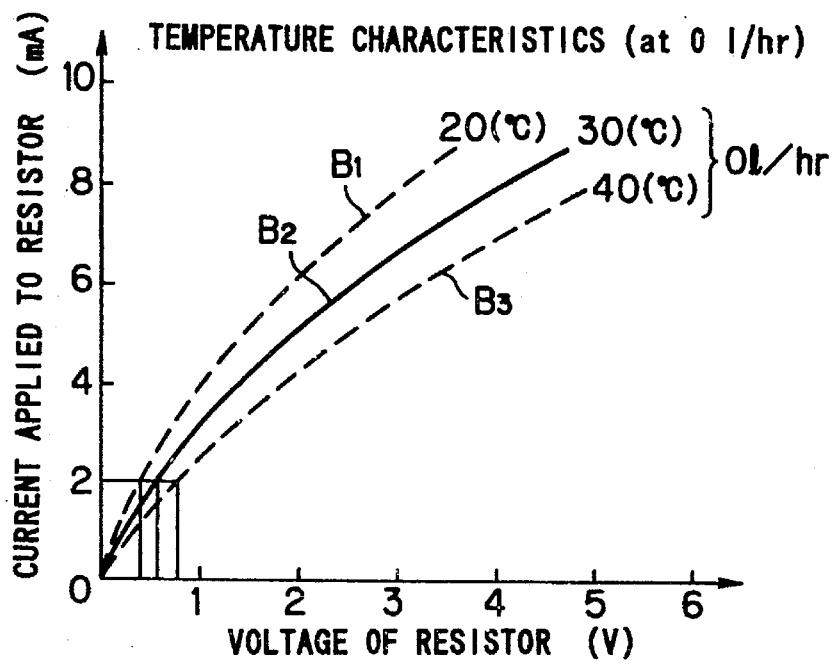

FIGS. 32A and 32B are views for explaining principle of the operation of a flow sensor according to the present invention.

FIGS. 33A and 33B are construction views for explaining another example of a flow sensor according to the present invention.

Figure 34A:
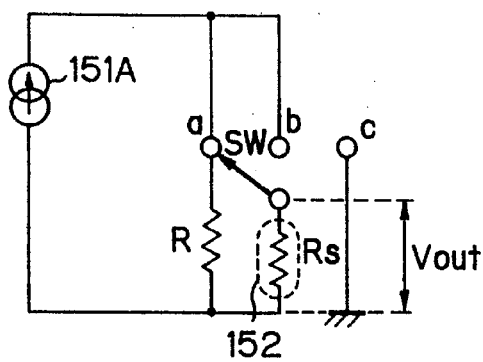
Figure 34B:
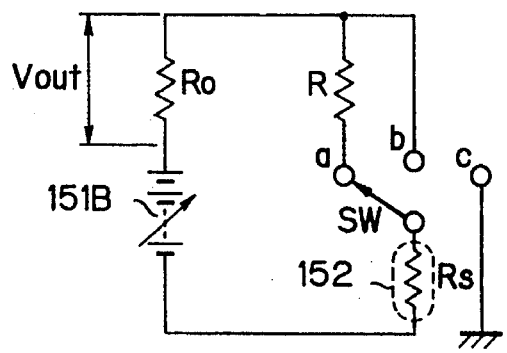

FIGS. 34A and 34B are views for explaining example of driving circuits of a flow sensor according to the present invention.

Figure 35A:
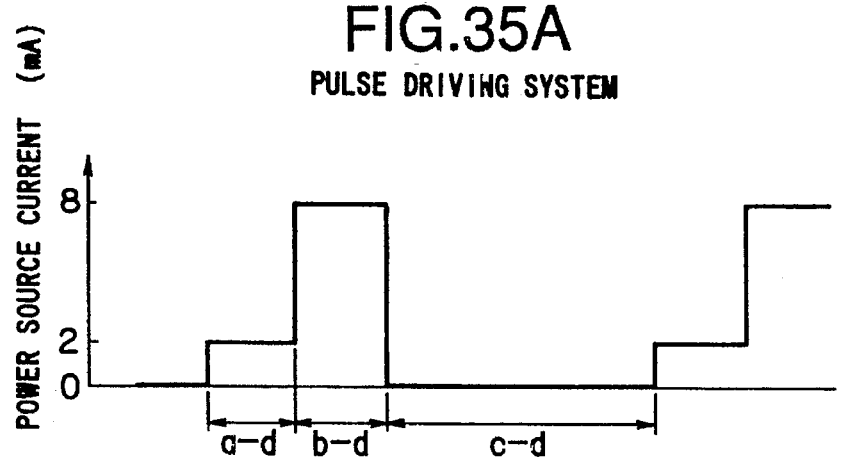
Figure 35B:
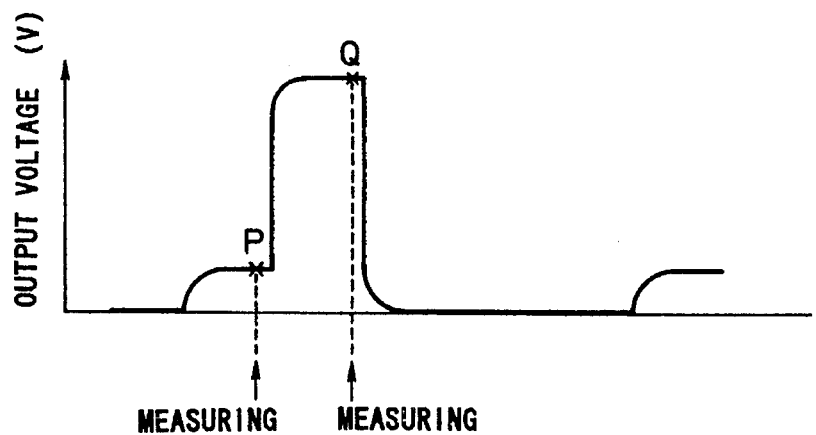

FIGS. 35A and 35B are views for explaining example of a driving current waveform and an output voltage waveform of a flow sensor according to the present invention.

FIGS. 36A to 36D are diagrams for explaining a relationship between a change of ambient condition and output characteristic of a flow meter that is an embodiment of the present invention.

Figure 37A:
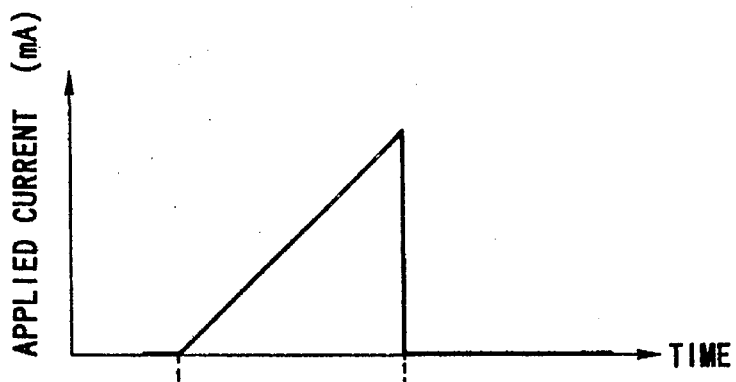
Figure 37B:
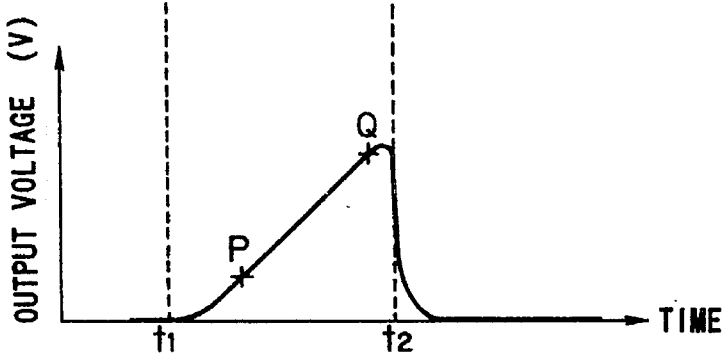

FIGS. 37A and 37B show other example of driving current waveforms and out put voltage waveforms of a flow sensor according to the present invention.

Figure 38A:
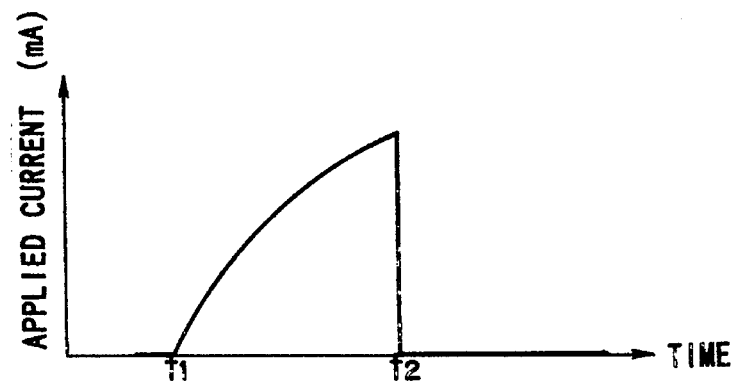
Figure 38B:
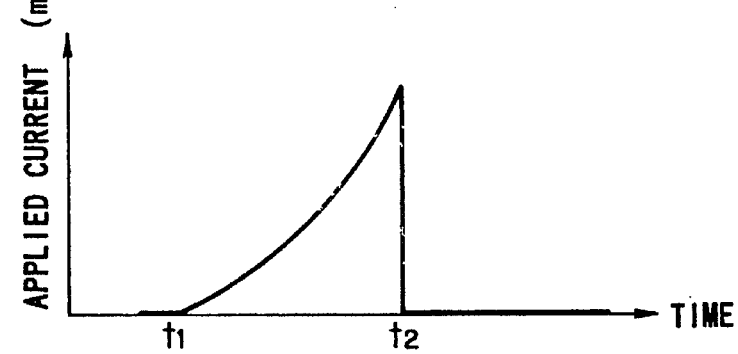

FIGS. 38A and 38B show other examples of driving current waveforms of a flow sensor according to the present invention.

Figure 39:
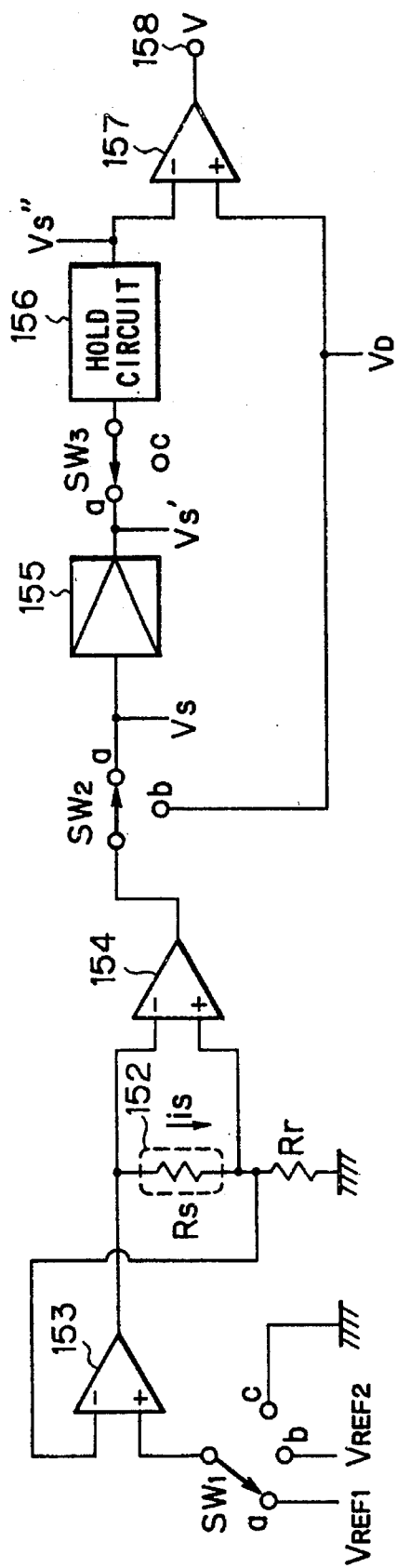

FIG. 39 is an electrical circuit diagram of a driving circuit for explaining an example of a flow meter according to the present invention.

FIGS. 40A to 40H are views showing waveforms of portions of the driving circuit of FIG. 39.

Figure 41:
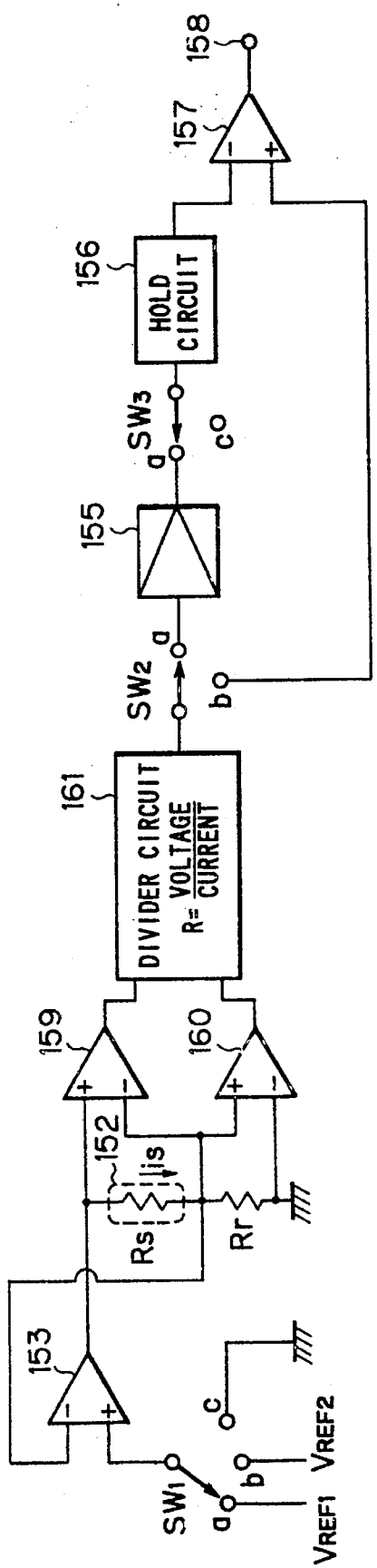

FIG. 41 is an electrical circuit diagram of a driving circuit for explaining an example of a flow meter according to the present invention.

FIGS. 42A to 42E are timing charts for explaining measurement timing of a flow meter according to the present invention.

Figure 42:
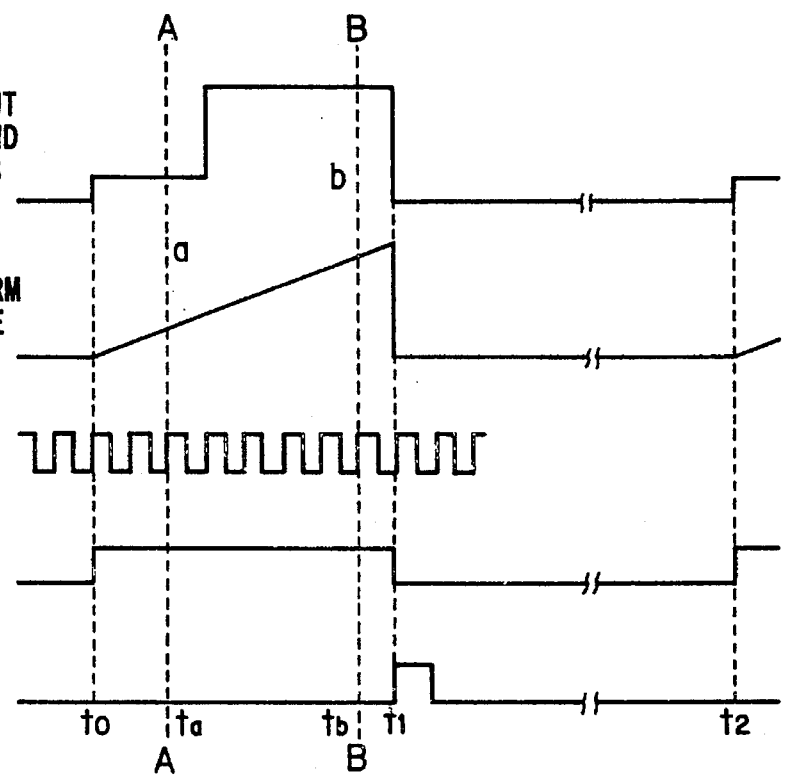
Figure 43:
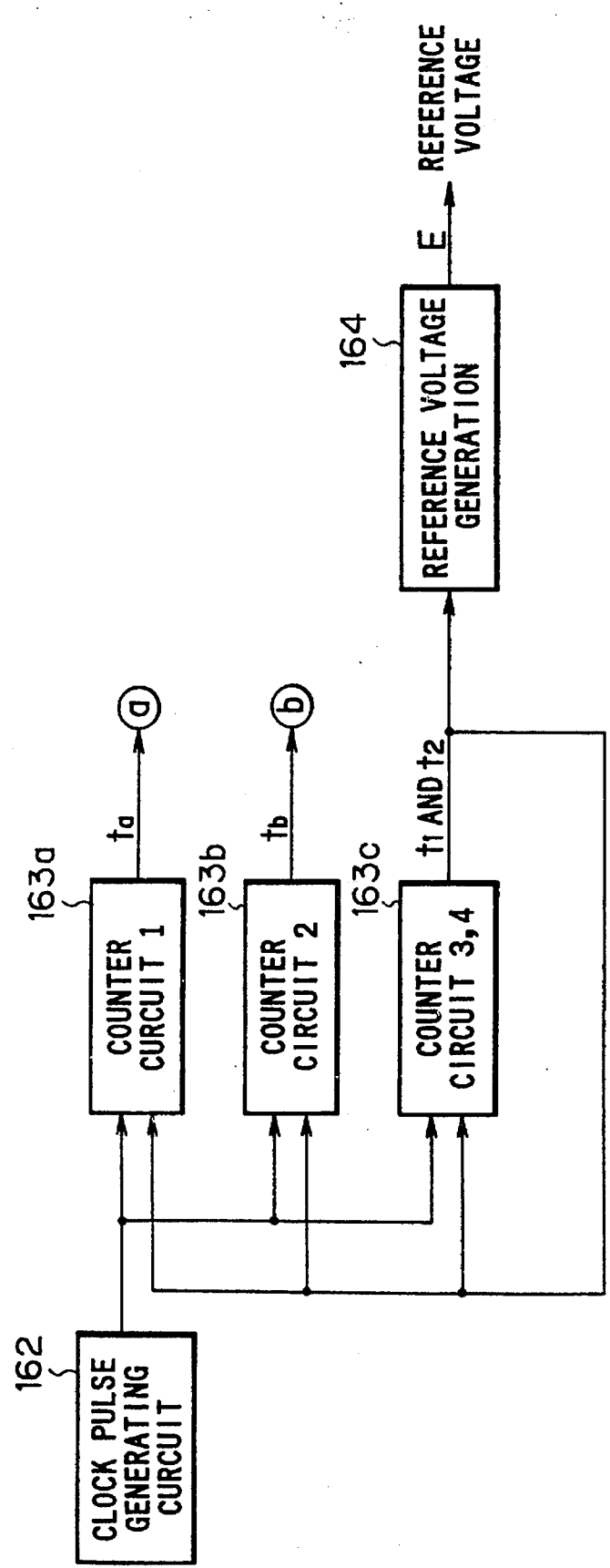

FIG. 43 is an electrical circuit diagram showing an example of an electric circuit for performing the measurement timing shown FIGS. 42A to 42E.

FIG. 44 shows an example of a reset circuit suitable to the circuit of FIG. 43.

FIGS. 45A to 45D are time charts for explaining the reset circuit shown in FIG. 44.

Figure 46:
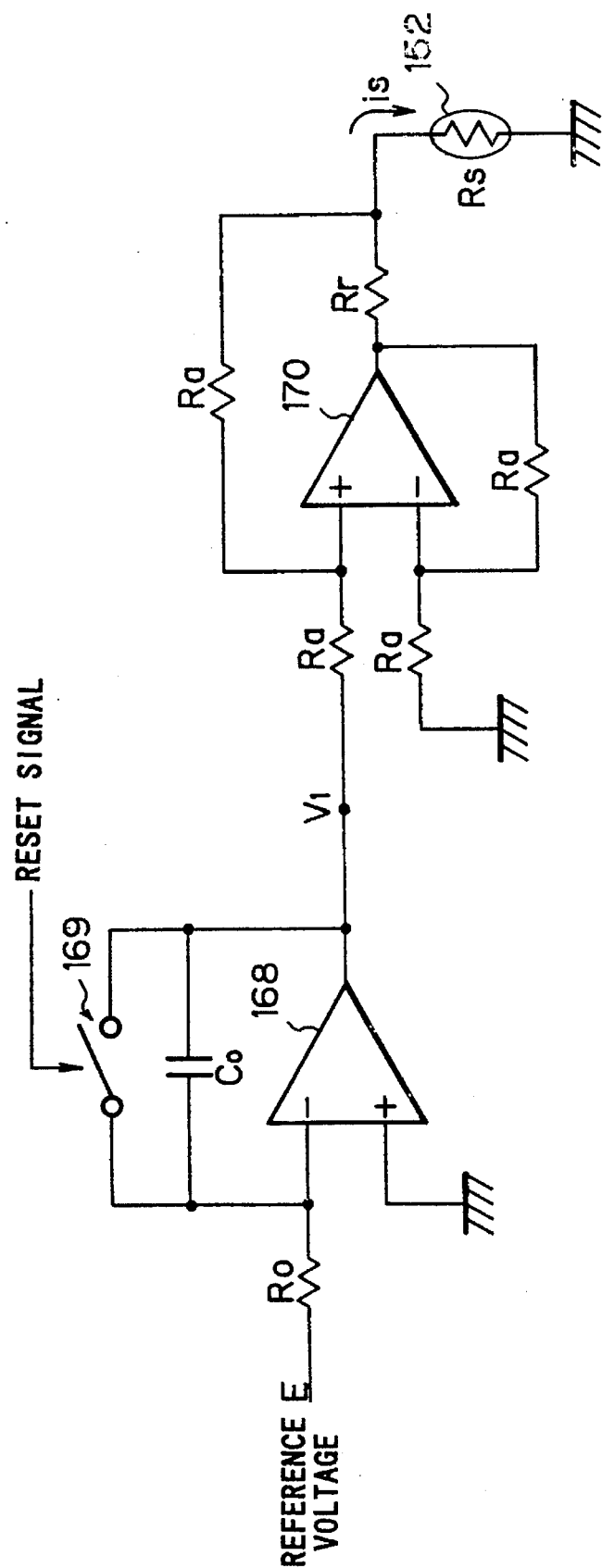

FIG. 46 is an electrical circuit diagram showing an example of a saw-tooth current driving circuit of a sensing element relating to the present invention.

Figure 47:
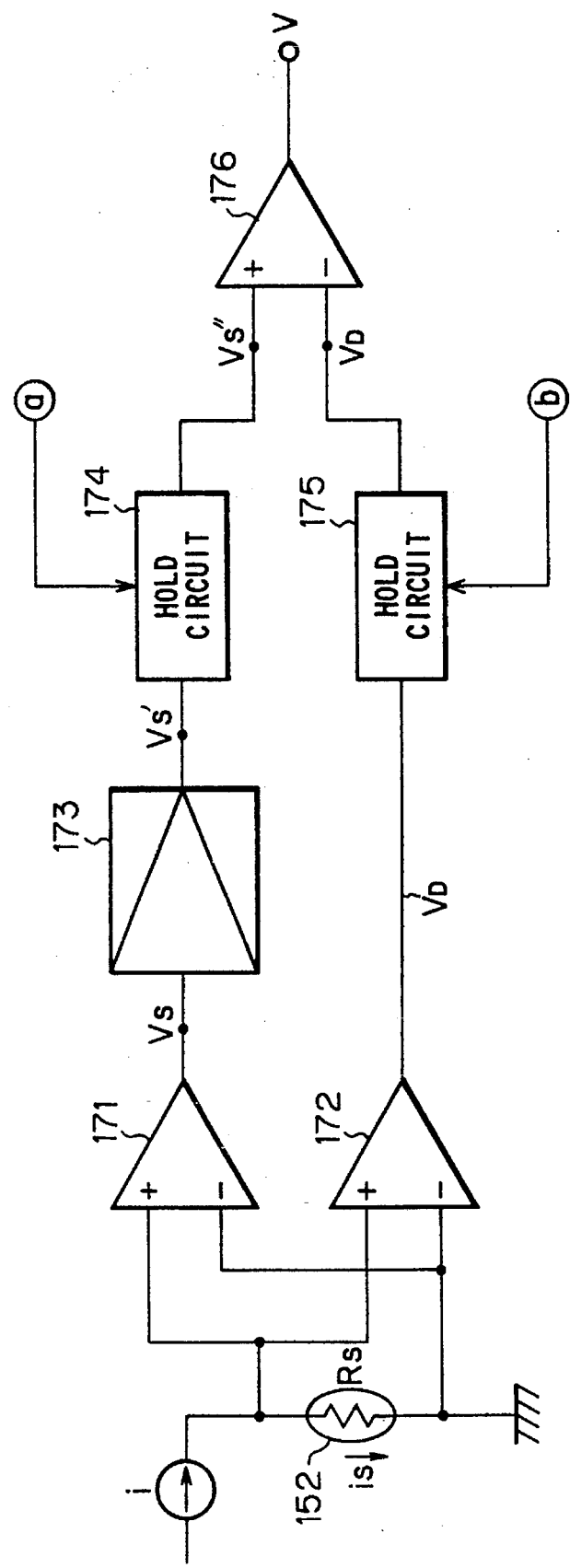

FIG. 47 is an electrical circuit diagram for explaining an example of a flow meter in case when a saw-tooth current drives a sensing element relating to the present invention.

Figure 48:
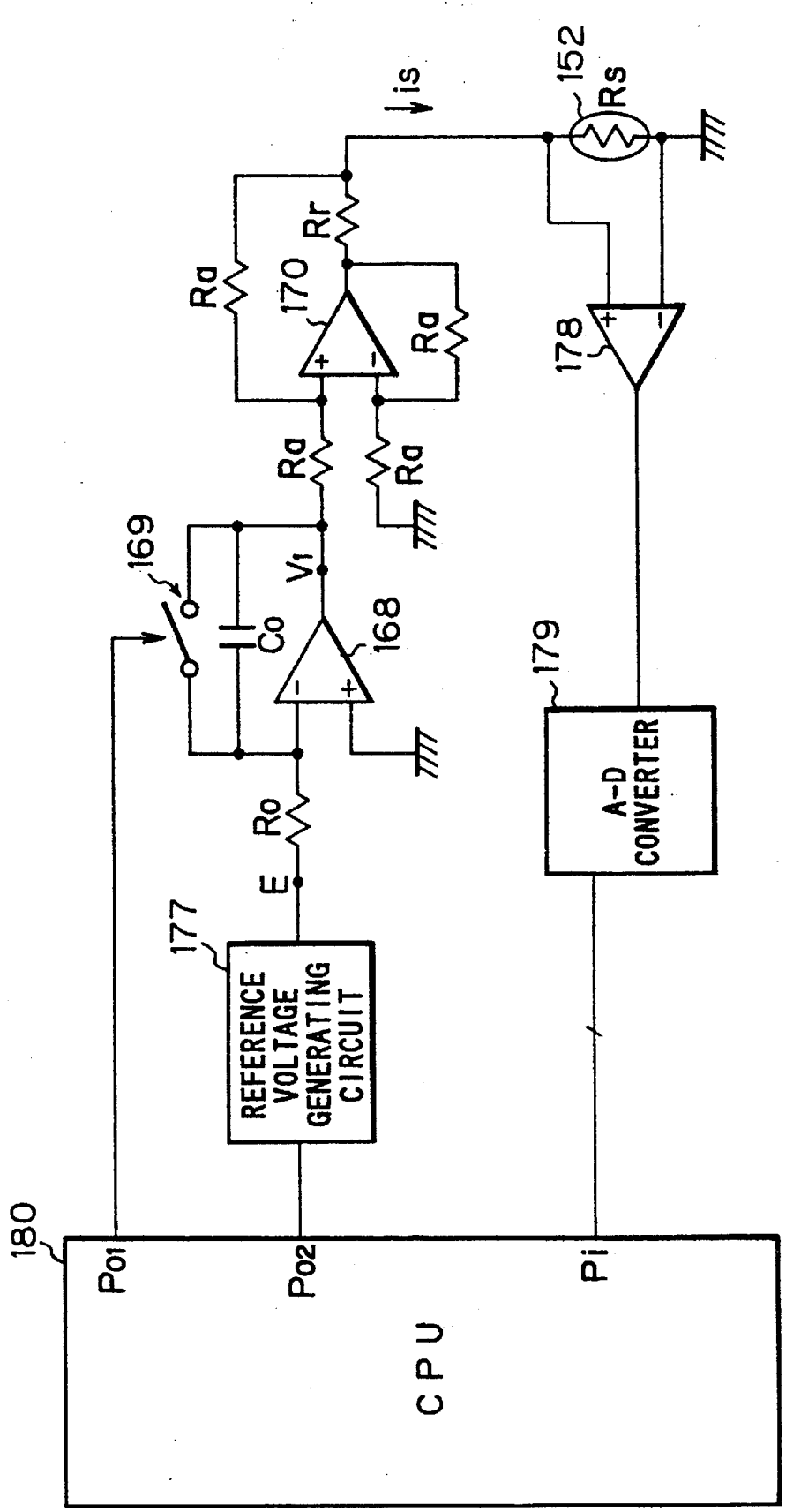

FIG. 48 is an electrical circuit diagram for explaining another example of a flow meter in case when a saw-tooth current drives a sensing element relating to the present invention.

Figure 49:
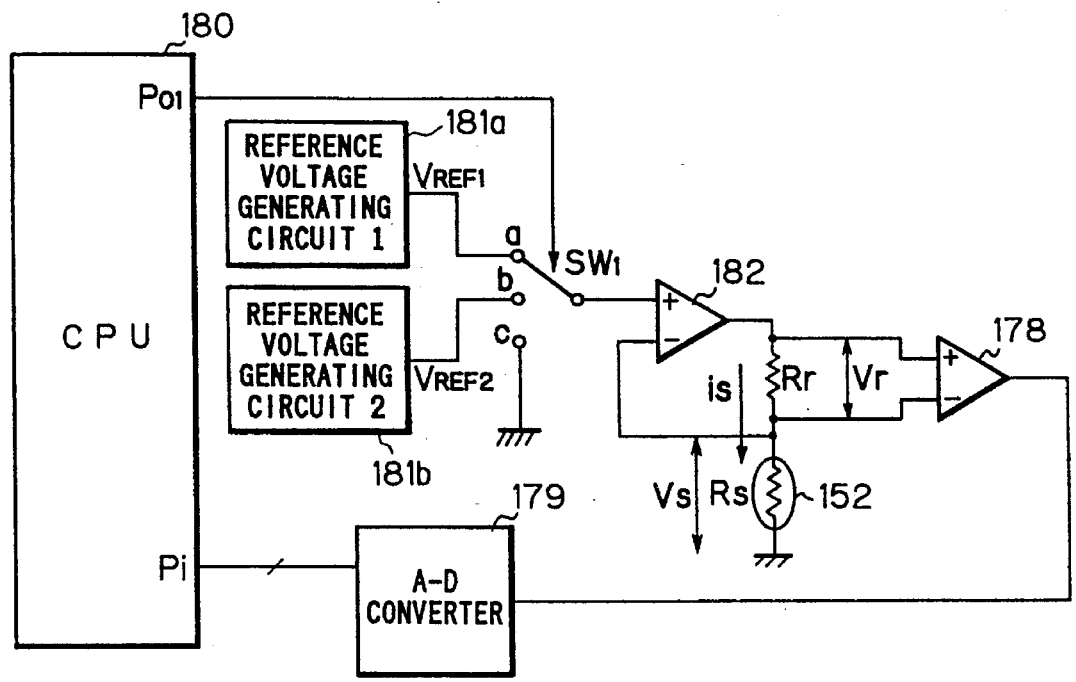

FIG. 49 is an electrical circuit diagram for explaining an example of a flow output circuit in case when a voltage pulse drives a sensing element relating to the present invention.

Figure 50:
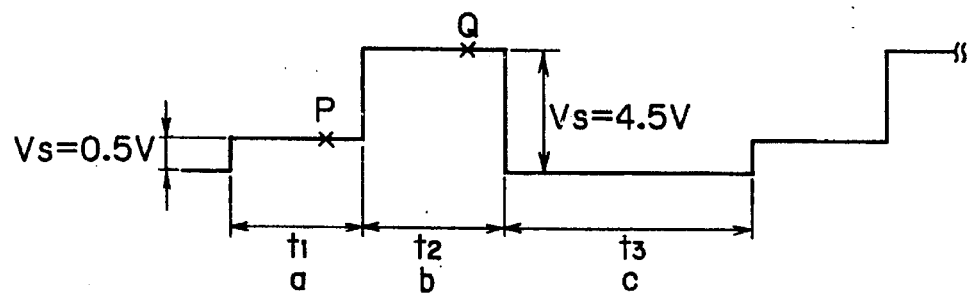

FIG. 50 shows an example of a time chart for explaining the circuit operation of FIG. 49.

Figure 51:
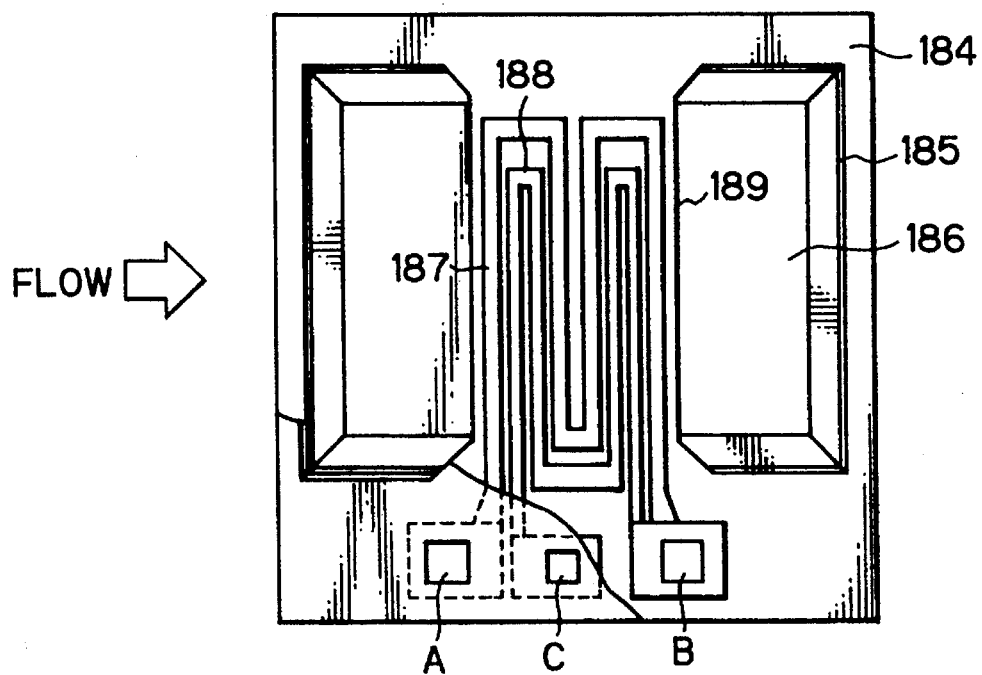

FIG. 51 is a plan view for explaining another example of a flow sensor according to the present invention.

Figure 52:
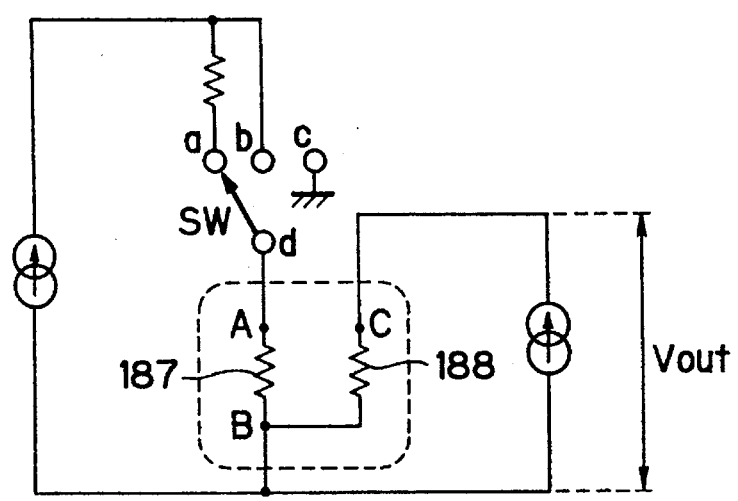

FIG. 52 is an electrical circuit for explaining a method of flow measurement by the flow sensor shown in FIG. 51.

FIG. 53 is a perspective view for explaining another example of a flow meter according to the present invention.

FIGS. 54A to 54D are time charts of flow measurements using flow meters of FIGS. 51 and 53.

FIGS. 55A to 55C are another example of a time chart of flow measurement using flow meters shown in FIGS. 51 and 53.

DESCRIPTION OF THE PREFERRED EMBODIMENTS

Figure 1:
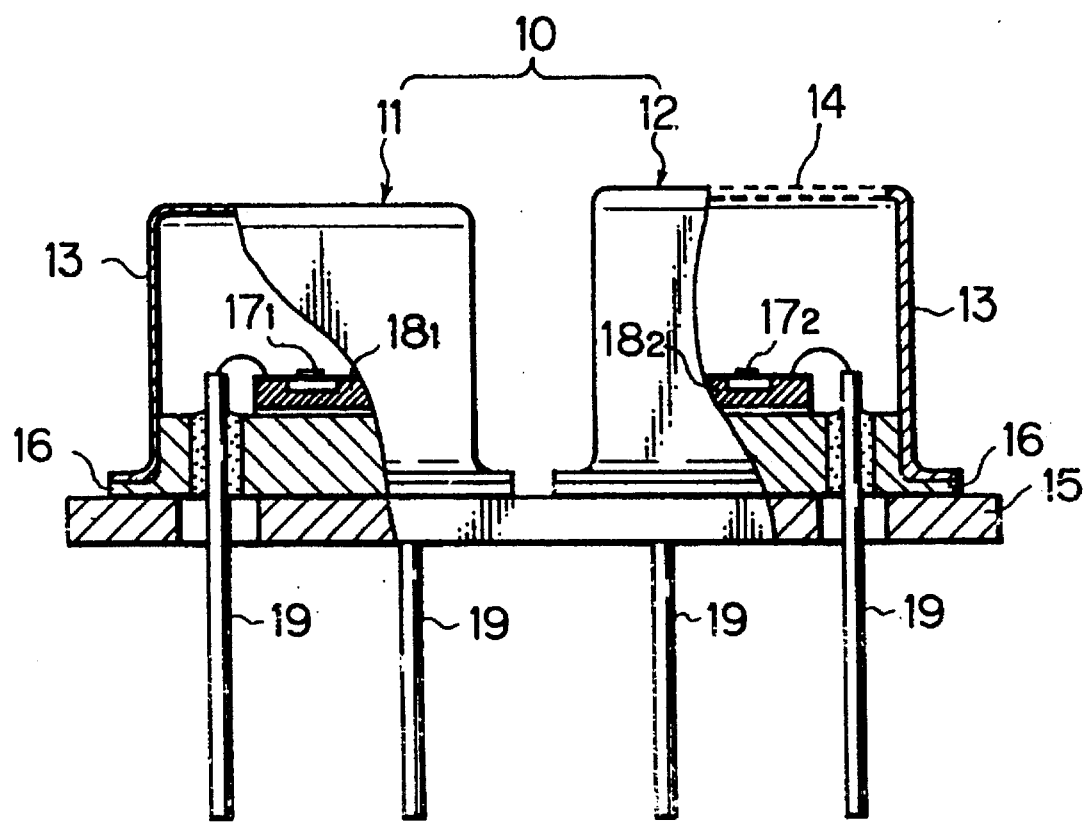
FIG. 1 is a partial sectional view showing construction of a conventional hygrometer.

FIG. 1 is a partial cross-sectional view showing a construction of a conventional hygrometer 10 comprising a temperature-compensating element 11 and a sensing element 12 disposed close to each other on a high heat-conductivity type heat-equalizing plate 15 made of, e.g., aluminium. Both the temperature-compensating element 11 and the sensing element 12 have respective resistors $17_1$ and $17_2$ being micro-bridges of the same size being disposed on respective detection chips $18_1$ and $18_2$ which are secured to a high heat-conductivity type base 16 secured on the heat-equalizing plate 15. Each element is provided with lead pins 19 insulated with hermetic seals. The temperature-compensating element 11 and the sensing element 12 differ from each other by that the temperature-compensating element 11 has a resistor $17_1$ in a seal cap 13 filled with a dry air of the steady-state pressure while the sensing element 12 has a resistor $17_2$ exposed to ambient atmosphere through a gas-permeable top-mesh 14 of a cap 13.

In the shown hygrometer, the resistor $17_1$ of the temperature-compensating element 11 and the resistor $17_2$ of sensing element 12 are heated through respective lead pins 19 with a specified electric power. Since the resistor $17_1$ of the temperature compensating element 11 is enclosed in sealing cap 13 charged with the dry air under a constant pressure, it can not be affected by the humidity of the atmosphere and can vary its value as the ambient temperature changes, i.e., detecting the ambient temperature change. On the other hand, the resistor $17_2$ of the sensing element 12 are disposed in a cap 13 having the meshed top 14 and, therefore, it can vary its resistance with a change of the atmospheric humidity and temperature. Accordingly, by subtracting the resistance value of the resistor $17_2$ of the sensing element 12 from the resistance value of the resistor 11 of the temperature-compensating element 11 it is possible to determine a change of resistance by the effect of the humidity of the ambient atmosphere. In practice, the change of the resistance is detected as a voltage value.

When the ambient temperature rapidly changes, the temperature-compensating element 11 enclosed with the seal cap 13 may not change its resistance in time, i.e., it may delay in response to the change since there is an air buffer layer between the resistor $17_1$ and the seal cap 13, which has a small heat conductivity and delays the heat transfer to the element.

On the other hand, the sensing element mounted in the cap 13 with the mesh 14 may directly contact at its resistor $17_2$ with the ambient atmosphere and, therefore, may respond without delay to a change of the ambient atmosphere. If the ambient atmosphere suddenly changes, there may arise a difference between the ambient temperatures measured by the sensing element 12 and by the temperature-compensating element 11.

FIGS. 2A to 2C are views for explaining how a detection error arises due to response delay of the conventional hygrometer when sensing a change of ambient temperature. As shown in FIG. 2A, when an ambient temperature T having been maintained at 20° C. for a period from $t_0$ to $t_1$ (0–0.01 sec.) suddenly rose to temperature T=40° C. from the time $t_2$ (0.02 sec.) and is kept thereafter at a constant temperature T=40° C., temperature change components (expressed as voltage) of the sensing element 12 at respective moments are sensed as shown in FIG. 2B and temperature change components (expressed as voltage) of the temperature-compensating element 11 at respective moments are sensed with a considerable time lag as shown by hatching in FIG. 2C.

For instance, if the ambient temperature evenly rises from T=20° C. at time $t_1$ (0.01 sec.), the sensing element 12 quickly senses a change $\Delta E_1 b$ in response to a change of the ambient temperature as shown in FIG. 2B but the temperature compensating element 11 detects still the temperature of 20° C. While the sensing element 12 quickly senses the changes $\Delta E_1 b$ and $\Delta E_2 b$ in response to changes of the ambient temperature T for the period $t_1$ to $t_2$ (0.01–0.02 sec.) and thereafter as shown in FIG. 2B, the temperature compensating element 11 does not sense any temperature change until the time $t_2$ (0.02 sec.) and senses a temperature change $\Delta E_3 c$ after the time $t_3$ (0.03 sec.), i.e., it can not follow up the changes of the ambient temperature outside the seal cap but responds thereto with a time lags. This results in an error of humidity detection due to the detection delay, which corresponds to a total of $\Delta E_1 b$, $\Delta E_2 b$ and $\Delta E_3 b$ minus $\Delta E_3 c$. Accordingly, when these elements are periodically driven with a short-time electric power, a temperature sensed by the temperature-compensating element 11 obviously differs from a current ambient temperature.

Referring to FIG. 3, there is shown another conventional hygrometer 20 which differs from the conventional general-type hygrometer of FIG. 1 based on a thermal conductivity principle and involving a time delay of the temperature-compensating element 12 due to the air layer therein, by its construction aiming to reduce such a buffer air layer as the temperature compensating element 12 of FIG. 1 has. In the hygrometer 20, a sensing chip 24 serving as a substrate is secured onto a base 22 in the seal cap with a meshed top 21 and a temperature-compensating resistor 25 and a sensing resistor 26 are disposed each in form of a micro-bridge on the sensing chip 24 which is provided with a cap cover 27 internally separating the above-mentioned two resistors and having a vent 28 in the top of its portion wherein the sensing resistor 26 is mounted.

Since the temperature compensating resistor 25 is disposed in the cap cover 27 with a thin air layer to reduce a time delay in sensing an ambient temperature, a heat transfer time is reduced but the temperature-compensating resistor 25 can be said as the same with the temperature-compensating element 11 in regard of presence of an air layer.

Figure 4:
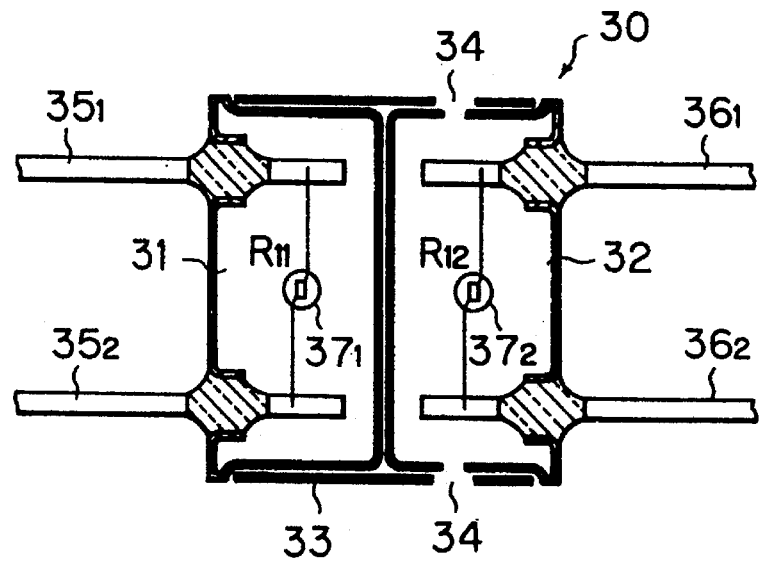
FIG. 4 is a construction view of another conventional hygrometer.

FIG. 4 is a sectional plan view showing another conventional hygrometer 30 wherein a temperature compensation chamber 31 and a sensing chamber 32 are disposed close to each other by the use of equalizing sleeve 33, the sensing chamber 32 with vents 34 open to ambient atmosphere incorporates a sensing element $37_2$ (resistor R11) connected at its both ends to respective leads $36_1$ and $36_2$, and the temperature compensation chamber 31 incorporates a temperature compensating element $37_1$ (resistor R11) connected at its both ends to respective leads $35_1$ and $35_2$.

Each vent 34 of the sensing chamber 32 is smaller in its opening area than the meshed vent. Therefore, the response time of the sensing chamber 32 can be increased near to the response time of the temperature compensation chamber 31. This is an attempt to eliminate a detection error due to the difference of response time lags.

Figure 5:
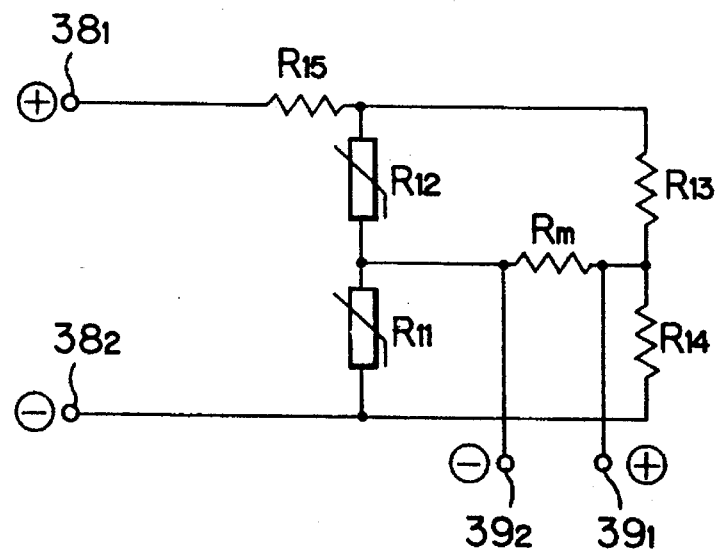
FIG. 5 shows an example of an electrical circuit diagram of the conventional hygrometer shown in FIG. 4.

Referring to FIG. 5, there is shown an example of a circuit configuration of the hygrometer shown in FIG. 4, wherein a temperature-compensating resistor R11 and a sensing resistor R12 together with resistors R13 and R14 form a bridge circuit connected through a resistor R15 with terminals $38_1$ and $38_2$ whereto a power source (not shown) is connected. An output of the bridge circuit, which is a voltage proportional to a humidity, appears across resistor Rm which is connected to connecting points between the sensing resistor R12 and the temperature-compensating resistor R11 and between resistors R13 and R14. The output voltage is outputted through output terminals $39_1$ and $39_2$.

The hygrometer shown in FIG. 4 is a miniature type but may be affected by convection of the ambient atmosphere. Practically, the degree of convection and the accuracy of size and positions of the vents may affect response characteristics of the elements of the bridge circuit, which make it hard to balance the responses of the elements to a change of the ambient temperature. The problem can not be solved basically. The present invention was made to provide the following solution:

In case of heating a resistor heated in an ambient atmosphere to sense a density of a specified gas contained therein, the resistor may vary its resistance value only with a change of the ambient temperature without being influenced by a density of the specified gas if a small electric power is supplied (or the resistor is kept at a specified temperature whereat the specified gas does not effect them: this temperature depends upon a kind of the gas and its mixture ratio). In this case, a resistance value of the resistor is a function of ambient temperature only. On the other hand, a resistance value of the resistor is a function of ambient temperature and density of the specified gas when the resistor is heated with a large electric power. On the basis of these facts, the present invention has proposed such a system wherein a resistor is disposed in the form of a micro-bridge in a cap with a meshed opening and is continuously heated first with a specified small electric power, whereat it can not be effected by the density of the specified gas, and subsequently with a large electric power at which it can be effected by the density of the specified gas. The density of the specified gas is sensed with a single resistor at the same place and determined by subtracting the resistance value obtained at the small electric power from the resistance value obtained at the large electric power.

FIGS. $6A_1$ to $6D_1$ are illustrative of the principle of a hygrometer that is an exemplified application of an atmosphere measuring device according to the present invention. The description will be made in comparison with the conventional hygrometric principle to make it easier to understand. In FIGS. $6A_1$ to $6D_1$, arrows $A_1$, $A_2$ and $A_3$ indicate a flow chart of a hygrometry according to the present invention while arrows $A_1$, $B_1$ and $C_1$ indicate a flow chart of a prior art hygrometry.

FIG. $6A_1$ is a construction view of a humidity sensing element 40 and FIG. $6A_2$ is a construction view of a temperature compensating element 50, wherein are shown seal caps 41, 51, a mesh 42, bases 43, 53, hermetic seals 44, 54, lead pins 45, 46, 55, 56 and resistors 47, 57 (hereinafter called "sensing element").

In FIG. $6A_1$, the humidity sensing element 40 comprises the base 43 made of a high heat-conductivity material, the lead pins 45 and 46 extending through holes made in the base 43 and secured therein with a hermetic seal 44 to be parallel to each other at a specified minute distance, the sensing element 47 is welded to tips of the parallel lead pins 45 and 46 and the seal cap is provided with a mesh 42 and secured to the base 43. The sensing element 47 may be a fine wire or thin film made of material having a positive coefficient of temperature resistance (e.g., platinum, tungsten, nichrome, kanthal) or having a negative coefficient of temperature resistance (e.g., silicon carbide (SiC), tantalum nitride (TaN)) or a miniature temperature element (e.g., thermistor).

The sensing element 47 can vary its resistance value according to an ambient temperature and humidity when being heated at a low temperature or a high temperature and has a small heat capacity. Accordingly, a fine wire or a miniature temperature-sensitive element is used as the sensing element 47 in a micro-bridge configuration, which can quickly reach to a specified temperature of thermal equilibrium state when being heated, and it can also quickly return to an ambient temperature when heating is stopped.

The sensing element 57 of the temperature compensating element 50 shown in FIG. $6A_2$ is identical in its specification to the sensing element 47 of the humidity sensing element 40 shown in FIG. $6A_1$. The sensing element 57 is enclosed in the seal cap 51 having no mesh holes.

The conventional hygrometer using a humidity sensing element 40 of FIG. $6A_1$ and a temperature compensating element 50 and the hygrometer using only a sensing element 40 of FIG. $6A_1$ according to the present invention will be first explained as follows:

FIGS. 7A and 7B are volt-ampere characteristic curves of a humidity sensing element. FIG. 7A shows humidity characteristic which is represented by a volt-ampere characteristic curve $A_1$ (dotted line) at a constant ambient temperature of 30° C. and a humidity of 200 g/m³ and a volt-ampere characteristic curve $A_2$ (solid line) at 30° C. and 0 g/m³. FIG. 7B shows a temperature characteristic which is represented by a volt-ampere characteristic curve $B_1$ (dotted line) at a humidity of 0 g/m³ and a temperature of 20° C., a volt-ampere characteristic curve $B_2$ (solid line) at 30° C. and a volt-ampere characteristic curve $B_3$ (dotted line) at 40° C. A voltage applied to the sensing element is taken on the horizontal axis while a current applied to the sensing element is taken on the vertical axis. As apparent from the volt-ampere characteristic curve $A_1$ of FIG. 7A representing the humidity characteristic of the humidity sensing element at 30° C., if the humidity sensing element is heated with a small current of not more than 2 mA, the curve $A_1$ substantially matches with the curve $A_2$ (with the same corresponding voltage of more than 0.8 V), i.e., the humidity sensing element indicates temperature characteristic without being affected by the humidity.

If the humidity sensing element is heated with a large current of 8 mA, the curve $A_1$ and the curve $A_2$ indicates different voltages 3 V and 4 V respectively. At a large heating current, the voltage of the sensing element drops as the humidity increases. In the other words, the sensing element may output a voltage corresponding to the humidity.

From the volt-ampere characteristic curve representing the temperature characteristic of the sensing element at a humidity of 0 g/m³ of FIG. 7B, it is seen that when a current of, e.g., 2 mA is supplied to the sensing element, a voltage produced across the element can increase as the ambient temperature rises (see curves $B_1$, $B_2$ and $B_3$) because no moisture exists around the sensing element.

FIGS. $6B_1$, $6B_2$, $6B_3$, $6C_1$ and $6D_1$ are graphs which abscissa indicates an absolute humidity (g/m³) and ordinate indicates an output voltage (V). FIG. $6B_1$ shows linear characteristics $B_{11}$, $B_{12}$ and $B_{13}$ representing correlations between absolute humidity and output voltage at ambient temperatures of 20° C., 30° C. and 40° C. respectively and at a current of 8 mA supplied to the sensing element 47 shown in FIG. $6A_1$. The output voltage and the absolute humidity are inversely proportional to each other and directly proportional to the ambient temperature.

On the other hand, the temperature sensing element of FIG. $6A_2$ produces an output voltage that does not depend on the absolute humidity and can vary in proportion with the ambient temperature only as shown in FIG. $6B_2$. Linear characteristics $B_{21}$, $B_{22}$ and $B_{23}$ are obtained at ambient temperatures of 20° C., 30° C. and 40° C. respectively.

Referring to FIGS. $6B_1$ and $6B_2$, the outputs which correspond to the absolute humidities at the same ambient temperatures are reduced from each other, i.e., the characteristic lines $B_{23}$, $B_{22}$ and $B_{21}$ are subtracted from the lines $B_{13}$, $B_{12}$ and $B_{11}$ respectively. By doing so, a correlating line $B_{33}$ of FIG. $6B_3$ can be obtained, which indicates the inverse proportion of the output voltage of the device to the absolute humidity without dependence upon of the ambient temperature.

In case of a hygrometer that is an embodiment of the atmosphere measuring device according to the present invention, a sensing element 47 driven with a small current of, e.g., 1 mA generates an output voltage directly proportional to an ambient temperature only (e.g., at 20° C., 30° C. and 40° C. without affection of the absolute humidity) as shown in FIGS. 7A and 7B. The parallel characteristic lines $C_1$, $C_2$ and $C_3$ of FIG. $6C_1$ are also obtained. This shows the same correlation as FIG. $6B_2$ indicates. An output characteristic line Bo of FIG. $6D_1$ is obtained from FIGS. $6C_1$ and $6D_1$, which is similar to the characteristic of FIG. $6B_3$ and indicates that the output voltage of the sensing element is inversely proportional to the absolute humidity only (without being affected by the ambient temperature).

In the above-mentioned hygrometer according to the present invention, the humidity sensing element 47 is driven with a constant current but may also be driven with a narrow-width current pulse or constant voltage or constant voltage pulse since it has a very small heat capacity and an excellent response characteristic.

FIGS. $8A_1$ and $8A_2$ are views for explaining methods for driving a humidity sensing element of a hygrometer that is an embodiment of an atmosphere measuring device according to the present invention. FIG. $8A_1$ shows a current pulse drive circuit and FIG. $8A_2$ shows a voltage pulse drive circuit. The hygrometer according to the present invention can be driven with a pulse of a constant current or voltage if the drive meets the humidity characteristic curve of FIG. 7A and the temperature characteristic curve of FIG. 7B. In case of the constant-current pulse-drive circuit shown in FIG. $8A_1$, a constant-current pulse power source 60 is connected in series with a sensing element 61 which generates a detection voltage Vout across the element. In case of the pulse-voltage drive circuit of FIG. $8A_2$, a constant-voltage pulse power source 62, a detection resistance 63 and a sensing element 61 are connected in series and a voltage Vout across the detection resistor 63 is detected. In both cases, two kinds of the constant current or voltage pulses for different ambient temperatures are applied to the sensing element 61.

FIG. 8B illustrates an example of a pulse train of driving current. The sensing element 61 is supplied with a small current pulse of 2 mA in amplitude and 50 ms in width for a period $t_1$–$t_2$ and further with a large current pulse of 8 mA in amplitude and 50 ms in width for a period $t_2$–$t_3$. After a pause period of 100 ms ($t_3$–$t_4$), the sensing element is driven again with a train of a small current pulse of 2 mA in amplitude and 50 ms in width and a large current pulse of 8 mA in amplitude and 50 ms in width.

FIG. 8C indicates a pulse train of voltages developed across the sensing element 61 driven with a current pulse train shown in FIG. 8B. When a current pulse rises, a voltage pulse is produced with a time delay. Therefore, detection of the voltages must be made for a time $C_1$ and a time $C_2$ to measure stabilized voltage values. The pause period of 100 ms between time $t_3$ and time $t_4$ of the driving current pulse trains shown in FIG. 8B is selected so that temperature of the sensing element 61 after being driven with a current pulse of 8 mA may become substantially equal to the ambient temperature.

In case of FIG. 8B, a small current pulse and a large current pulse are continuously applied to the sensing element 61. If a specified time interval is provided to stabilize a small current pulse before the large current pulse is applied to the sensing element, it becomes impossible to sense a voltage at a high response because a time delay is associated with each driving current pulse. On the contrary, according to the driving method shown in FIG. 8B, whereby the large current pulse is applied directly after the small current pulse, the sensing element can be preheated with the small current pulse and, therefore, can quickly respond to the large current pulse with producing the output voltage which waveform is improved as shown with dotted lines $d_1$ in FIG. 8D.

FIGS. 9A and 9B are illustrative of a pulse waveform of a current and a pulse waveform of an output voltage when the sensing element is driven successively with a large current pulse and a small current pulse. When the sensing element is driven first with a large current pulse (8 mA) for a period of time $T_1$ for detecting a temperature and a humidity of an atmosphere and subsequently with a small current pulse (2 mA) for a period of time $T_2$ for detecting the temperature only, the sensing element produces an output voltage at the large current pulse, which, as shown in FIG. 9B, has an increased pulse rising time $B_1$ and an increased pulse decay time $B_2$ due to the delayed response. Consequently, the time needed for stabilizing the output voltage of the sensing element when being driven with the small current pulse is also increased, resulting in increase of response time and impairment of detection.

FIGS. 10A to 10D are views for explaining a correlation between the atmosphere change and the output characteristic of a hygrometer which is an embodiment of an atmosphere measuring device according to the present invention. FIG. 10A shows a change of temperature along a time axis, FIG. 10B shows a change of humidity along a time axis, FIG. 10C shows an applied current waveform, and FIG. 10D shows waveforms of detection output voltages corresponding to a change of the temperature and a change of humidity of an atmosphere when the current is supplied to the sensing element.

The current applied to the sensing element is a pulse train that consists of a small current of 2 mA and a large current of 8 mA supplied in succession and followed by a specified pause period. The current pulse is outputted each one for a period of $t_1$ to $t_2$ and a period of $t_2$ to $t_3$. On the other hand, the temperature changes from a constant level of 30° C. to 20° C. (L1), 30° C. (L2) and 40° C. (L3) for the period of $t_1$ to $t_2$ and it is kept at 30° C. for any other period as shown in FIG. 10A. The humidity varies from a constant level of 20 g/m$^3$ (L5) to 10 g/m$^3$ (L4) or 30 g/m$^3$ (L6) for the period of $t_1$ to $t_2$ as shown in FIG. 10B.

Accordingly, both temperature and humidity of an atmosphere are constant for the period of $t_0$ to $t_1$, only the temperature changes for the period of $t_1$ to $t_2$ and only the humidity changes for the period of $t_2$ to $t_3$. As shown in FIG. 10D, the detection output voltage takes waveforms corresponding to respective periods. A constant output voltage corresponding to a constant temperature and a constant humidity is obtained for the period $t_0$-$t_1$, and an output voltage proportional to an ambient temperature only is obtained for the period $t_1$-$t_2$ wherein a result of subtraction of an output voltage obtained at a small driving current from an output voltage obtained at a large driving current is a constant and no influence of the humidity is observed. For the period $t_2$-$t_3$ wherein only the humidity varies, an output voltage remains constant even at the humidity L4, L5, L6 when a small driving current is applied and it varies under the influence of the humidity only when a large driving current is applied. In this case, a small output voltage is obtained at a high humidity L3 and a large output voltage is obtained at a low humidity L4. The above-mentioned arithmetic operations are performed by a driving circuit which will be described below in detail.

FIG. 11 is an elctric circuit diagram showing an example of a driving circuit of a hygrometer that is an application of an atmosphere measuring device according to the present invention. In FIG. 11, 61 is a sensing element, 64 is a constant-current circuit for supplying the sensing element with a constant current, 65 is a detecting circuit for detecting the output of the sensing element 61, 66 is a circuit for setting a coefficient, 67 is a hold circuit, 68 is a subtraction circuit and 69 is an output terminal.

The constant-current circuit 64 is loaded with the sensing element 61 and the reference resistance Rr which is connected at one end in series with the sensing element 61 and at one end to the ground and which voltage is fed back to an inverting input terminal of the constant-current circuit 64. A non-inverting input terminal of the constant-current circuit 64 is connected with a switch $SW_1$ which has contacts "a" and "b" for supplying a reference voltage Vref1 and Vref2 respectively and a grounded constant "c". The reference voltages Vref1 and Vref2 are set as follows:

$$\text{Vref1}=2Rr \text{ (mV)} \tag{1}$$

$$\text{Vref2}=8Rr \text{ (mV)} \tag{2}$$

The connecting point of the output terminal of the constant-current circuit 64 and one terminal end of the sensing element 61 is connected to an inverting input terminal of the detecting circuit 65 and the connecting point of the other terminal of the sensing element 61 and the reference resistance Rr is connected to the non-inverting input terminal of the detecting circuit 65. An output terminal of the detecting circuit 65 is connected to a switch $SW_2$ which has contacts "a" and "b": the contact "a" is used for setting a coefficient K for converting a low heating temperature to an ambient temperature when calculating a humidity, for example, by connecting thereto the coefficient setting circuit 66 which can vary a multiple factor in accordance with a set value of the coefficient K, and contact "b" is connected to an input terminal of the subtraction circuit 68 for inputting thereto an output voltage $V_D$ when a large current is supplied for heating a high temperature.

A switch $SW_3$ having contacts "a" and "c" and the hold circuit 67 are provided between the coefficient setting circuit 66 and the subtraction circuit 68. The contact "a" of the switch $SW_3$ is connected to the hold circuit 67.

The switches $SW_1$, $SW_2$, $SW_3$ of the thus constructed driving circuit are interlocked with each other and operate with changing-over their contacts "a", "b" and "c" at a time. When the switch turns on its contact "a", a voltage equal to the reference voltage $V_{REF}1$ is applied to the reference resistance Rr connected to the inverting terminal of the constant-current circuit 65 and a constant current of 2 mA flows through the sensing element 61. Similarly, when the switch turns on its contact "b", a voltage equal to the reference voltage Vref2 is applied to the reference resistance Rr and a current of 8 mA flows through the sensing element 61.

FIGS. 12A to 12H are indicative of waveforms of voltages appearing at corresponding portions of the driving circuit shown in FIG. 11. Referring now to FIG. 11 and FIGS. 12A to 12H, the operation of the driving circuit will be described as follows: The switch $SW_1$ (together with the switches $SW_2$ and $SW_3$) operates to close its contact "a" and open contact "b" by corresponding driving voltage pulses of waveforms shown in FIGS. 12A and 12B at intervals of $t_1$ to $t_2$ and $t_2$ to $t_3$. A driving current of 2 mA and 8 mA shown as "is" in FIG. 12C follows through the sensing element 61 in accordance with above-mentioned switching operations. When the contact "a" is closed, a voltage Vs, which is proportional to an ambient temperature and has a waveform shown in FIG. 12D, developed on the contact switch $SW_2$. The voltage Vs is inputted into the coefficient setting circuit which in turn multiplies the voltage by a preset coefficient K and outputs the resulting voltage V's (=KVs) shown in FIG. 12E. Since the output voltage Vs produced by closing the contact "a" of the switch $SW_2$ is not correctly proportional to an ambient temperature, it is corrected by the coefficient K which is given by the following equation:

$$K=(VD-\text{change by humidity})/Vs \tag{3}$$

Figure 12A:
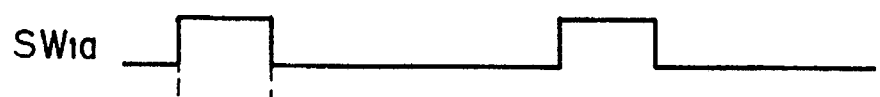
Figure 12B:
Figure 12C:
Figure 12D:
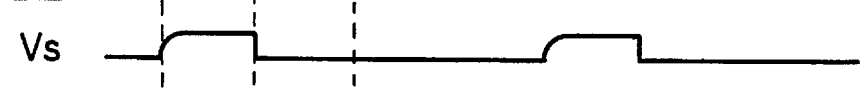
Figure 12E:
Figure 12F:
Figure 12G:
Figure 12H:
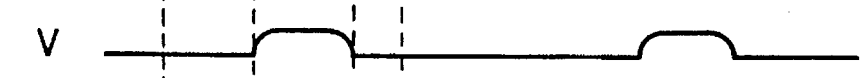

The hold circuit 67 outputs a voltage V"s equal to the voltage V's (=V"s) shown in FIG. 12F. The subtraction circuit 68 receives the voltages VD and V"s and generates an output voltage V shown in FIG. 12H, which is proportional to a humidity.

$$V=VD-V"s \quad (4)$$

FIG. 13 is an electrical circuit diagram showing another example of a driving circuit of a hygrometer that is an application of an atmosphere measuring device according to the present invention. In FIG. 13, 70 is a voltage detection circuit, 71 is a current detection circuit and 72 is a dividing circuit. Other parts similar in function to the parts shown in FIG. 11 are given like reference numerals.

The driving circuit of FIG. 13 detects humidity by a change of resistance value of the sensing element 61. Whenever the sensing element 61 is driven with a small current and a subsequent large current, the voltage detection circuit 70 detects a voltage across the sensing element 61 and inputs it into a dividing circuit 72. On the other hand, the current detection circuit 71 detects a voltage across the reference resistance Rr having a known resistance and inputs it into the dividing circuit 72 which in turn calculates a resistance value of the sensing element 61.

The circuitry after a switch $SW_2$ operates on the same principle as that of the driving circuit of FIG. 11 and calculates a humidity by subtracting a voltage produced at a small current pulse from a voltage produced at a large current pulse.

FIGS. 14A and 14B are illustrative of a two-power driving system relating to the present invention, where are shown a waveform of a driving current (FIG. 14A) and a waveform of an output voltage (FIG. 14B) of the same humidity sensing element as shown in FIGS. 8B and 8C. The humidity sensing element is driven with two driving current pulses of 2 mA and 8 mA in succession as shown in FIG. 14A. An output voltage with a lag shown in FIG. 14B is obtained. This driving system requires two highly accurate power sources which accuracy and stability may directly influence the output voltage. For example, to obtain two current pulses of 2 mA and 8 mA in height it is needed to use different circuit parts on the characteristics of which the accuracy of pulse height depends.

FIGS. 15A and 15B show an example of driving current waveform and output voltage waveform of a hygrometer that is an embodiment of an atmosphere measuring device according to the present invention. The sensing element is driven with a triangular (sawtooth) current proportional to time for a period $t_1-t_2$ as shown in FIG. 15A, thereby an output voltage with a time delay is produced as shown in FIG. 15B. Similarly to the case of FIGS. 14A and 14B, the voltages produced at a small driving current and at large driving current are measured at time points P and Q specified as measuring timing points. To drive the sensing element with a constant saw-tooth current, it is needed to use only one power source which can be precisely manufactured and requires only setting measurement time points P and Q to sense the output voltages produced by applying the corresponding currents to the sensing element.

FIGS. 16A and 16B show other driving current waveforms of a hygrometer that is an embodiment of an atmosphere measuring device according to the present invention. FIG. 16A shows a waveform of an approximately triangular pulse of current whose variation decreases convexly with time. FIG. 16B shows waveform of an approximately triangular pulse of current whose variation increases concavely with time. Driving with these pulses may attain the same effectiveness as the case of driving with a triangular current pulse of FIG. 15A if stabilized supply of such current is assured.

FIGS. 17A to 17E show a timing chart for explaining operation of a driving circuit of a hygrometer that is an embodiment of an atmosphere measuring device according to the present invention. FIG. 17A illustrates waveforms of output voltages generated for the period the sensing element is driven with a low-temperature heating current and a subsequent high-temperature heating current. FIG. 17B illustrates a waveform of an output voltage generated by driving with a sawtooth current, FIG. 17C illustrates clock pulse train, FIG. 17D illustrates a measurement ON-OFF signal and FIG. 17E illustrates a reset signal.

Time points C1, C2 shown in FIG. 8C and time points P, Q shown in FIG. 14B are determined on condation that an output voltage of the sensing element 61 is stabilized. A measurement start timing point "ta" in case of low-temperature driving and a measurement start timing point "tb" in case of high-temperature driving can be determined directly if a timing point "$t_0$" for driving thermally the sensing element 61 is determined. For instance, the measurement timing points "ta" and "tb" are determined as points A and B respectively, whereat the voltage waveform of FIG. 17A and the sawtooth voltage waveform of FIG. 17B intersects each other (shown by lines A—A and B—B) and the voltage measurements at a low-temperature and a high-temperature are conducted respectively for a period of to to ta (for low temperature) and a period of ta to tb (for high temperature).

A low- and high-temperature driving period of to to $t_1$ and the pause period of $t_1$ to $t_2$ are determined by measurement ON-OFF signals shown in FIG. 17D and a reset signal shown in FIG. 17E is generated at the time wherein the measurements of the output voltages at the low- and high-temperatures are completed. All these timing points ta, tb, $t_1$, $t_2$ are measured and defined by counting clock pulses shown in FIG. 17C.

FIG. 18 is an electrical circuit diagram showing an example of timing-signal generating method according to the present invention. In FIG. 18, 80 is a clock pulse generating circuit, 81a, 81b, 81c are counters and 82 is a reference voltage generating circuit. The clock pulse generating circuit 80 generates clock pulse signals shown in FIG. 17C. When the counter circuit 81a counts the preset number of clock pulses corresponding to the timing point ta, it generates a timing pulse "a" to start measurement. Similarly, when the counter circuit 81b counts the preset number of clock pulses corresponding to the timing point tb, it generates a timing pulse "b" to start measurement. The counter circuit 81c outputs timing pulse signals which define the time point $t_1$ for low- and high-temperature driving, and gives measurement ON-OFF signals and the time point $t_2$ for pausing. The counter circuits 81a, 81b are reset by a pulse signal defining the time point $t_1$ and then counting gate of the counter 81a, 81b are closed. The gates of the counter circuits 81a, 81b are opened by a pulse defining the time $t_2$ and then, the reference-voltage generation circuit 82 generates a reference voltage E to drive the sensing element.

FIG. 19 shows an example of a reset circuit, and FIGS. 20A to 20D are illustrative of a time chart of the reset circuit shown in FIG. 19. When a measurement ON-OFF signal is applied to an input terminal D of a delay flip-flop circuit 83, an output Q corresponding to the ON-OFF signal is given with delay by 1 clock pulse as shown in FIG. 20C. A reset signal of a clock pulse width shown in FIG. 20D is generated as an AND-gate output (output of the AND circuit 85) resulting from the clock pulse of an inverting circuit 84 and the output Q of FIG. 20C.

FIG. 21 is illustrative of an electrical circuit diagram of a sawtooth-current driving circuit for driving a sensing element according to the present invention, which includes a resistance Ro for receiving the reference voltage E, an integrating circuit composed of said resistance Ro, a feedback condenser Co and an operating amplifier 86, and a switch 87 for discharging the feedback condenser according to a reset signal. This driving circuit generates a constant sawtooth voltage $V_1$ that is proportional to time t within the period defined by a reset signal.

$$V_1 = (E/CoRo) \cdot t \tag{5}$$

The voltage $V_1$ is applied to a constant current circuit composed of the operational amplifier 88 having a reference resistance Rr and four resistances Ra equal to the input resistance. A constant sawtooth current "i" proportional to the voltage $V_1$ flows in a sensing element. The current "i" is determined according to the following equation (6):

$$i = \frac{V_1}{Rs} = \frac{1}{Rs} \times \frac{E}{CoRo} \times t \tag{6}$$

FIG. 22 is a block diagram for explaining an example of a humidity output circuit of a sensor element with a sawtooth current drive according to the present invention, which includes amplifier circuits 89 and 90, a coefficient setting circuit 91, hold circuit 92 and 93 and a subtraction circuit 94.

When a constant sawtooth current i determined by the equation (6) flows through a sensing element 61, a voltage develops across the sensing element 61 and enters into the amplifier circuits 89 and 90 connected in parallel to the sensing element. The amplifier circuit 89 is used for measuring an output voltage Vs produced at a small driving current and is provided with the coefficient setting circuit 91 and the hold circuit 92 connected in series thereto. The amplifier circuit 90 is provided to measure an output voltage $V_D$ produced at a large driving current and the hold circuit 93 is connected thereto.

A corrected voltage Vd' which is obtained by multiplying the output voltage Vs produced at a small driving current by the coefficient K is hold by the hold circuit 92 with a measurement timing pulse a. The voltage $V_D$ produced at a large driving current is held by the hold circuit 93 with measurement timing pulse b. The output voltage Vs" (=Vs'), produced at the small driving current, which is hold by the held circuit 92, and the output voltage $V_D$ produced at a large driving current, which is held by the hold circuit 93, are entered into the subtraction circuit 94 which subtracts the voltage Vs" from the voltage $V_D$ and generates resultant voltage V being proportional to the absolute humidity. The small driving current is 2 mA for heating the sensing element at low temperature and the large driving current is 8 mA for heating the sensing element at high temperature. Constants Co, Ro, Rs and E of the circuit are determined from the equation (6) in such a way that 2 mA at t=ta and 8 mA at t=tb may be assured.

FIG. 23 is a block circuit diagram for explaining another example of a humidity output circuit with a saw-tooth current drive according to the present invention. In FIG. 23, numeral 96 designates an A–D converter and numeral 97 designates a CPU (central processing unit). Other parts similar in function to the parts shown in FIGS. 18 and 21 are given like reference numerals.

The humidity output circuit of FIG. 23 uses clock pulses from a clock of the CPU 97 as timing signals (i.e., measurement ON-OFF signal, measurement timing signal ta, tb and reset signal). The CPU 97 has storing function and, therefore, eliminates the necessity of providing a hold circuit for holding output voltages sensed at a low temperature and a high temperature. The output voltages of a sensing element 61 are amplified by an amplifier circuit 95 to specified voltage values which are then converted by the A–D converter 96 into digital values. The CPU reads and stores digital values of the detected voltages according to the timing signals ta and tb and then sets coefficients and performs arithmetic operations on the digital data, easily determining a humidity.

FIG. 24 is a view for explaining an example of a humidity measurement circuit using a sensing element according to the present invention, which is featured by using a voltage pulse for driving the sensing element. In FIG. 24, numeral 98a designates a first reference voltage generating circuit, numeral 98b designates a second reference voltage generating circuit and numeral 99 designates a constant voltage circuit. Other parts similar in function to the parts shown in FIG. 23 are given like reference numerals. The first reference voltage generating circuit 98a is a constant voltage circuit which applies a low reference voltage $V_{REF}1$ to a sensing element 61. The second reference voltage generating circuit 98b is a constant voltage circuit which applies a high reference voltage $V_{REF}2$ to a sensing element 61. The constant voltage circuits 98a and 98b are connected to contacts "a" and "b", respectively, of a switch $SW_1$ which is operated by timing pulses from a terminal $P_{01}$ of a CPU 97 and has an grounded contact "c" The switch $SW_1$ is also connected to a non-inverting input of the constant voltage circuit 99.

The constant voltage circuit 99 is loaded with a reference resistance Rr and the sensing element 61 which is connected at one end in series with the reference resistance Rr and at one end to the ground. The connecting point is connected to an inverting input terminal of the constant-voltage circuit 99.

In the constant voltage circuit 99, a voltage Vs developed across the sensing element 61 is equal to a voltage applied to corresponding contact of the switch $SW_1$, i.e., a constant output voltage is supplied:

Vs=$V_{REF}1$ when contact "a" is closed;

Vs=$V_{REF}2$ when contact "b" is closed;

Vs=0 when contact "c" is selected.

When the voltage Vs of the sensing element 61 having resistance Rs is constant, a current "is" flowing through the reference resistance Rr is equal to Vs/Rs and a current corresponding to the resistance Rs flows through the sensing element 61. For instance, when the resistance Rs varies under the influence of temperature or humidity of the ambient atmosphere, the current "is" flowing through the resistance Rs varies correspondingly. This current "is" is detected as a voltage Vr (=is×Rr) by an amplifier circuit 95.

FIG. 25 shows an exemplified time chart for the circuit of FIG. 24, on the assumption that $V_{REF}1$=0.5 V and $V_{REF}2$=4.5 V. In this case, Vs=0.5 V is applied for a period $t_1$ the contact "a" of the switch $SW_1$ being closed, Vs=4.5 is applied for a period $t_2$ the contact "b" of the switch $SW_1$ being closed, and a pause (with no driving voltage) is produced for a period $t_3$ the contact "c" being selected. Timing points similar to the timing points for the constant current drive of FIG. 11 are set. The sensing element is heated at a low temperature while the switch $SW_1$ closes its contact "a". This is the same as the case of heating by applying a constant current of 2 mA. The sensing element is heated at a high temperature while the switch $SW_1$ closes its contact "b". This is the same as the case of heating by applying a constant current of 8 mA.

FIG. 26 is a partially cutaway view in perspective of another example of a humidity (moisture) sensor of a hygrometer that is an embodiment of an atmosphere measuring device according to the present invention. In FIG. 26, 100 is a silicon substrate, 101 and 102 are cavities, 103 and 104 are oxide film substrate, 105 and 106 are resistors and A, B and C are electrodes.

The humidity sensing element shown in FIG. 6A$_1$ has a single sensing element 47 being a resistor of micro-bridge configuration, which is continuously heated at a low temperature and at a high temperature for, e.g., 50 ms each. Practically, such a sudden change of an atmosphere may not occur, but, ideally, it is desired to heat a single sensing element 7 at a low temperature and a high temperature at the same time and to detect a difference of resistance values. However, it is impossible to heat a sensing element at the same place simultaneously at a low temperature and a high temperature. Therefore, in the humidity sensor of FIG. 26, which is another embodiment of the present invention, two resistors are disposed as close as possible on a substrate, assuring no effect on each other.

As shown in FIG. 26, the humidity sensor is constructed on a silicon crystal substrate 100 with an oxide film 101a, whereon two cavities 101, 102 of the same configuration and size are formed by anisotropic etching with leaving an oxide film substrates 105 and 106 having respective supporting arms 103a–103d and 104a–104d bridged over the cavities, a fine resistors 105 and 106 are formed of a zigzag pattern on the oxide film substrates 105 and 106 and are connected in series by means of a connecting portion whose end formed as an electrode "B" and other ends of the resistors are formed as electrodes "A" and "C". The silicon crystal substrate 100 is packaged by using a mesh cap, instead of a seal cap, to permit ventilation therethrough.

The operation of the thus constructed humidity sensor is described as follows:

FIGS. 27A to 27D show a time chart for determining humidity by the humidity sensor of FIG. 26.

FIG. 27A shows a sequence of equally spaced clock pulses ($a_1$, $a_2$, $a_3$ . . . ) to be generated at a fixed time interval from a clock circuit (not shown).

FIG. 27B shows that a series of low-amplitude low-voltage pulses ($b_1$, $b_2$, $b_3$ . . . ) in synchronism with the clock pulses ($a_1$, $a_2$, $a_3$ . . . ) are generated to heat the resistor 106 at a low temperature to produce and measure a resistance value being proportional to a temperature of an atmosphere.

FIG. 27C shows that a series of high-amplitude high voltage pulses ($c_1$, $c_2$, $c_3$ . . . ) in synchronism with clock pulses ($a_1$, $a_2$, $a_3$ . . . ) are generated to heat a resistor 105 between terminals B-A at high temperature to produce and measure a resistance value being proportional to a temperature and a humidity of an atmosphere.

FIG. 27D shows a series of humidity sensed pulses ($d_1$, $d_2$, $d_3$ . . . ) which amplitude (wave height) is proportional to humidity of an atmosphere and which in synchronism with the clock pulses ($a_1$, $a_2$, $a_3$ . . . ) are obtained by subtracting a resistance value of the resistor 106 heated at low temperature from the resistance value of resistor 105 heated at high temperature by the use of a humidity calculation circuit (not shown).

FIGS. 28A to 28C show another time chart for determining a humidity by the humidity sensor of FIG. 26. Clock pulses ($a_1$, $a_2$, $a_3$ . . . ) shown in FIG. 28A have the same intervals as those of FIG. 27A and are used for synchronizing the operations of circuits driving the resistors 105 and 106.

The driving method with the time chart of FIGS. 28A to 28C are a further improvement of the driving method with the time chart of FIGS. 27A to 27D. The improved driving method is intended to simultaneously drive the resistor 105 at a high temperature and the resistor 106 at a low temperature for a specified period and to subsequently drive the resistor 105 at the low temperature and the resistor 106 at the high temperature for a specified period, making each resistor sense a temperature and a temperature plus a humidity alternately.

While the resistor 106 between terminals B-C is heated with a power pulse "$b_1$" at a low temperature in synchronism with a clock pulse, the resistor 105 between terminals B-A is heated with a power pulse at a high temperature. At the time of clock pulse "$a_1$", a humidity-sensed pulse (not shown) is determined by subtracting a temperature-sensed resistance value obtained by heating with the pulse "$b_1$" from a temperature-humidity-sensed resistance value obtained by heating with the pulse "$c_1$". At the subsequent time of clock pulse $a_2$, a humidity-sensed pulse is determined by subtracting a temperature-sensed resistance value obtained by heating with the pulse "$c_2$" from a temperature-humidity-sensed resistance value obtained by heating with the pulse "$b_2$".

As apparent from the foregoing, the present invention provides following advantages:

Variation in characteristics of separate sensing elements:

Any conventional atmosphere measuring device in which a combination of a separate sensing element and a separate temperature-sensing element is adopted has such drawbacks that it can not be applicable for wide-range humidity measurement and can not attain a higher sensing performance if both sensing elements have not matched resistance values (volt-ampere characteristic) and temperature coefficients of resistors. The combination of strictly matched elements is therefore required, that leads to increasing their manufacturing cost because of reduced mass productivity and product yield and of increased man-hours. On the contrary, in an atmosphere measuring device according to the present invention, detection and compensation can be performed by a single sensing element that has no difference between its resistance value (volt-ampere characteristic) and resistance-temperature coefficient and therefore can attain high performance.

Variation in response time (rising time) of separate sensing elements:

A conventional method using a combination of two sensing elements poses a problem regarding variations in response time of the elements. The present invention uses a single sensing element which can sense a temperature and a density of a specified gas at a constant response time.

Aged variation of characteristics of sensing elements:

Any conventional method using a combination of two sensing elements poses a problem that two elements may differently deteriorate with time and be of no use when their characteristics become mismatched. It has been also hard to predict or check by itself how long or whether the elements can be used. The present invention uses a single element which is free from the above-mentioned problem and can be used until it becomes to indicate considerably deteriorated performance.

Temperature influence of a seal cap:

In a conventional atmosphere measuring device having a temperature-compensating element, a gas of a other temperature than that of the element flows along a seal cap and may exert an influence through sealed air on an internal heat-generating element to produce even a small output which affects the temperature-compensation, resulting in erroneous detection of a variation in density of the gas to be sensed. The present invention uses a single sensing element which may detect the gas density, and the gas density plus ambient temperature under the same conditions of an ambient atmosphere, thereby it is free from the trouble occuring in the conventional device.

Electric power consumption:

In the conventional atmosphere measuring device, a separate temperature-compensating element requires power supply in amount of about two times more than that of the sensing element.

In the atmosphere measuring device according to the present invention, electric power required for compensation is several or tens times less than that required for sensing. Total power consumption of the device is about one-half of that of the conventional devices.

Variation of pressure:

In contrast to the conventional device wherein temperature compensation is conducted under a constant specified pressure in the seal cap, the device according to the present invention can conduct measurements of ambient temperature and the gas density at a substantially same pressure of an atmosphere, thereby it can accurately measure a gas density even when the atmosphere suddenly varies.

Furthermore, the present invention also proposes to drive two sensing elements (resistors) alternately with different power pulses. By doing so, the life time of the elements may be simply doubled and heat accumulation at the side for sensing the ambient temperature and the gas density is reduced, thereby the elements can operate more frequently at a reduced interval and may a wider application field. Besides, the two-element device can be switched ON with a stabilized uniform load to the power source and can be manufactured by using the IC production technology resulting in minimal variation of the elements.

FIGS. 29A and 29B are construction views of a conventional thermal type flow sensor. FIG. 29A is a plan view and FIG. 29B is a sectional view taken along line B—B of FIG. 29A.

This sensor is manufactured in such a manner that an insulating layer of silicon nitride is applied to a silicon singlecrystal substrate 111, a cavity portion 113 is formed by anisotropic etching on the substrate, leaving thereon micro-bridges 112a, 112b and 112c, and then resistors 114, 115 and 116 are formed by depositing zigzag patterns of a metal layer of permalloy or platinum onto the micro-bridges 112a, 112b and 112c respectively. The center resistor 115 serves as a heater. The resistors 114 and 116, which are disposed at opposite sides of the heater 115, have the same resistance value and are substantially identical in size. The resistor 114 is used as a temperature sensor and the resistor 116 is used as a heat-receiving sensor.

When the heater 115 is heated by supplying a constant electric power, the temperature sensor 114 and the heat-receiving sensor 116 increase their resistance value by the effect of heat from the heater 115.

While there is no flow of measurable fluid, e.g., gas, the temperature sensor 114 and the heat-receiving sensor 116 are equally increase their resistance value by the effect of heat. When gas flows in the direction indicated by an arrow along the substrate 111, the temperature sensor 114 decreases its resistance value, being deprived of its heat by the gas flow, and the heat-receiving sensor 116 increases its resistance value, receiving heat from the heater 115. A difference between the resistance values of the temperature sensor 114 and the heat-receiving sensor 116 is a function of the flow rate of the gas.

FIG. 30 is a perspective view for explaining another example of a conventional flow sensor. This flow sensor is composed of a semiconductor substrate 121 which has a cavity portion 124 having openings 122 and 123 at its left and right sides formed by anisotropic etching at the center portion thereof; a spatially isolated thin-film micro-bridge 125 bridging over the cavity 124 and having thereon a thin-film heater 126 and two temperature measuring resistors 127 and 128 disposed to insert therein the heater 126; and a thin-film temperature measuring resistor 129 for measuring ambient temperature disposed at a corner of upstream side thereof. The upper surface of each resistor is covered with an insulating film.

The flow sensor shown in FIG. 30 has the heater 126 disposed between two temperature-measuring resistors 127 and 128 on the micro-bridge 125 bridging over the cavity 124 and the ambient-temperature measuring resistor 129 which serves as a reference resistance. When the heater 126 is heated to a specified temperature, the temperature-sensing resistors vary their resistance values by the effect of a gas flow. The variation in resistance of each resistor is measured as a voltage value and a flow-rate or a flow of the gas is calculated from the measured values.

As described above, any conventional thermal type mass flowmeter adopts such a system in which a heater-resistor (heat-generating element) generates a heat and a heat-sensing resistor (heat-receiving element) disposed at a specified distance therebetween senses the transferred heat. Accordingly, the conventional flowmeter needs to use at least one pair of elements (a heat-generating element and a heat-receiving element), which must be identical in size, specific heat and heat capacity. Therefore, it involves the following problems to be solved:

[1] Variation of resistances of a heat generating element and a heat receiving element:

(1) It is required to correctly adjust electric circuits to compensate the variations of temperature, i.e., resistance characteristic of the heat-generating element and of the heat receiving-element respectively;

(2) Regarding the temperature balance, i.e., resistance balance between the heat-generating element and the heat-receiving element, both elements are made on a semi-conductor substrate by using micro-machining technology of IC production and may be generally said to be combined with relatively high accuracy. However, the elements may be of no use if their resistances are insufficiently balanced. The conventional coil type thermal flowmeter may use a combination of a separate heating element and a separate heat-receiving element which are selected as well balanced in their resistance characteristics, thereby it may be manufactured with higher productivity than the thermal flowmeter having the elements integrally made on a substrate;

(3) It is difficult to arrange the heat-generating element and the heat-receiving element at optimal positions with an optimal spacing. The elements are also limited by attainable accuracy;

(4) Since there is a distance between the heat generating-element and the heat-receiving element, it is impossible to correctly detect a differential resistance at a very small flow-rate of fluid;

(5) Each of the heat-generating element and the heat-receiving element shall have a high accuracy of temperature distribution. Any dispersion of the temperature distribution may affect a detection output signal and makes it necessary to additionally adjust each respective sensor circuit;

(6) Increasing the number of the heat-generating and heat-receiving elements increases the size of the substrate and the number of its output leads. When the substrate of an increased size is disposed in a stream of fluid to be measured, it may prevent the fluid from freely flowing and can not obtain the correct measurement result. This also leads to increasing the manufacturing cost. The accuracy of sensing a small flow-rate is also reduced;

(7) The increased number of heat-generating and heat-receiving elements increases the electric power consumption;

(8) The vertical arrangement of the heat-receiving element at the upper position and the heat-generating element at the lower position in a vertically upward stream of gas may be encountered with such a problem that even at absence of fluid flow the heat-receiving element generates an output signal, sensing an ascending current of air heated by the heat-generating element. This means that thus constructed flowmeter shall be mounted with special consideration of its mounting conditions and has a limitation of its mounting places.

[2] Regarding compensation for an ambient temperature when detecting a gas flow:

(1) In a flowmeter wherein a set of three micro-bridge resistors disposed at top, center and last from the upstream side in gas passage is used to detect a temperature of gas flow by the top resistor, detect gas flow by the center and the last resistors and compensate the measured flow rate for variation by the temperature data obtained by the top resistance, the problems (1) to (8) described above in item [1] regarding the variations in resistance of the heat generating element and the heat receiving elements may arise under worse conditions;

(2) A flowmeter, wherein a pattern of a resistor for sensing ambient temperature is formed on a semiconductor substrate, can not correctly detect a flow rate because the resistance value of the resistor for measuring ambient temperature slowly responds and changes with a change of temperature of the semiconductor substrate having a large heat capacity, thereby the correct temperature of gas at the moment of its flow-rate measurement cannot be detected.

The present invention proposes to apply a small current or a small voltage to a resistor disposed in a flow of fluid to be sensed and determine an ambient temperature from the measured resistance value; heat the resistor by applying a large current or a large voltage thereto and determine an ambient temperature plus a fluid flow from the sensed resistance value; calculate a difference between two sensed resistance values to determine the fluid flow rate.

FIGS. 31A and 31B are construction views for explaining an example of a flow sensor according to the present invention. FIG. 31A is a plan view and FIG. 31B is a sectional view taken along line B—B of FIG. 31A. There is shown a substrate 130, insulating film 131 and 132, a cavity portion 133, a resistor 134, terminals 135 and 136, a micro-bridge 137 and supporting portions 138 and 139.

As shown in FIGS. 31A and 31B, the substrate 130 is a silicon singlecrystal plate which has a square crystal plane (100) and is covered at its top surface with an insulating layer 131 of silicon nitride. A cavity portion 133 having a specified depth is formed by anisotropic etching in parallel with a crystal plane (100) along a diagonal line perpendicular to the direction indicated by arrow Q on the substrate, leaving an insulating layer 131 of a specified width to form a micro-bridge 137. A zigzag pattern of platinum or permalloy (e.g., Ni 80% and Fe 20%) of a thin layer resistor 134 is deposited onto the upper surface of the micro-bridge 137 and terminals 135 and 136 are also provided thereon. An insulating layer 132 of silicon nitride is further formed on the upper surface of the thin layer resistor.

FIGS. 32A and 32B are views for explaining principle of the operation of a flow sensor according to the present invention. FIG. 32A shows characteristic curves $A_1$ and $A_2$ of voltage developed across the resistor 134 heated by applying a current when fluid of 30° C. flows in the direction indicated by arrow Q in the device shown in FIG. 31A. These relate to flow characteristics: the curve $A_1$ is obtained at a flow rate of 2 liters per hour and the curve $A_2$ is obtained at a flow rate of 0 liter per hour. FIG. 32B shows temperature characteristic of the resistor 134 when the fluid does not flow, i.e., the fluid flows at flow rate of 0 liter per hour. The characteristic curves $B_1$, $B_2$ and $B_3$ are obtained at fluid temperature of 20° C., 30° C. and 40° C. respectively.

As shown in FIG. 32A, in case of applying a small current of, e.g., 2 mA or less to the resistance 134, the resistor 134 can not be heated and, therefore, an output voltage across the resistor 134 varies with a change of temperature of the fluid but it does not varies with a change of fluid flow rate. Namely, the flow characteristic curves $A_1$ and $A_2$ obtained at different flow rates show that a change of voltage (resistance) at small heating current (within the range of 0 to 2 mA) does not concern the flow rate and it relates to the fluid temperature only.

However, in case of applying an increased current of, e.g., 8 mA, the resistor 134 can be heated and, if fluid flows, its resistance may increase less than when the fluid being still. Accordingly, the flow characteristic curves $A_1$ and $A_2$ go apart from each other and show resistance values depending upon the flow rate. When the resistor 134 is heated to high temperature by applying a current of 8 mA, the output voltage rises to about 3 V (on the curve $A_1$) or 4 V (on the curve $A_2$). The more fluid that flows, the more heat radiation tends to reduce an increasing ratio of resistance value to electrical current of the resistor.

FIG. 32B indicates the case when the resistor 134 is disposed in fluid being still and heated with current supplied thereto. When a small current (too small to cause the resistor be self-heated) is applied to the resistor 134, the resistance value increases as temperature of the fluid (i.e., temperature of the resistance) rises. The output voltage correspondingly rises. Namely, the resistor 134 functions as a temperature-sensing element having the shown temperature characteristic.

According to FIGS. 32A and 32B, the flow rate of the fluid can be determined in such a way that one micro-bridge resistor (FIGS. 31A, 31B) is heated at a low temperature (with a small current) to sense the ambient temperature (i.e. the temperature of the resistor); the resistor is then heated at high temperature (with a large current) to sense the resistance value corresponding to the variation due to the fluid temperature plus the fluid flow rate; the resistance value (output voltage) sensed at the high temperature is reduced by the resistance value (output voltage) sensed at the low temperature to obtain the flow rate of the fluid.

FIGS. 33A and 33B are construction views for explaining another example of a flow sensor according to the present invention. FIG. 33A is a plan view and FIG. 33B is a sectional view taken along line B—B of FIG. 33A. There is shown a substrate 140, insulating layers 141 and 150, a cavity portion 143, a resistor 144, terminals 145 and 146, a cantilever insulation layer 147 and a free open end 1.49.

As shown in FIGS. 33A and 33B, the flow sensor has the square substrate 140 which includes a square cavity portion 143 formed by anisotropic etching to be parallel with the square substrate sides; a cantilever insulation layer 147 having the free open end 149 projecting over the cavity portion 143; the zigzag-pattern thin-layer resistor 144 with the terminals 145 and 146 formed on the cantilever insulation layer 147; and the insulation layer 150.

The flow sensor of FIGS. 33A and 33B is similar to the flow sensor of FIGS. 31A and 31B and differs only by that the resistor 144 is supported at one end on the substrate and projects over the cavity portion 143 and fluid to be sensed flows in the direction indicated by arrow Q parallel to the sides of the square substrate 140.

FIGS. 34A and 34B are views for explaining examples of driving circuits of a flow sensor according to the present invention. FIG. 34A is a constant current drive circuit and FIG. 34B is a constant voltage drive circuit. In these drawings, there are shown a constant current source 151A, a constant voltage source 151B, a sensing element 152 (corresponding to the resistor 134 of FIGS. 31A, 31B and the resistor 144 of FIGS. 33A, 33B).

In the constant current drive circuit of FIG. 34A, the constant current source 151A is connected with the sensing element 152 through a switch SW having contacts a, b and c. An output voltage Vout across the sensing element is detected. When the switch SW turns on its contact a, the sensing element 152 is connected parallel to the resistor R to be driven with a current for low-temperature heating. When the switch turns on its contact b, the sensing element 152 is driven with a current for high-temperature heating. When the switch turns to contact c, the circuit is open to stop heating.

In the constant voltage drive circuit of FIG. 34B, the constant voltage source 151B, reference resistor Ro and the sensing element 152 are connected in series with each other through a switch SW having contacts a, b and c. An output voltage Vout develops across the reference resistance Ro. A resistor R or a corresponding potential zener diode is connected in series with the contact "a" of the switch SW to form a driving circuit for low temperature heating. When the switch SW turns to contact b, the sensing element 152 is connected directly to the source omitting the resistor to form a driving circuit for high temperature heating. When the switch turns to contact c, the circuit is open to stop heating.

FIGS. 35A and 35B are views for explaining the operation of a pulse drive circuit of a flow sensor according to the present invention. FIG. 35A illustrates a waveform of a driving current pulse and FIG. 35B illustrates a waveform of an output voltage when driving the sensing element by using the current pulse shown in FIG. 35A.

FIG. 35A is illustrative of a correlation between switching time and current to be supplied to the sensing element when a switch SW of the constant current drive circuit of FIG. 34A switches its contacts a, b and c at specified respective intervals. A period "a–d" is for heating the sensing element at low temperature by applying thereto a small current of 2 mA, a subsequent period "b–d" is for heating the sensing element at high temperature by applying thereto a large current of 8 mA and a further subsequent period "c–d" is for pausing the heating by opening the source circuit. FIG. 35B shows an output voltage of the sensing element 153, where P and Q are time points at which the output voltage becomes stabilized, i.e., timing points for output measurement.

FIGS. 36A to 36D are illustrative of the operation principle of the flow sensor according the present invention when temperature of fluid to be sensed varies and when the flow rate of fluid varies. FIG. 36A shows variation of temperature of fluid with time, FIG. 36B shows variation of flow rate of fluid with time, FIG. 36C shows a waveform of current applied to the sensing element and FIG. 36D shows waveforms of detection output voltages measured when temperature of fluid changed and when flow rate of fluid changed.

As shown in FIG. 36C, a current to be supplied to the sensing element 152 is a pulse consisting of a small current (2 mA) and a subsequent large current (8 mA), which is repeatedly supplied at specified intervals of pause. In the case shown, the current pulse is supplied one for each period ($t_0$–$t_1$, $t_1$–$t_2$, $t_2$–$t_3$). On the other hand, the fluid temperature varies from a constant temperature L2 (30° C.) to a temperature L1 (20° C.) or L3 (40° C.) for a period $t_1$–$t_2$ as shown in FIG. 36A, and the fluid flow rate varies from a constant level L5 (2 liters per hour) to a level L4 (0 liter per hour) or L6 (4 liters per hour) for a period $t_2$–$t_3$.

Namely, there is no change in both the fluid temperature and the fluid flow rate for the period $t_0$–$t_1$, a change in the fluid temperature occurs for the period $t_1$–$t_2$ and a change in the fluid flow rate occurs for the period $t_2$–$t_3$.

Accordingly, the detection output voltage takes a waveform (L2, L5) corresponding to the constant temperature and constant flow rate for the period $t_0$–$t_1$ and a waveform (L1 or L3) corresponding to the change of the fluid temperature for the period $t_1$–$t_2$.

The output voltage at the small driving current is subtracted from the output voltage at the large driving current for each case. These subtraction results are the same constant values. It is apparent that there is no difference between the differential output voltages in regard to temperature variations.

The output voltage becomes L4 or L5 or L6 in accordance with the fluid flow-rate for the period $t_2$–$t_3$, but the output voltage at a small driving current does not vary with a change of the flow rate because of the temperature being constant. Since the change of the output voltage of the sensing element at large driving current is caused by the effect of heat radiation in combination with the fluid flow, the difference between two output voltages at the small current and the large current corresponds to the fluid flow rate. Practically, the fluid to be sensed may change its flow rate and temperature at the same time. Namely, it may have both variations in temperature (for period $t_1$–$t_2$) and flow rate (for period $t_2$–$t_3$) for each detection period. Therefore, a change of the fluid flow rate can be detected by subtracting the detection voltage at the small driving current (a change in temperature of the fluid to be sensed) from the detection voltage at the large driving current (a change in flow rate and temperature of the fluid to be sensed).

FIGS. 37A and 37B show further examples of driving current waveforms and output voltage waveforms of a flow sensor according to the present invention. When the sensing element is driven with a triangular (sawtooth) current proportional to time for a period $t_1$–$t_2$ as shown in FIG. 37A an output voltage with a time lag is detected as shown in FIG. 37B. Similarly to the case of FIG. 35B, the voltages produced by applying a small driving current and a large driving current are measured at measurement time points P and Q whereat the resistor's temperature is stabilized. By doing so, it is possible to determine the flow rate in the same way as the foregoing embodiment. Driving the sensing element with a constant saw-tooth current eliminates the possibility of influence of the resistors R, Ro shown in FIGS. 34A, 34B and enables to use only one power source which can be precisely manufactured and requires only setting measurement time points P and Q. FIGS. 38A and 38B are illustrative of current wavefoms for driving a sensing element of a flow meter according to the present invention. FIG. 38A shows a waveform of an approximately triangular pulse of current whose variation decreases convexly with time. FIG. 38B shows waveform of an approximately triangular pulse of current whose variation increases concavely with time. These pulses may be used in the same way as the triangular pulses of FIG. 37A if a stabilized power source is available.

FIG. 39 is an electrical circuit diagram showing an example of a driving circuit of a flow meter according to the present invention. In FIG. 39, 152 is a sensing resistor, 153 is a circuit (constant current circuit) for supplying a constant current to the sensing element, 154 is a detecting circuit for detecting the output of the sensing element 152, 155 is a coefficient setting circuit, 156 is a hold circuit, 157 is a subtraction circuit and 158 is an output terminal.

The constant current circuit 153 is connected in series with a sensing element 152 and reference resistor Rr with a grounded end. The voltage of the reference resistor Rr is fed back to an inverting input terminal of the constant current circuit 153. A non-inverting input terminal of the constant current circuit 153 is connected with a switch $SW_1$ which has contacts "a" and "b" for supplying reference voltages $V_{REF}1$ and $V_{REF}2$ respectively and a grounded contact "c". These reference voltages $V_{REF}1$ and $V_{REF}2$ are set as follows:

$$V_{REF}1 = 2Sr \text{ (mV)} \qquad (7)$$

$$V_{REF}2 = 8Rr \text{ (mV)} \qquad (8)$$

The connecting point of the output terminal of the constant-current circuit 153 and one terminal end of the sensing element 152 are connected to an inverting input terminal of the detecting circuit 154, and the other termial end of the sensing element 154 is connected to the non-inverting input terminal of the detecting circuit 154. An output terminal of the detecting circuit 154 is connected to a switch $SW_2$ which has contacts "a" and "b": the contact "a" is used for setting a coefficient K for converting a low heating temperature (not to cause the resistance to be heated) to an ambient temperature when calculating a flow rate, for example, by connecting thereto the coefficient setting circuit 155 which can vary a multiple factor in accordance with a set value of the coefficient K, and contact "b" is connected to an input terminal of the subtraction circuit 157 for inputting thereto an output voltage $V_D$ when a large current is supplied for heating at a high temperature. A switch $SW_3$ having contacts "a" and "c" and the hold circuit 156 are provided between the coefficient setting circuit 155 and the subtraction circuit 157. The contact "a" of the switch $SW_3$ is connected to the hold circuit 156.

The switches $SW_1$, $SW_2$, $SW_3$ of the thus constructed driving circuit are interlocked with each other and operate with changing-over their respective contacts "a", "b", "c" at a time. When a switch turns on its contact "a", a voltage equal to the reference voltage Vref1 is applied to the reference resistor Rr connected to the inverting terminal of the constant current circuit 154 and a constant current of 2 mA flows through the sensing element 153. Similarly, when the switch turns on its contact "b", a voltage equal to the reference voltage Vref2 is applied to the reference resistor Rr and a current of 8 mA flows through the sensing element 153.

FIGS. 40A to 40H are illustrative of waveforms of voltages at corresponding portions of the driving circuit shown in FIG. 39. Referring now to FIG. 39 and FIGS. 40A to 40H, the operation of the driving circuit will be described as follows:

The switch $SW_1$ (together with the switches $SW_2$ and $SW_3$) operates to close its contact "a" and open contact "b" by corresponding driving voltage pulses of waveforms shown in FIGS. 40A and 40B at intervals of $t_1$ to $t_1$ and $t_2$ to $t_3$. A driving current of 2 mA and 8 mA shown as "is" in FIG. 40C follows through the sensing element 152 in accordance with above-mentioned switching operations. When the contact a is closed, a voltage Vs, which is proportional to an ambient temperature and has a waveform shown in FIG. 40D, appears at the contact "a" of the switch $SW_2$. The voltage Vs is inputted into the coefficient setting circuit which in turn multiplies the voltage by a preset coefficient K and outputs the resultant voltage V's (=KVs) shown in FIG. 40E. Since the output voltage Vs produced by closing the contact "a" of the switch $SW_2$ is not correctly proportional to an ambient temperature, it is corrected by the coefficient K which is given by the following equation:

$$K = (V_D - \text{change by humidity})/Vs \qquad (9)$$

The hold circuit 156 outputs a voltage Vs" being equal to the voltage Vs' (=Vs") shown in FIG. 40F. The subtraction circuit 157 receives the voltages VD and V"s and generates at the terminal 158 an output voltage V shown in FIG. 40H, which is proportional to a flow rate.

$$V = V_D - Vs" \qquad (10)$$

FIG. 41 is a block diagram showing another example of another driving circuit of a flow meter according to the present invention. In FIG. 41, 159 is a voltage detection circuit, 160 is a current detection circuit and 161 is a dividing circuit. Other parts similar in function to the parts shown in FIG. 39 are given like reference numerals.

The driving circuit of FIG. 41 is to detect a flow rate by a change of resistance in the sensing element 152. Whenever the sensing element 152 is driven with a small current and a large current, the voltage detection circuit 159 detects a voltage across the sensing element 152 and inputs it into the dividing circuit 161. On the other hand, the current detection circuit 160 detects a voltage across the reference resistor Rr having a known resistance and inputs it into the dividing circuit 161 which in turn calculates the resistance value of the sensing element 152.

The circuitry (behind the switch $SW_2$) operates on the principle similar to the driving circuit of FIG. 39 and calculates a flow rate by subtracting a voltage produced by driving with a small current pulse from a voltage produced by driving with a large current pulse.

FIGS. 42A to 42E show a timing chart for explaining the driving operation of a flow meter according to the present invention. FIG. 42A indicates a driving current pulse corresponding to the driving pulse shown in FIG. 35A. FIG. 42B indicates a waveform of a driving sawtooth current corresponding to the driving current shown in FIG. 37A. FIG. 42C shows a series of clock pulses, FIG. 42D shows a measurement ON-OFF signal and FIG. 42E shows a reset signal.

Time points P, Q shown in FIGS. 35B and 37B are determined on condition that an output voltage of the sensing element 152 is stabilized. A measurement start timing point "ta" in case of low-temperature driving and a measurement start timing point "tb" in case of high-temperature driving can be determined directly if a timing point "to" for thermally driving the sensing element 152 is determined.

Namely, the measurement timing points P and Q are determined as the time "ta" and the time "tb", respectively, i.e., "ta" is a duration to a time point "a" at which driving pulse waveform of FIG. 42A or the driving sawtooth waveform of FIG. 42B intersects line A—A, and "tb" is a duration to a time point "b" at which intersects line B—B.

A driving period from $t_0$ to $t_1$ and a pause period from $t_1$ and $t_2$ are determined by measurement ON-OFF signals shown in FIG. 42D, and a reset signal shown in FIG. 42E is generated at the time $t_1$ whereat driving the sensing element is completed. All these timing point ta, tb, $t_1$, $t_2$ are also measured and defined by counting clock pulses as shown in FIG. 42C.

FIG. 43 is an electrical block diagram showing an example of timing-signal generating method according to the present invention. In FIG. 43, 162 is a clock pulse generating circuit, 163a, 163b, 163c are counters and 164 is a reference voltage (driving current) generating circuit.

The clock pulse generating circuit 162 generates clock pulse signals shown in FIG. 42C. When the counter circuit 163a counts the preset number of clock pulses corresponding to the time (period) "ta", it generates a timing pulse "a" to start measurement. Similarly, when the counter circuit 163b counts the preset number of clock pulses corresponding to the time (period) tb, it generates a timing pulse "b" to start measurement. The counter circuit 163c outputs a timing pulse corresponding to the driving time $t_1$ for a measurement ON-OFF signal and a timing pulse corresponding to the pause time $t_2$. The counter circuits 163a and 163b are reset and counting circuit of these counter circuit are closed by a pulse signal defining the time $t_1$. Gates of the counter circuits 163a and 163b are opened by a pulse defining the time $t_2$. At the same time, the reference-voltage generation circuit 164 is driven to generate a reference voltage (driving current) for driving the sensing element. FIG. 44 shows an example of a reset circuit and FIGS. 45A to 45D are illustrative of a time chart of the reset circuit shown in FIG. 44. When a measurement ON-OFF signal (output signal of the counter 163c) of FIG. 45B is applied to an input terminal D of a delay flip-flop circuit 165, an output corresponding to the ON-OFF signal is given with a time lag of 1 clock pulse as shown in FIG. 45C. A reset signal of a clock-pulse width shown in FIG. 45D is generated as an AND-output (output of the AND-circuit 167) from an inverted signal (output of the inverting circuit 166) and an output of the flip-flop 165.

FIG. 46 is illustrative of a block circuit diagram of a sawtooth-current drive circuit for driving a sensing element according to the present invention, which includes a resistore Ro for receiving the reference voltage E, an integrating circuit composed of said resistance Ro, a feedback condenser Co and an operating amplifier 168, and a switch 169 for discharging the feedback condenser according to a reset signal. This driving circuit generates a sawtooth voltage $V_1$ that is proportional to time t within the period defined by a reset signal.

$$V_1 = (E/CoRo) \cdot t \quad (11)$$

The voltage $V_1$ is applied to a constant current circuit composed of the operational amplifier 170 having a reference resistance Rr and four resistances Ra equal to the input resistance. A constant sawtooth current "i" proportional the voltage $V_1$ flows to a sensing element. The current "i" is determined according to the following equation (12):

$$i = \frac{V_1}{Rs} = \frac{1}{Rs} \times \frac{E}{CoRo} \times t \quad (12)$$

FIG. 47 is a block circuit diagram for explaining an example of a flow-rate measuring circuit using a sensor element with a sawtooth current drive according to the present invention, which includes amplifier circuits 171 and 172, a coefficient setting circuit 173, hold circuits 174 and 175 and a subtraction circuit 176.

When a constant sawtooth current "i" determined by the equation (12) flows through a sensing element 152, a voltage is developed across the sensing element 152 and enters into the amplifier circuits 171 and 172 connected in parallel to the sensing element. The amplifier circuit 171 is used for measuring an output voltage Vs produced at a small driving current and is provided with the coefficient setting circuit 173 and the hold circuit 174 connected in series thereto. The amplifier circuit 172 is provided to measure an output voltage $V_D$ produced at a large driving current and the hold circuit 175 is connected thereto.

The hold circuit 174 holds, with a measurement timing pulse "a", a corrected voltage Vs' which is obtained by multiplying the output voltage Vs produced at a small driving current by the coefficient K. The hold circuit 175 holds, with timing pulse "b", a voltage $V_D$ produced at a large driving current.

The output voltage Vs" (=Vs') produced at the small driving current, which is hold by the hold circuit 174, and the output voltage $V_D$ produced at a large driving current, which is hold by the hold circuit 175, are entered into the subtraction circuit 176 which subtracts the voltage Vs" from the voltage $V_D$ and generates resultant voltage V being proportional to the flow rate. Assuming that the small driving current for heating the sensing element at low temperature is 2 mA and the large driving current for heating the sensing element at high temperature is 8 mA, constants Co, Ro, Rs and E of the circuit are determined from the equation (12) in such a way that 2 mA at t=ta and 8 mA at t=tb may be assured.

FIG. 48 is an electrical circuit diagram for explaining another example of a flow-rate measuring circuit with a saw-tooth current drive according to the present invention. In FIG. 48, there are shown a reference voltage generating circuit 177, an amplifier circuit 178, an A-D converter 179 and a CPU (central processing unit) 180. Other parts similar in function to the parts shown in FIG. 46 are given like reference numerals.

The flow-rate measuring circuit of FIG. 48 uses clock pulses from a clock of the CPU 180 as timing signals (i.e., measurement ON-OFF signal, measurement timing signals "ta" and "tb" and reset signal). The CPU 180 has storing function and, therefore, eliminates the necessity of providing a special hold circuit for holding output voltages sensed at a low temperature and a high temperature. The output voltages of a sensing element 152 are amplified by an amplifier circuit 178 to specified voltage values which are then converted by the A-D converter 179 into digital values. The CPU reads and stores digital values of the detected voltages according to the timing signals "ta" and "tb" and then sets coefficients and performs arithmetic operations on the digital data, easily determining the flow rate.

FIG. 49 is a view for explaining an example of a flow-rate measuring circuit of a sensing element according to the present invention, which is featured by using a voltage pulse for driving the sensing element. In FIG. 49, numeral 181a designates a first reference voltage generating circuit, numeral 181b designates a second reference voltage generating circuit and numeral 182 designates a constant voltage circuit. Other parts similar in function to the parts shown in FIG. 48 are given like reference numerals.

The first reference voltage generating circuit 181A is a constant voltage circuit which applies a low reference voltage $V_{REF}1$ to a sensing element 152. The second reference voltage generating circuit 181B is a constant voltage circuit which applies a high reference voltage $V_{REF}2$ to a sensing element 152. Each constant voltage circuit is connected to contacts "a" and "b" of a switch $SW_1$ which is operated by timing pulses from a terminal $P_{01}$ of a CPU 180 and has a grounded contact "c." The switch $SW_1$ is also connected to a non-inverting input of the constant voltage circuit 182.

The constant voltage circuit 182 is loaded with a reference resistance Rr and the sensing element 152 which is connected at one end in series with the reference resistance Rr and at one end to the ground. The connecting point is connected to an inverting input terminal of the constant-voltage circuit 182. In the constant voltage circuit 182, a voltage Vs across the sensing element 152 is equal to a voltage applied to corresponding contact of the switch $SW_1$, i.e., a constant output voltage is supplied: $Vs=V_{REF}1$ when contact "a" is selected;

Vs=VREF2 when contact "b" is selected;

Vs=0 when contact "c" is selected.

When the voltage Vs of the sensing element 152 having resistance Rs is constant, a current "is" flowing through the reference resistor Rr is equal to Vs/Rs and a current corresponding to the resistance Rs flows through the sensing element 152. For instance, when the resistance Rs varies under the influence of temperature or flow rate of fluid, the current "is" flowing in the resistance Rs varies correspondingly. This current "is" is detected as a voltage $Vr(=is \times Rr)$ by an amplifier circuit 178.

FIG. 50 shows a time chart for explaining the operation of the circuit of FIG. 49, on the assumption that $V_{REF}1=0.5$ V and $V_{REF}2=4.5$ V. In this case, Vs=0.5 V is applied for a period $t_1$ the contact "a" of the switch SW1 being closed, Vs=4.5 is applied for a period $t_2$ the contact "b" of the switch $SW_1$ being closed, and a pause (with no driving voltage) is produced for a period $t_3$ the contact "c" being selected. Driving pulses similar to those of FIG. 35A are obtained. The sensing element is heated at a low temperature while the switch $SW_1$ closes its contact "a". This corresponds to the case of heating with a constant current of 2 mA. The sensing element is heated at a high temperature while the switch $SW_1$ closes its contact "b". This corresponds to the case of heating with a constant current of 8 mA.

FIG. 51 is a plan view for explaining another example of a flow sensor embodying the present invention. In FIG. 51, there are shown a substrate 184, insulation layer 185, a cavity portion 186, a heating resistor 187, a sensing resistor 188 and a micro-bridge 189.

As shown in FIG. 51, this flow sensor is composed of the semiconductor substrate 184 having the cavity portion 186 and the micro-bridge 189 of insulation layer formed perpendicular to the flow direction on the substrate, the zigzag-patterned heating resistor 187 formed on the micro-bridge 189 and the zigzag-patterned temperature-sensing resistor 188 disposed inside the heating resistor 189. The sensor is intended to measure a fluid flow by using two resistor at a time.

FIG. 52 is an electrical circuit diagram of the flow meter shown in FIG. 51. In this case, the flow measurement can be performed by sensing an output voltage Vout that is developed across terminals B-C of the temperature sensing resistor 188 by applying a constant current to the heating resistor 187. It is also possible to control a current flowing in the resistor 188 so as to always maintain a constant output voltage Vout across the terminals B-C while the fluid flows and to convert the controlled value of current to the flow rate.

FIG. 53 is a perspective view for explaining another example of a flow meter according to the present invention.

In FIG. S3, there are shown a silicon substrate 190, cavity portions 191 and 192, oxide film substrates 193 and 194, resistors 185 and 186. This flow meter also uses two resistors 195 and 196 at a time to measure a flow rate of a fluid.

The flow-rate sensing element shown in FIGS. 31A and 31B has a single sensing element being a resistor 134 of micro-bridge configuration, which is continuously heated first at a low temperature and subsequently at a high temperature for, e.g., 50 ms each. Practically, such a sudden change of an atmosphere may not occur, but, ideally, it is desired to heat a single sensing element 134 at a low temperature and a high temperature at the same time and to detect a difference of resistance values. However, it is impossible to heat the sensing element of FIGS. 31A and 31B at the same place simultaneously at a low temperature and a high temperature.

FIGS. 54A to 54D show a time chart for determining a flow rate by using the sensors of FIGS. 51 and 53.

As shown in FIG. 54A, a sequence of equally spaced clock pulses ($a_1$, $a_2$, $a_3$ ...) is generated at a fixed time interval from a clock circuit (not shown).

FIG. 54B shows that a series of small current pulses ($b_1$, $b_2$, $b_3$ ...) in synchronism with the clock pulses ($a_1$, $a_2$, $a_3$ ...) is generated to heat the resistor 188 (196) at a low temperature to produce and measure a resistance value proportional to a temperature.

FIG. 54C shows that a series of large current pulses ($c_1$, $c_2$, $c_3$ ...) in synchronism with clock pulses ($a_1$, $a_2$, $a_3$ ...) is generated to heat a resistor 188 (195) between terminals B-A at high temperature to produce and measure a resistance value proportional to a temperature and a flow rate.

FIG. 54D shows a series of flow-rate sensed pulses ($d_1$, $d_2$, $d_3$ ...) having amplitude is proportional to the fluid flow rate and which, in synchronism with the clock pulses ($a_1$, $a_2$, $a_3$ ...) is obtained by subtracting the resistance value of the resistor 106 heated at low temperature from the resistance value of resistor 105 heated at high temperature by the use of a flow-rate calculation circuit (not shown).

FIGS. 55A to 55C show another time chart for determining a flow rate by the use of the flow rate sensor of FIG. 53. Clock pulses ($a_1$, $a_2$, $a_3$ ...) shown in FIG. 55A have the same intervals as those of FIG. 54A and are used for synchronizing the operations of circuits driving the resistors 195 and 196.

The driving method with the time chart of FIGS. 55A to 55C is a further improvement of the driving method with the time chart of FIGS. 54A to 54D. The improved driving method is to simultaneously drive the resistor 195 at a high temperature and the resistor 196 at a low temperature for a specified period and to subsequently drive the resistor 195 at the low temperature and the resistor 196 at the high temperature for a specified period, making each resistor sense a temperature and a temperature plus a flow rate alternately.

While the resistor 196 between terminals B-C is heated with a current pulse $b_1$ at a low temperature in synchronism with a clock pulse ($a_1$) of FIG. 55A, the resistor 195 between terminals B-A is heated with a current pulse ($c_1$) at a high temperature. At the time of clock pulse $a_1$, a flowrate-sensed pulse (not shown) is determined by subtracting a temperature-sensed resistance value obtained by heating with the pulse b1 from a temperature-flowrate-sensed resistance value obtained by heating with the pulse $c_1$. At the subsequent time of clock pulse $a_2$, a flowrate-sensed pulse is determined by subtracting a temperature-sensed resistance value obtained by heating with the pulse $C_2$ from a temperature-flowrate-sensed resistance value obtained by heating with the pulse $b_2$.

As apparent from the foregoing, the present invention provides the following advantages:

(1) Any conventional separate arrangement of a heat-generating element and a heat-receiving element (at a distance therebetween) cannot detect quick change in flow rate. On the contrary, the flow sensor according to the present invention can accurately detect a fast varying flow rate of the fluid.

(2) Following-up control for temperature compensation is faster than conventional devices since the sensing element has an excellent thermal response characteristic.

(3) A Conventional method conducts temperature detection at 2 or 3 places. Temperature compensation, therefore, may be of no use if the ambient temperature is different at respective places. On the contrary, the present invention provides a single element that detects all at one place, assuring correct temperature compensation even if the ambient temperature distribution being sharply variable.

(4) In contrast to the arrangement of several micro-bridges in which upstream resistor may disturb a flow of fluid or resist the fluid flow, a single-element device can accurately measure the flow rate without disturbing the flow.

(5) Use of a single sensing element eliminates the necessity of matching with other elements. This may increase the yield of production of the elements because of lightened requirements on variations in resistance and temperature rising characteristics.

(6) The self-compensating (for temperature) detection system can attain high accuracy of micro-flow measurement because no element requires an accurate arrangement.

(7) Variation in temperature distribution of a respective heating element in itself scarcely affects the measurement. This may increase the yield of production of heating elements (therefore, flow sensors).

(8) Use of a single sensing element makes it possible to reduce the size of a sensor (substrate) to avoid preventing the flow of fluid to be sensed. The number of wires is also fairly reduced (to 2–4 wires) in comparison with any conventional device. The single-element type flow-sensor according to the present invention is very compact and inexpensive to manufacture and is adapted to use in monitoring a minute flow distribution.

(9) The flow sensor consumes a reduced amount of electric power.

(10) The flow sensor can be freely mounted.

We claim:

1. An atmosphere measuring device for sensing presence of a specified gas in an atmosphere according to a change in resistance of a resistor heated in an ambient atmosphere, comprising:

a specified temperature driving circuit for heating the resistor by application of a predetermined first current to the resistor to produce uniform heating along the resistor with a specified temperature increase to a substantial thermal equilibrium whereat the resistance of the resistor is substantially free of influence from said specified gas existing in the atmosphere and is indicative of an ambient temperature;

a high-temperature driving circuit for heating the resistor by application of a predetermined second current to the resistor to produce uniform heating along the resistor with a high temperature increase to a substantial thermal equilibrium whereat the resistance of the resistor varies by the effect of the ambient temperature and the specified gas presence;

a comparator circuit for comparing with each other two voltages generated across the resistor representative of resistances at the high temperature and the low temperature to determine a density of the specified gas contained in the atmosphere from an output voltage of the comparator circuit.

2. An atmosphere measuring device according to claim 1 for measuring density of a specified gas, further comprising:

an ON-OFF signal generating circuit for controlling said specified temperature heating circuit and said high temperature heating circuit to produce a high-temperature and a specified-temperature heating period and a heating-OFF period (pause);

a reference signal generating circuit responsive to said ON-OFF signal generating circuit for heating the resistor in synchronism with the high temperature and the specified temperature heating periods;

a time measuring circuit for determining a timing to read said two voltages representative of the resistance values of the resistor heated to a specified temperature and a high temperature in synchronism with the specified and the high temperature heating cycles;

a voltage measuring circuit for reading the voltages produced by the resistor in synchronism with the timing signal for reading the resistance values of the resistor;

a coefficient setting circuit for setting a coefficient for compensating a voltage produced by the resistor heated to the specified temperature by multiplying it by the coefficient to obtain and output a compensated voltage corresponding to an ambient temperature; and a memory circuit for storing the compensated voltage and a subtraction circuit for subtracting the memorized compensating voltage from the voltage produced by the resistor heated to the high temperature to determine a density of a specified gas in the atmosphere in proportion to the output of the subtraction circuit.

3. An atmosphere measuring device according to any one of claims 1 and 2, wherein the resistor is a thin heating wire capable of generating heat by applying an electric power thereto, which is formed to a micro-bridge circuit supported at both ends by electro-conducting pins with insulation in an atmosphere to be measured.

4. An atmosphere measuring device according to any one of claims 1 and 2, wherein a heating cycle of the resistor comprises a specified temperature and heating period high temperature heating period for heating the resistor at the specified temperature and the high temperature and a heating-OFF period for allowing a resistance value characteristic of thermal-equilibrium of the resistor to return to at least a resistance value at an ambient temperature.

5. An atmosphere measuring device according to any one of claims 1 and 2, wherein electric power for heating the resistor for the specified temperature heating period and the high temperature heating period is applied in the form of a low-crest pulse of voltage or current and a high-crest pulse of voltage or current to be outputted directly after the low-crest pulse of voltage or current.

6. An atmosphere measuring device according to any one of claims 1 and 2, wherein electric power for heating the resistor for the specified temperature heating period and the high temperature heating period is applied in the form of a saw-tooth voltage or current having a series of triangle-shaped peaks.

7. An atmosphere measuring device for measuring density of a specified gas, comprising:
- an atmosphere sensor having a substrate including therein two neighboring cavities of the same size and form and equivalent resistors connected in series to each other and arranged in form of a micro-bridge in the top surface of each of the cavity;
- a clock circuit for generating clock pulses for providing a timing to simultaneously drive resistors of the atmosphere sensor;
- driving circuit for outputting a low power pulse for inducing small scale heating of one of the resistors and a high power pulse for inducing large scale heating of the other resistor in synchronism with the clock pulse;
- means for measuring resistance values of said resistors; and
- an arithmetic computation circuit for comparing two resistance values produced in the resistors respectively at a specified temperature and at a high temperature and calculating a density of a specified gas according to the comparison result.

8. An atmosphere measuring device for measuring density of a specified gas, comprising:
- a substrate including therein two neighboring cavities of the same size and form and equivalent resistors connected in series to each other and arranged in the form of a micro-bridge in the top surface of each of the cavities;
- a clock circuit means for generating clock pulses for providing a timing signal to drive said resistors of the atmosphere sensor;
- a driving circuit means for outputting a low power pulse for heating one of the resistors to a specified temperature and a high power pulse for heating the other resistor to a high temperature;
- the driving circuit means including means for alternately applying one after the other said low power pulse to said one of the resistors and said high power pulse to said other resistor in synchronism with clock pulses from the clock circuit means;
- means for determining resistance values of said equivalent resistors while being driven by said low and high power pulses respectively; and
- an arithmetic computation circuit for comparing the resistance values produced in the resistors respectively at a specified temperature and at a high temperature and calculating a density of a specified gas according to the comparison result.

9. A flow measuring device having structure, function and components according the to the density measuring device of claim 7 further comprising:
- means for operating said driving circuit in alternating first and second modes;
- wherein in said first mode, the said low power pulse is applied to said one resistor while simultaneously said high power pulse is applied to said other resistor;
- wherein in said second mode said supply means applies said low power pulse to said other resistor while simultaneously applying said high power pulse to said one resistor; and
- wherein said first and second modes alternate in synchronism with the clock pulses from the clock circuit.

10. An atmosphere measuring method whereby a single resistor is inserted in a gas flow to be measured, a small predetermined current substantially unable to noticeably heat the resistor is supplied to the resistor and a resistance thereof is measured, a large predetermined current is subsequently supplied to heat the resistor in a uniform axial manner and a resistance thereof is measured, and a flow rate of gas is determined by subtracting the resistance measured without noticeably heating from the resistance measured with heating uniform heating current by means of detecting voltages generated across the resistor while at substantial thermal equilibrium which are representative of the resistances.

11. An atmosphere measuring method for determining flow of a gas, whereby a single resistor is inserted in a gas flow to be measured, a slowly increasing current is supplied to the resistor, a resistance produced in the resistor at a small predetermined current substantially unable to noticeably heat the resistor and a resistance produced in the resistor at a large predetermined current enough to heat the resistor in a uniform axial manner are measured and a flow rate of the gas is determined by subtracting the resistance measured while said small predetermined current is applied and said resistor is at substantial thermal equilibrium from the resistance measured while said large predetermined current is applied and said resistor is at substantial thermal equilibrium wherein the resistances measured are determined from voltages detected across said resistor.

12. A flow measuring device for determining gas flow, comprising a substrate having a cavity therein, a thin insulation layer formed in the form of a bridge across an upper part of the cavity, a single resistor disposed on the thin insulation layer, means for sensing a resistance value of the resistor by applying thereto a small current or voltage insufficient to cause a heat therein, means for sensing a resistance value of the resistor heated in a uniform axial manner by applying a large current or voltage thereto, means for subtracting the sensed resistance value of the resistor at the small current or voltage from the sensed resistance value of the resistor at the large current or voltage to determine a flow of gas to be measured according to the subtraction result.

13. A flow measuring device according to claim 12, further comprising means for generating a repeatable cycle consisting of a flow measuring period for supplying said small current and subsequently supplying said large current and a pause period for supplying no current, said pause period being longer than a time necessary, for returning a temperature of the resistor to a temperature of gas to be sensed.

14. A flow measuring device according to claim 12, wherein a voltage or a current to be supplied to the resistor for the flow measurement period is a low-crest pulse and a high-crest pulse outputted directly after the low-crest pulse.

15. A flow measuring device according to claim 12, wherein a voltage or current to be applied to the resistor for the flow measuring period is a saw-tooth voltage or current.

16. A flow measuring method for determining gas flow rate, using two resistors inserted in a gas flow to be measured, comprising:
- simultaneously applying one of a first current or voltage at a level below that necessary to induce substantive self-heating to one of the two resistors and one of a second current or voltage to the other resistor at a level greater than that of said one of said first current or voltage and sufficient to induce substantive self-heating;
- determining resistance values of the two resistors from said one of said first current or voltage and said one of said second current or voltage;

calculating a difference between the two measured resistance values; and determining a flow rate of the gas flow from the difference of the two resistance values.

17. A gas flow measuring device comprising:

a substrate defining a cavity, engraved therein; an insulation layer formed in the form of a bridge across an upper part of the cavity;

two resistors disposed on the insulation layer;

supply means for simultaneously applying one of a first current or voltage at a level below that necessary to induce substantive self-heating to one of the resistors and one of a second current or voltage to the other resistor at a level greater than that of said one of said first current or voltage and sufficient to induce substantive self-heating;

means for determining resistance values of both of said resistors from said ones of said first and second currents and voltages applied to respective ones of said resistors; and means for subtracting the one measured resistance value from the other measured resistance value to determine a flow of the gas from a difference of the resistances.

18. A gas flow measuring device for determining gas flow, comprising:

a substrate defining a cavity, engraved therein;

two insulation layers bridged across a top part of the cavity;

two resistors disposed on respective ones of said insulation layers;

supply means for simultaneously applying one of a first current or voltage at a level below that necessary to induce substantive self-heating to one of the resistors and one of a second current or voltage to the other resistor at a level greater than that of said one of said first current or voltage and sufficient to induce substantive self-heating;

means for determining resistance values of both of said resistors from said ones of said first and second currents and voltages applied to respective ones of said resistors; and means for subtracting the one measured resistance value from the other measured resistance value to determine a flow of the gas from a difference of the resistances.

19. A flow measuring device according to any one of claims 16 and 18, further comprising:

a clock-pulse generating circuit for generating clock pulses for providing a timing to simultaneously drive said two resistors;

said supply means including a low power pulse generating circuit for applying said one of said first current or voltage to one of the resistors in synchronism with one of said clock pulses; and said supply means including a high power pulse generating circuit for applying said one of said second current or voltage to the other resistor in synchronism with said one clock pulse.

20. A flow measuring device according to claim 18 further comprising:

means for operating said supply means in alternating first and second modes;

wherein in said first mode said one of said first current or voltage is applied to said one resistor while simultaneously said one of said second current or voltage is applied to said other resistor;

wherein in said second mode said supply means applies said one of said first current or voltage to said other resistor while simultaneously said one of said second current or voltage is applied to said one resistor; and wherein said first and second modes alternate in synchronism with the clock pulses from the clock circuit.

* * * * *